(12) United States Patent
Tu et al.

(10) Patent No.: US 8,658,131 B2
(45) Date of Patent: Feb. 25, 2014

(54) COMPOUNDS COMPRISING 4-BENZOYLPIPERIDINE AS A SIGMA-1-SELECTIVE LIGAND

(75) Inventors: Zhude Tu, Frontenac, MO (US); Robert H. Mach, Eureka, MO (US); Wei Wang, Greenfield, IN (US); Stanley M. Parsons, Santa Barbara, CA (US)

(73) Assignee: Washington University, Saint Louis, MO (US)

( * ) Notice: Subject to any disclaimer, the term of this patent is extended or adjusted under 35 U.S.C. 154(b) by 189 days.

(21) Appl. No.: 13/164,840

(22) Filed: Jun. 21, 2011

(65) Prior Publication Data
US 2011/0311447 A1 Dec. 22, 2011

Related U.S. Application Data

(60) Provisional application No. 61/356,997, filed on Jun. 21, 2010.

(51) Int. Cl.
*A61K 51/00* (2006.01)
*A61M 36/14* (2006.01)

(52) U.S. Cl.
USPC .......... 424/1.89; 424/1.81; 546/187; 546/189

(58) Field of Classification Search
None
See application file for complete search history.

(56) References Cited

U.S. PATENT DOCUMENTS 5,338,852 A * 8/1994 Efange et al. ................. 546/188
7,078,537 B2 7/2006 Choi et al.

OTHER PUBLICATIONS

Tu et al. J Med Chem. 2009, 52, 1358-1369.*
Tu et al. Nucl. Med. Biol. 32 (2005) 423-430.*
Altar, C. A.; Marien, M. R. [3H]vesamicol binding in brain: autoradiographic distribution, pharmacology, and effects of cholinergic lesions. Synapse 1988, 2, 486-493.
Antonini, V.; Prezzavento, O.; Coradazzi, M.; Marrazzo, A.; Ronsisvalle, S.; Arena, E.; Leanza, G. Anti-amnesic properties of (+/—)-PPCC, a novel sigma receptor ligand, on cognitive dysfunction induced by selective cholinergic lesion in rats. J. Neurochem. 2009, 109, 744-754.
Bando, K.; Taguchi, K.; Ginoza, Y.; Naganuma, T.; Tanaka, Y.; Koike, K.; Takatoku, K. Synthesis and evaluation of radiolabeled piperazine derivatives of vesamicol as SPECT agents for cholinergic neurons. Nucl. Med. Biol. 2001, 28, 251-260.
Bem, W.T., et al., "Overexpression of sigma receptors in nonneural human tumors," Cancer Res 51: 6558-6562, 1991.
Colabufo, N. A.; Abate, C.; Contino, M.; Inglese, C.; Niso, M.; Berardi, F.; Perrone, R. PB183, a sigma receptor ligand, as a potential PET probe for the imaging of prostate adenocarcinoma. Bioorg. Med. Chem. Lett. 2008, 18, 1990-1993.
Collier, T. L.; Waterhouse, R. N.; Kassiou, M. Imaging sigma receptors: applications in drug development. Curr. Pharm. Des. 2007, 13, 51-72.
Costantino, L.; Gandolfi, F.; Sorbi, C.; Franchini, S.; Prezzavento, O.; Vittorio, F.; Ronsisvalle, G.; Leonardi, A.; Poggesi, E.; Brasili, L. Synthesis and structure-activity relationships of 1-aralkyl-4-benzylpiperidine and 1-aralkyl-4-benzylpiperazine derivatives as potent σ ligands. J. Med. Chem. 2005, 48, 266-273.
Custers, F. G.; Leysen, J. E.; Stoof, J. C.; Herscheid, J. D. Vesamicol and some of its derivatives: questionable ligands for selectively labelling acetylcholine transporters in rat brain. Eur. J. Pharmacol. 1997, 338, 177-183.
Díaz, J. L.; Zamanillo, D.; Corbera, J.; Baeyens, J. M.; Maldonado, R.; Peràcas, M.; Vela, J. M.; Torrens, A. Selective sigma-1 (sigma(1)) receptor antagonists: emerging target for the treatment of neuropathic pain. Cent. Nerv. Syst. Agents Med. Chem. 2009, 9, 17-183.
Efange, S. M. In vivo imaging of the vesicular acetylcholine transporter and the vesicular monoamine transporter. FASEB J. 2000, 14, 2401-2413.
Efange, S. M. N.; Khare, A. B.; von Hohenberg, K.; Mach, R. H.; Parsons, S. M.; Tu, Z. Synthesis and in vitro biological evaluation of carbonyl group-containing inhibitors of vesicular acetylcholine transporter. J. Med. Chem. 2010, 53, 2825-2835.
Efange, S. M. N.; Mach, R. H.; Smith, C. R.; Khare, A. B.; Foulon, C.; Akella, S. K.; Childers, S. R.; Parsons, S. M. Vesamicol Analogs as Sigma-Ligands—Molecular Determinants of Selectivity at the Vesamicol Receptor. Biochem. Pharmacol. 1995, 49, 791-797.
Gao, M.; Wang, M.; Hutchins, G. D.; Zheng, Q. H. Synthesis of carbon-11-labeled piperidine ring of N-[omega-(6-methoxynaphthalen-1-yl)alkyl] derivatives as new selective PET sigma1 receptor probes. Appl. Radiat. Isot. 2010, 68, 459-465.
Georg, A.; Friedl, A. Identification and characterization of two sigma-like binding sites in the mouse neuroblastoma x rat glioma hybrid cell line NG108-15. J. Pharmacol. Exp. Ther. 1991, 259, 479-483.
Giboureau, N.; Som, I. M.; Boucher-Arnold, A.; Guilloteau, D.; Kassiou, M. PET radioligands for the vesicular acetylcholine transporter (VAChT). Curr. Top. Med. Chem. 2010, 10, 1569-1583.
Hashimoto, K.; Ishiwata, K. Sigma receptor ligands: possible application as therapeutic drugs and as radiopharmaceuticals. Curr. Pharm. Des. 2006, 12, 3857-3876.
Hindmarch, I.; Hashimoto, K. Cognition and depression: the effects of fluvoxamine, a sigma-1 receptor agonist, reconsidered. Hum. Psychopharmaco. 2010, 25, 193-200.
Ishikawa, M.; Sakata, M.; Ishii, K.; Kimura, Y.; Oda, K.; Toyohara, J.; Wu, J.; Ishiwata, K; Iyo, M.; Hashimoto, K. High occupancy of σ1 receptors in the human brain after single oral administration of donepezil: A positron emission tomography study using [11C]SA4503. Int. J. Neuropsychopharmacol. 2009, 12, 1127-1131.

(Continued)

*Primary Examiner* — Michael G Hartley
*Assistant Examiner* — Sean R Donohue
(74) *Attorney, Agent, or Firm* — Saul L. Zackson; Zackson Law LLC

(57) ABSTRACT

Bipiperidinyl compounds and salts thereof are disclosed. The compounds include high affinity ligands for $\sigma_1$ receptors. Some compounds are also highly selective for $\sigma_1$ receptor compared to $\sigma_2$ receptor. Compounds can comprise radioisotopes, including $^{18}F$ or $^{11}C$. Radiolabeled compounds can be used as probes for imaging distribution of $\sigma_1$ receptor in a subject such as a human using positron emission tomography (PET) scanning.

17 Claims, 4 Drawing Sheets

(56) References Cited

OTHER PUBLICATIONS

Ishiwata, K.; Kawamura, K.; Yajima, K.; QingGeLeTu; Mori, H.; Shiba, K. Evaluation of (+)-p-[11C]methylvesamicol for mapping sigma1 receptors: a comparison with [11C]SA4503. Nucl. Med.Biol. 2006, 33, 543-548.

John, C. S.; Bowen, W. D.; Varma, V. M.; McAfee, J. G.; Moody, T. W., Sigma receptors are expressed in human non-small cell lung carcinoma. Life Sci. 1995, 56, 2385-2392.

John, C. S.; Gulden, M. E.; Li, J.; Bowen, W. D.; McAfee, J. G.; Thakur, M. L. Synthesis, in vitro binding, and tissue distribution of radioiodinated 2-[125I]N-(N-benzylpiperidin-4-yl)-2-iodo benzamide, 2-[125I]BP: a potential σ receptor marker for human prostate tumors. Nucl. Med. Biol. 1998, 25, 189-194.

Maestrup, E. G.; Wiese, C.; Schepmann, D.; Hiller, A.; Fischer, S.; Scheunemann, M.; Brust, P.; Wünsch, B. Synthesis of spirocyclic σ1 receptor ligands as potential PET radiotracers, structure-affinity relationships and in vitro metabolic stability. Bioorg.Med. Chem. 2009, 17, 3630-3641.

Matsumoto, R. R. Targeting sigma receptors: Novel medication development for drug abuse and addiction. Expert Rev. Clin. Pharmacol. 2009, 2, 351-358.

Maurice, T.; Su, T.-P. The pharmacology of sigma-1 receptors. Pharmacol. Ther. 2009, 124, 195-206.

Ogawa, K.; Shiba, K.; Akhter, N.; Yoshimoto, M.; Washiyama, K.; Kinuya, S.; Kawai, K.; Mori, H. Evaluation of radioiodinated vesamicol analogs for sigma receptor imaging in tumor and radionuclide receptor therapy. Cancer Sci. 2009, 100, 2188-2192.

Parsons, S. M.; Prior, C.; Marshall, I. G. Acetylcholine transport, storage, and release. Int. Rev. Neurobiol. 1993, 35, 279-390.

Racchi, M.; Mazzucchelli, M.; Porrello, E.; Lanni, C.; Govoni, S. Acetylcholinesterase inhibitors: novel activities of old molecules. Pharmacol. Res. 2004, 50, 441-451.

Rogers, G. A.; Parsons, S. M.; Anderson, D. C.; Nilsson, L. M.; Bahr, B. A.; Kornreich, W. D.; Kaufman, R.; Jacobs, R. S.; Kirtman, B. Synthesis, in vitro acetylcholine-storage-blocking activities, and biological properties of derivatives and analogues of trans-2-(4-phenylpiperidino)cyclohexanol (vesamicol). J. Med. Chem. 1989, 32, 1217-1230.

Roman, G. C. Rivastigmine for subcortical vascular dementia. Expert Rev Neurother 2005, 5, 309-313.

Shiba, K.; Ogawa, K.; Mori, H. In vitro characterization of radioiodinated (+)-2-[4-(4-iodophenyl) piperidino] cyclohexanol [(+)-pIV] as a sigma-1 receptor ligand. Bioorg.Med. Chem. 2005, 13, 1095-1099.

Spruce, B. A. et al., Small molecule antagonists of the σ-1 receptor cause selective release of the death program in tumor and self-reliant cells and inhibit tumor growth in vitro and in vivo. Cancer Res. 2004, 64, 4875-4886.

Tu, Z.; Efange, S. M.; Xu, J.; Li, S.; Jones, L. A.; Parsons, S. M.; Mach, R. H. Synthesis and in vitro and in vivo evaluation of 18F-labeled positron emission tomography (PET) ligands for imaging the vesicular acetylcholine transporter. J. Med. Chem. 2009, 52, 1358-1369.

Vilner, B. J.; John, C. S.; Bowen, W. D. Sigma-1 and sigma-2 receptors are expressed in a wide variety of human and rodent tumor cell lines. Cancer Res. 1995, 55, 408-413.

Vilner, B.J., et al., In: Multiple sigma and PCP receptor ligands: mechanisms for neuromodulation and neuroprotection, Kamenka, J.M., and Domino, E.F., ed, Ann Arbor (Mich), 7 NPP Books, p. 341-353, 1992.

Walker, J.M., et al. "Sigma receptors: biology and function," Pharmacol Rev 42: 355-402 1990.

Waterhouse, R. N. Determination of lipophilicity and its use as a predictor of blood-brain barrier penetration of molecular imaging agents. Mol Imaging Biol 2003, 5, 376-389.

Waterhouse, R. N.; Chang, R. C.; Zhao, J.; Carambot, P. E. In vivo evaluation in rats of [(18)F]1-(2-fluoroethyl)-4-[(4-cyanophenoxy)methyl]piperidine as a potential radiotracer for PET assessment of CNS sigma-1 receptors. Nucl. Med. Biol. 2006, 33, 211-215.

Waterhouse, R. N.; Collier, T. L. In vivo evaluation of [18F]1-(3-fluoropropyl)-4-(4-cyanophenoxymethyl)piperidine: a selective sigma-1 receptor radioligand for PET. Nucl. Med. Biol. 1997, 24, 127-134.

Waterhouse, R. N.; Stabin, M. G.; Page, J. G. Preclinical acute toxicity studies and rodent-based dosimetry estimates of the novel sigma-1 receptor radiotracer [(18)F]FPS. Nucl. Med. Biol. 2003, 30, 555-563.

Zea-Ponce, Y.; Mavel, S.; Assaad, T.; Kruse, S. E.; Parsons, S. M.; Emond, P.; Chalon, S.; Giboureau, N.; Kassiou, M.; Guilloteau, D. Synthesis and in vitro evaluation of new benzovesamicol analogues as potential imaging probes for the vesicular acetylcholine transporter. Bioorg. Med. Chem. 2005, 13, 745-753.

* cited by examiner

US 8,658,131 B2

COMPOUNDS COMPRISING 4-BENZOYLPIPERIDINE AS A SIGMA-1-SELECTIVE LIGAND

CROSS-REFERENCE TO RELATED APPLICATIONS

This application claims the benefit of and priority to U.S. Provisional Application No. 61/356,997, filed on Jun. 21, 2010, which is incorporated herein by reference in its entirety.

GOVERNMENT SUPPORT

Financial support for these studies was provided by the National Institute of Health under NS061025-02, MH092797-01 and MH081281-04.

INTRODUCTION

Sigma receptors are a class of receptors that are expressed in many normal tissues, including liver, kidneys, endocrine glands, and the central nervous system (CNS) (Walker, J. M., et al. Pharmacol Rev 42: 355-402 1990). It has been well established that there are at least two types of sigma receptors, sigma-1 ($\sigma_1$) and sigma-2 ($\sigma_2$) (Walker, J. M., et al. Pharmacol Rev 42, 355-402, 1990). Overexpression of $\sigma_2$ receptors has been reported in a variety of human and murine tumors (Bern, W. T., et al., Cancer Res 51: 6558-6562, 1991; Vilner, B. J., et al., In: Multiple sigma and PCP receptor ligands: mechanisms for neuromodulation and neuroprotection, Kamenka, J. M., and Domino, E. F., ed, Ann Arbor (Mich.), 7 NPP Books, p. 341-353, 1992; Mach, R. H., et al., Cancer Res. 57: 156-161, 1997). The human $\sigma_1$ receptor is a protein of 223 amino acids. $\sigma_1$ receptor is expressed in limbic and motor sturdctures in the brain, and it is believed to modulate various neurotransmitter systems via $Ca^{2+}$-dependent cell signaling cascades. It has been reported that activation of $\sigma_1$ receptors is antidepressive, anxiolytic, neuroprotective, and cognition-enabling.

In the search of highly selective and clinically suitable $\sigma_1$ ligands, investigations have revealed that high affinity $\sigma_1$ ligands must contain a basic amine having two hydrophobic appendages.[6,40] Structure-activity relationship analysis of vesamicol ligands (FIG. 1), which bind to the vesicular acetylcholine transporter (VAChT) in presynaptic cholinergic nerve terminals, found that many vesamicol ligands contain a pharmacophore that also has high affinity for $\sigma_1$ receptors.[41,42] In fact, some of the VAChT ligands show moderate to high binding affinities for $\sigma_1$ receptor. As shown in FIG. 1, (−)-vasamicol (1) has moderate $\sigma_1$ receptor binding affinity values of 73.5 nM, and its methyl substituted derivative (−)-p-methylvesamicol (2) has high $\sigma_1$ receptor binding affinity values of 8.10 nM; the trozamicol analogues meta-iodobenzyltrozamicol (3) and (+)-4-fluorobenzyltrozamicol (4) have $\sigma_1$ receptor binding affinity value of 92 and 21.6 nM respectively.[43] Several carbonyl containing VAChT analogues also bind to $\sigma_1$ very well; for example, (1S,2S)-2-(4-(5-iodothiophen-2-yl)piperidin-1-yl)cyclohexanol (5) has 9.39 nM affinity for $K_i$ value of $\sigma_1$ receptors.[42-49] To identify new, highly selective ligands for $\sigma_1$ receptors, our strategies are to (1) replace the 4-phenylpiperidinyl group in presamicol and trozamicol structures with a 4-substituted benzoylpiperidinyl group which is already known to favor a receptors,[50] (2) alkylate or acylate the secondary amine in (3'-hydroxy-1,4'-bipiperidin-4-yl)(4-substituted phenyl)methanone structurally similar to the presamicol scaffold,[43] and (3) alkylate the secondary amine in (4'-hydroxy-1,3'-bipiperidin-4-yl)(4-substituted phenyl)methanone, which is structurally similar to the trozamicol scaffold.[43] The present inventors identify the ligands that have high affinity for $\sigma_1$ receptors and selectivity for $\sigma_1$ versus $\sigma_2$ receptors. This investigation was inspired by 1) the observation that $\sigma_1$ receptor ligands may be potential therapeutic drugs for the treatment of neurological disorders[3] and cancer[33] and 2) the need for highly selective and potent $\sigma_1$ receptor ligands that can be labeled with F-18 or C-11. Moreover, a novel clinical PET probe for imaging the $\sigma_1$ receptor provides a unique tool to assess the relationship between changes in $\sigma_1$ receptors in the brain during the progression of CNS disorders and provide a useful tool to monitor the treatment efficacy of the CNS disorders and cancer.

SUMMARY

Imaging distribution of $\sigma_1$ receptors, e.g., by Positron Emission Tomography (PET) scanning, can be used diagnostically, e.g., to monitor progression of brain diseases or cancers or therapeutic efficacy of treatments. Furthermore, inhibitors of $\sigma_1$ receptors can be used clinically, e.g., for treatment of brain diseases and cancer in a subject in need of therapy.

The present inventors disclose various bipiperidinyl compounds, and salts thereof. In some aspects, a compound or salt thereof of the present teachings can have activity as a Sigma receptor antagonist or inhibitor, and can show specificity in binding and/or inhibition for Sigma-1 ($\sigma_1$) receptors compared to Sigma-2 ($\sigma_2$) receptors. In some aspects, a compound or salt thereof of the present teachings can have activity as a vesicular acetylcholine transporter (VAChT) antagonist or inhibitor. In various aspects, a compound or salt thereof of the present teachings can serve as a probe for PET scanning.

In various embodiments, a bipiperidinyl compound or salt thereof of the present teachings can comprise a 1,4'-bipiperidin-3'-ol, or a 1,3'-bipiperidin-4'-ol. In various embodiments, a compound or salt thereof of the present teachings can exhibit a $K_i$ for a $\sigma_1$ receptor of $K_i$<5 nM. In some embodiments, a compound or salt thereof of the present teachings can exhibit selectivity for $\sigma_1$ versus $\sigma_2$ receptors, e.g., $\sigma_1/\sigma_2$>1000-fold. In some embodiments, a compound or salt thereof can exhibit low potentcy for VAChT, e.g. $K_i$>1000 nM. In some embodiments, a compound or salt thereof can exhibit selectivity for $\sigma_1$ versus VAChT, e.g., $\sigma_1$/VAChT>1000-fold.

In some aspects, a compound or salt thereof of the present teachings can comprise a positron-emitting isotope, such as, for example, a positron-emitting isotope of fluorine, such as $^{18}F$, or a positron-emitting isotope of carbon, such as $^{11}C$. In some aspects, a compound or salt thereof of the present teachings can be used as a tracer for PET scanning.

In an embodiment, a compound or salt thereof of the present teachings can be 14a of structure

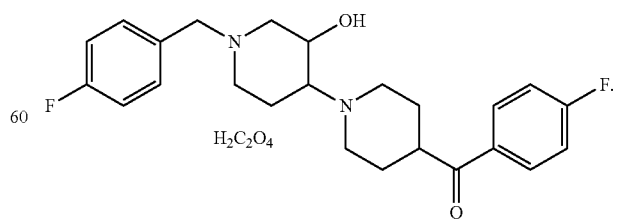

In some aspects, $H_2C_2O_4$ can be oxalic acid. In some aspects, 14a can exhibit subnanomolar $\sigma_1$ affinity, such as a $K_i$ of 0.48 nM. In various aspects, 14a can exhibit a selectivity for $\sigma_1$ versus $\sigma_2$ of about 1360-fold, and selectivity of about 3600-fold for $\sigma_1$ versus VAChT.

In some aspects, a compound of the present teachings can have a structure

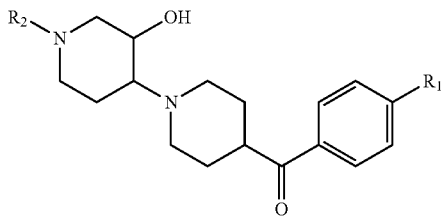

wherein $R_1$ can be F or methoxy, $R_2$ can be

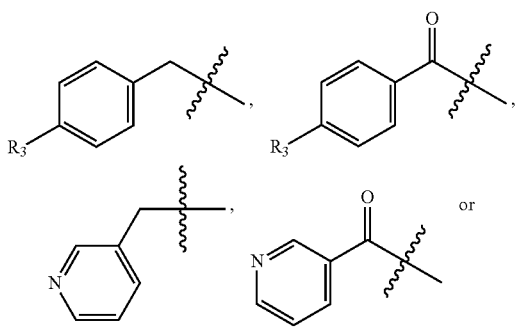 or 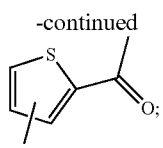

$R_3$ can be F or methoxy. In various configurations, an F can be an $^{18}$F, and a methoxy can comprise a $^{11}$C. In various configurations, in a structure of the present teachings comprising more than one fluorine atom, one or more fluorine atoms can be an $^{18}$F. In various configurations, in a structure of the present teachings comprising more than one methoxy group, one or more carbon atoms of a methoxy group can be a $^{11}$C.

The moderate to high affinity of vesamicol and many of its analogues for σ1 and σ2 receptors reduces the selectivity of these compounds for the VAChT and potentially compromises their utility as VAChT ligands. Consequently, we also screened the target compounds for sigma binding to identify selective VAChT ligands from this new structural class of agents. Among the compounds tested, there was wide variability in affinity for $\sigma_1$ or $\sigma_2$ receptors; only one compound (TZ-3-156) displayed high affinity for σ1 receptors (Ki=13.23±0.48 nm), while all other compounds exhibited poor affinity for σ receptors.

In various aspects, a structure of the present teachings can be a structure set forth herein. Table 1 sets forth $K_i$ and Log P values for disclosed structures with respect to $\sigma_1$, $\sigma_2$ and VAChT. Table 2 sets forth elemental analysis of analogues of disclosed structures. Table 3 sets forth structures of VAChT specific compounds. Table 4 sets forth $K_i$ values of VAChT specific compounds.

TABLE 1

Affinities of new analogues for $\sigma_1$ receptor, $\sigma_2$ receptor, and VAChT. [a]

| Compound | $\sigma_1$ ($K_i$, nM) [b] | $\sigma_2$ ($K_i$, nM) [c] | VAChT ($K_i$, nM) [d] | $\sigma_1/\sigma_2$ selectivity | $\sigma_1$/VAChT selectivity | LogP [e] |
|---|---|---|---|---|---|---|
| 14a | 0.48 ± 0.14 | 1741 ± 286 | 1360 ± 295 | 3627 | 2833 | 2.83 |
| 14b | 4.03 ± 0.47 | 5521 ± 1352 | 3310 ± 907 | 1370 | 821 | 2.61 |
| 14c | 1.36 ± 0.28 | 2301 ± 249 | 401 ± 42.0 | 1692 | 295 | 2.73 |
| 14d | 22.8 ± 2.32 | 4208 ± 115 | 2030 ± 385 | 184 | 89 | 1.48 |
| 14e | 2.51 ± 0.34 | 2788 ± 718 | 294 ± 16.1 | 1111 | 117 | 2.82 |
| 14f | 25.9 ± 0.96 | 5157 ± 202 | 14800 ± 3460 | 199 | 569 | 2.61 |
| 14g | 4.05 ± 0.88 | 3033 ± 248 | 44.2 ± 3.03 | 749 | 11 | 2.72 |
| 14h | 59.64 ± 2.22 | 4540 ± 1606 | 137 ± 14.3 | 76 | 2.2 | 1.46 |
| 15a | 3144 ± 140 | 8642 ± 812 | 3600 ± 499 | 2.7 | 1.1 | 1.92 |
| 15b | 2238 ± 271 | >10000 | 30900 ± 6400 | >4.5 | 14 | 2.25 |
| 15c | 2833 ± 374 | 20450 ± 4887 | 683 ± 90 | 7.2 | 0.24 | 1.67 |
| 15d | 7739 ± 662 | 13565 ± 1435 | 3340 ± 706 | 1.7 | 0.43 | 0.57 |
| 15g | 2088 ± 154 | 32850 ± 443 | 3460 ± 476 | 15.7 | 1.66 | 1.90 |
| 15h | 2061 ± 113 | 15862 ± 3045 | 555 ± 65.4 | 7.7 | 0.27 | 1.65 |
| 15i | 26646 ± 8738 | 17041 ± 8626 | 372 ± 65.7 | 0.64 | 0.01 | 0.56 |
| 16a | 50.0 ± 7.9 | 3443 ± 928 | 136 ± 13.8 | 69 | 2.72 | 1.98 |
| 16b | 91.1 ± 19.9 | 4979 ± 507 | 1970 ± 196 | 54 | 22 | 1.73 |
| 16c | 106 ± 28 | 832 ± 147 | 149 ± 22.5 | 7.8 | 1.4 | 1.88 |
| 16d | 1159 ± 128 | 13018 ± 2626 | 237 ± 41.4 | 11 | 0.20 | 0.79 |
| 16e | 137 ± 21 | 5598 ± 1033 | 48.6 ± 8.37 | 41 | 0.35 | 2.00 |
| 16f | 297 ± 27 | 4208 ± 439 | 1080 ± 296 | 14 | 3.6 | 1.75 |
| 16g | 208 ± 53 | 8539 ± 1900 | 35.5 ± 11.1 | 41 | 0.17 | 1.89 |
| 16h | 2225 ± 168 | 17135 ± 3863 | 107 ± 11 | 7.7 | 0.40 | 0.80 |

[a] $K_i$ values (mean ± SEM) were determined in at least three experiments.
[b] The $\sigma_1$ binding assay used membrane preparations of guinea pig brain.
[c] The $\sigma_2$ binding assay used homogenates of rat liver.
[d] The VAChT binding assay used expressed human VAChT.
[e] Calculated value at pH 7.4 by ACD/I-Lab, version 7.0. (Advanced Chemistry Development, Inc., Canada).

TABLE 2

Elemental Analysis of Analogues

| Compound | Molecular Formula | Calculated C | Calculated H | Calculated N | Found C | Found H | Found N |
|---|---|---|---|---|---|---|---|
| 14a | $C_{24}H_{28}F_2N_2O_2 \cdot H_2C_2O_4 \cdot 0.25H_2O$ | 61.35 | 6.04 | 5.50 | 61.43 | 5.91 | 5.54 |
| 14b | $C_{25}H_{31}FN_2O_3 \cdot H_2C_2O_4 \cdot 0.5H_2O$ | 61.70 | 6.52 | 5.33 | 62.09 | 6.41 | 5.30 |
| 14c | $C_{24}H_{29}FN_2O_2 \cdot H_2C_2O_4 \cdot 0.25H_2O$ | 63.60 | 6.47 | 5.70 | 63.52 | 6.47 | 5.67 |
| 14d | $C_{23}H_{28}FN_3O_2 \cdot 1.5H_2C_2O_4 \cdot H_2O$ | 56.72 | 6.04 | 7.63 | 56.88 | 5.93 | 7.31 |
| 14e | $C_{25}H_{31}FN_2O_3 \cdot H_2C_2O_4 \cdot 0.5H_2O$ | 61.70 | 6.52 | 5.33 | 61.56 | 6.28 | 5.24 |
| 14f | $C_{25}H_{31}FN_2O_3 \cdot H_2C_2O_4 \cdot 0.5H_2O$ | 62.56 | 6.94 | 5.21 | 62.42 | 6.78 | 5.19 |
| 14g | $C_{25}H_{32}N_2O_3 \cdot 2H_2C_2O_4$ | 65.04 | 6.87 | 5.62 | 64.58 | 6.72 | 5.56 |
| 14h | $C_{24}H_{31}N_3O_3 \cdot 2H_2C_2O_4 \cdot 0.5H_2O$ | 56.18 | 6.06 | 7.02 | 56.37 | 5.98 | 6.82 |
| 15a | $C_{24}H_{26}F_2N_2O_5 \cdot H_2C_2O_4$ | 60.23 | 5.44 | 5.40 | 59.96 | 5.43 | 5.37 |
| 15b | $C_{24}H_{27}FN_2O_3 \cdot H_2C_2O_4 \cdot 0.5H_2O$ | 60.10 | 5.98 | 5.19 | 59.99 | 6.07 | 5.14 |
| 15c | $C_{24}H_{27}FN_2O_3 \cdot H_2C_2O_4 \cdot H_2O$ | 60.22 | 6.03 | 5.40 | 60.72 | 5.98 | 5.50 |
| 15d | $C_{23}H_{26}FN_3O_3 \cdot H_2C_2O_4 \cdot 0.25H_2O$ | 59.34 | 5.61 | 8.30 | 59.25 | 5.55 | 8.26 |
| 15e | $C_{25}H_{29}FN_2O_4 \cdot H_2C_2O_4$ | 61.12 | 5.89 | 5.28 | 61.03 | 5.92 | 5.26 |
| 15f | $C_{25}H_{30}N_2O_8 \cdot H_2C_2O_4 \cdot 1.5H_2O$ | 60.10 | 6.54 | 5.19 | 60.47 | 6.39 | 5.41 |
| 15g | $C_{24}H_{29}N_3O_4 \cdot H_2C_2O_4$ | 60.81 | 6.08 | 8.18 | 60.57 | 6.06 | 7.96 |
| 16a | $C_{24}H_{28}F_2N_2O_2 \cdot H_2C_2O_4$ | 61.90 | 5.99 | 5.55 | 61.78 | 5.97 | 5.52 |
| 16b | $C_{25}H_{31}FN_2O_3 \cdot H_2C_2O_4$ | 62.78 | 6.44 | 5.42 | 62.61 | 6.32 | 5.40 |
| 16c | $C_{24}H_{29}FN_2O_2 \cdot H_2C_2O_4$ | 64.18 | 6.42 | 5.76 | 63.95 | 6.40 | 5.71 |
| 16d | $C_{23}H_{28}FN_3O_2 \cdot H_2C_2O_4 \cdot 0.5H_2O$ | 60.47 | 6.29 | 8.46 | 60.59 | 6.29 | 8.41 |
| 16e | $C_{25}H_{31}FN_2O_3 \cdot H_2C_2O_4$ | 52.78 | 6.44 | 5.42 | 62.55 | 6.49 | 5.46 |
| 16f | $C_{26}H_{34}N_2O_4 \cdot H_2C_2O_4$ | 63.62 | 6.86 | 5.30 | 63.33 | 6.87 | 5.27 |
| 16g | $C_{25}H_{32}N_2O_3 \cdot H_2C_2O_4 \cdot 0.5H_2O$ | 63.89 | 6.95 | 5.52 | 63.93 | 6.85 | 5.51 |
| 16h | $C_{24}H_{31}N_3O_3 \cdot H_2C_2O_4$ | 62.51 | 6.66 | 8.41 | 62.14 | 6.72 | 8.27 |

TABLE 3

Structures of VAChT specific compounds

| Name | # | Structure |
|---|---|---|
| WW-1-35 | 1 | 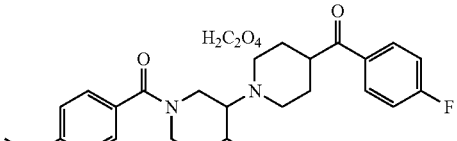 WW-1-35 |
| WW-1-39 | 2 | 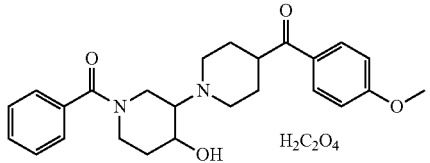 WW-1-39 |
| WW-1-47 | 3 | 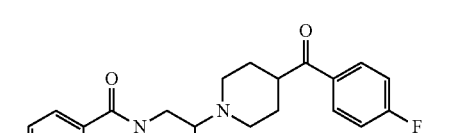 WW-1-47 |

TABLE 3-continued

Structures of VAChT specific compounds

| Name | # | Structure |
|---|---|---|
| WW-1-67 | 4 | 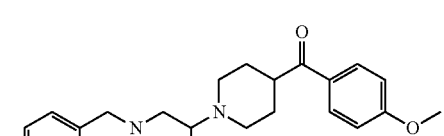 WW-1-67 |
| WW-1-71 | 5 | 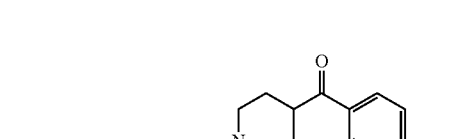 WW-1-71 |
| WW-1-109 | 6 | 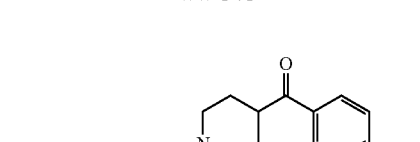 WW-1-109 |

TABLE 3-continued

Structures of VAChT specific compounds

| Name | # | Structure |
|---|---|---|
| WW-1-107 | 7 | WW-1-107 |
| WW-1-117 | 8 | WW-1-117 |
| WW-1-123 | 9 | WW-1-123 |
| WW-1-127 | 10 | WW-1-127 |
| WW-1-88-1 | 11 | WW-I-88-1  (+)-isomer |
| WW-1-88-2 | 12 | WW-I-88-2  (−)-isomer |
| WW-III-10 | 13 | |
| WW-III-13 | 14 | |
| WW-III-17 | 15 | |
| WW-III-21 | 15 | |
| WW-III-25 | 16 | WW-III-25 |
| WW-III-39 | 17 | WW-III-39 |
| WW-III-41 | 18 | WW-III-41 |
| WW-III-43 | 19 | WW-III-43 |

TABLE 3-continued

Structures of VAChT specific compounds

| Name | # | Structure |
|---|---|---|
| WW-III-45 | 20 | WW-III-45 |
| WW-III-47 | 21 | WW-III-47 |
| DZT-I-137 | 22 | 0.5H₂C₂O₄ |
| DZT-I-107 | 23 | 0.5H₂C₂O₄ |
| OS-5-40 | 24 | OS-5-40 |
| OS-5-60 | 25 | OS-5-60 |
| OS-5-70 | 26 | OS-5-70 |
| OS-5-72-1 | 27 | OS-5-72-1 |
| OS-5-72-2 | 28 | OS-5-72-2<br>$C_{25}H_{31}N_3O_{10}$<br>MW: 533.53 |
| OS-5-82 | 29 | OS-5-82 |
| OS-5-88 | 30 | OS-5-88 |
| OS-5-110 | 31 | |

TABLE 4

Ki values of VAChT specific compounds

| Name | # | Formula (MW) | Sigma-1 $\sigma_1$ (nM) | Sigma-2 $\sigma_1$ (nM) | VAChT (nM) | Log P |
|---|---|---|---|---|---|---|
| WW-1-35 | 1 | $C_{27}H_{31}FN_2O_8$ 530.54 | 661 ± 72 | >10000 nM | 13000 ± 1900 | 2.25 |
| WW-1-39 | 2 | $C_{26}H_{29}FN_2O_7 + H_2O$ 518.53 | 37885 ± 271 | 3946 ± 278 | 62.7 ± 14.3 | 1.75 |
| WW-1-47 | 3 | $C_{26}H_{30}F_2N_2O_6$ 504.52 | 50 ± 7.9 | 3443 ± 928 | 136 ± 13.8 | 1.98 |
| WW-1-67 | 4 | $C_{27}H_{32}N_2O_8 + H_2O$ 530.54 | 5760 ± 477 | 4847 ± 649 | 15.4 ± 0.94 | 1.73 |
| WW-1-71 | 5 | $C_{27}H_{33}FN_2O_7$ 516.56 | 137 ± 21 | 5598 ± 1033 | 48.6 ± 8.37 | 2.00 |
| WW-1-109 | 6 | $C_{27}H_{34}N_2O_7 + 0.5H_2O$ 507.58 | 208 ± 53 | 8539 ± 1900 | 35.5 ± 11.1 | 1.89 |
| WW-1-107 | 7 | $C_{27}H_{31}FN_2O_8 + 1.5H_2O$ 557.56 | 11932 ± 5613 | 2597 ± 363 | 233 ± 36.8 | 1.98 |
| WW-1-117 | 8 | $C_{26}H_{31}FN_2O_6$ 486.53 | 106 ± 28 | 832 ± 147 | 149 ± 22.5 | 1.88 |
| WW-1-123 | 9 | $C_{26}H_{28}F_2N_2O_7 + 0.5H_2O$ 527.51 | 3119 ± 360 | 1375 ± 135 | 8700 ± 1620 | 2.00 |
| WW-1-127 | 10 | $C_{27}H_{33}FN_2O_7$ 516.56 | 91.1 ± 19.9 | 4979 ± 507 | 1970 ± 196 | 1.73 |
| WW-1-88-1 | 11 | $C_{24}H_{27}FN_2O_6 + H_2O$ 476.49 | 3693 ± 537 | 14717 ± 1936 | 366 ± 36.0 | 2.06 |
| WW-1-88-2 | 12 | $C_{26}H_{29}FN_2O_{10} + 1.25H_2O$ 571.03 | 3553 ± 438 | 6889 ± 546 | 20.9 ± 4.98 | 2.06 |
| WW-III-10 | 13 | $C_{28}H_{36}N_2O_8$ | 297.41 ± 27.22 | 4207.71 ± 439.10 | 1080 ± 296 | 1.75 |
| WW-III-13 | 14 | $C_{26}H_{31}N_3O_8 + 1.5H_2O$ | 8601.17 ± 375.62 | 24270.32 ± 1910.12 | 112 ± 12.9 | 0.65 |
| WW-III-17 | | $C_{26}H_{32}N_2O_8S + 0.5H_2O$ | 39396.39 ± 4099.55 | 24439.19 ± 3627.47 | 142 ± 16.4 | 2.51 |
| WW-III-21 | 15 | $C_{25}H_{30}N_2O_8S + 0.5H_2O$ | 33960.81 ± 6118.62 | 6377.96 ± 1002.53 | 19.0 ± 2.12 | 2.05 |
| WW-III-25 | 16 | $C_{26}H_{33}N_3O_7$ | 2225.99 ± 167.98 | 17135.24 ± 3863.84 | 107 ± 11.1 | 0.8 |
| WW-III-39 | 17 | $C_{25}H_{29}FN_2O_7S + 0.25H_2O$ | 12125.27 ± 2447.43 | 4219.28 ± 204.70 | 11.4 ± 3.67 | 2.53 |
| WW-III-41 | 18 | $C_{25}H_{29}FN_2O_7S$ | 2800.43 ± 210.38 | 16418.19 ± 1479.77 | 1190 ± 137 | 2.53 |
| WW-III-43 | 19 | $C_{24}H_{27}FN_2O_7S + H_2O$ | 22509.06 ± 5877.28 | 4046.14 ± 244.35 | 123 ± 14.9 | 2.07 |
| WW-III-45 | 20 | $C_{25}H_{28}FN_3O_7 + H_2O$ | 13796.39 ± 2628.81 | 15496.51 ± 2172.13 | 807 ± 139 | 0.66 |
| WW-III-47 | 21 | $C_{25}H_{30}FN_3O_6 + 0.5H_2O$ | 1159.95 ± 128.12 | 13018.08 ± 2626.50 | 237 ± 41.4 | 0.79 |
| DZT-I-137 | 22 | $C_{25}H_{28}FN_2O_5$ 443.20 | 2122.26 ± 49.01 | 1859.79 ± 144.36 | 38 ± 3.84 | 2.87 |
| DZT-I-107 | 23 | $C_{24}H_{28}NO_5$ 410.20 | 132.00 ± 10.10 | 1952.95 ± 13.12 | 4.64 ± 0.47 | 2.94 |
| OS-5-40 | 24 | $C_{26}H_{30}N_2O_{10}$ MW: 530.52 | 2115 ± 289 | 3771 ± 886 | 27.9 ± 7.99 | 2.29 |
| OS-5-60 | 25 | $C_{23}H_{28}N_2O_6$ MW: 428.48 | 1302 ± 93 | 2553 ± 339 | 18.4 ± 2.54 | 1.42 |
| OS-5-70 | 26 | $C_{26}H_{31}N_3O_{10}$ MW: 545.54 | 11362 ± 2040 | 27525 ± 6943 | 48.0 ± 11.4 | 1.33 |
| OS-5-72-1 | 27 | $C_{25}H_{31}N_3O_{10}$ MW: 533.53 | 9237 ± 793 | 11396 ± 2500 | 38.7 ± 6.95 38.7 ± 6.95 | 0.53 |
| OS-5-72-2 | 28 | $C_{25}H_{31}N_3O_{10}$ MW: 533.53 | 7664 ± 233 | 6987 ± 1482 | 2310 ± 393 | 0.48 |
| OS-5-82 | 29 | $C_{26}H_{31}N_3O_{11}$ MW: 561.54 | 5682 ± 26 | 10813 ± 1282 | 23.3 ± 3.43 | 1.66 |
| OS-5-88 | 30 | $C_{24}H_{28}N_2O_7$ MW: 456.49 | 986 ± 160 | 2572 ± 139 | 8.36 ± 0.68 | 2.64 |
| OS-5-110 | 31 | $C_{25}H_{29}N_3O_{10}$ MW: 531.51 | 20346 ± 8133 | 5078 ± 221 | 2.2 | 0.87 |

Structures of the present teachings can be synthesized using standard methods of organic synthesis following well known principles such as set forth in Tu, Z., et al., J. Med. Chem. 52: 1358-1369, 2009; Efange, S. M. N., et al., J. Med. Chem. 53: 2825-2835, 2006; Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004. Methods of imaging using PET scanning are set forth in references such as Curati, W. L., Imaging in Oncology, Cambridge University Press, Cambridge, U.K., 1998; and Welch, M. J., and Redvanly, C. S., eds. Handbook of Radiopharmaceuticals: Radiochemistry and Applications, J. Wiley, N.Y., 2003.

The present inventors synthesized ((3'R,4'R)-1'-(4-fluorobenzyl)-3'-hydroxy-1,4'-bipiperidin-4-yl)(4-[$^{11}$C]methoxyphenyl)methanone (14e), which has high affinity for σ1 receptors (Ki=2.51±0.34 nM, σ1/σ2>1100-fold, log P=2.82) and can be labeled with either C-11 or F-18.

DETAILED DESCRIPTION

Figure 1:
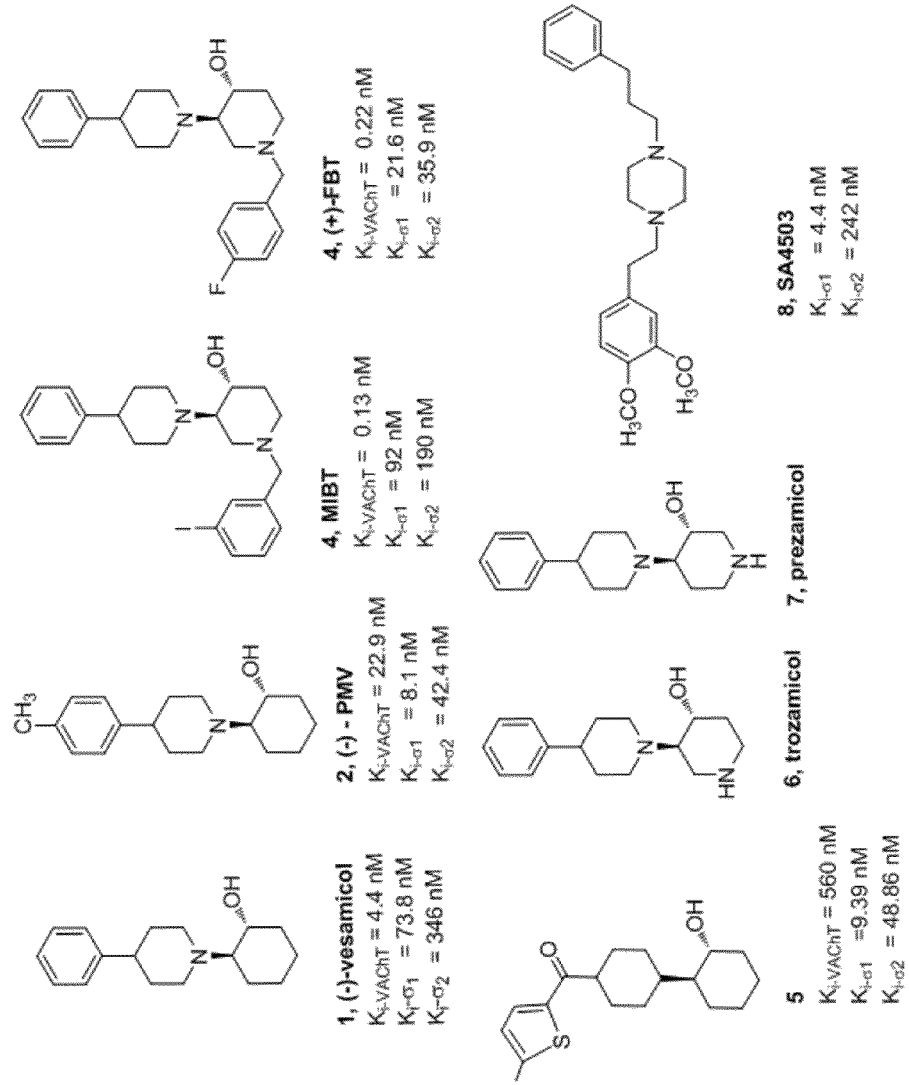
FIG. 1 illustrates prior art vesamicol ligands which bind to the vesicular acetylcholine transporter (VAChT) in presynaptic cholinergic nerve terminals.

The present inventors have synthesized a new class of compounds targeting $\sigma_1$ receptors. The inventors explored carbonyl-containing VAChT inhibitors by introducing substituted benzyl or benzoyl groups on the nitrogen of the terminal piperidine ring.

The present inventors have developed five racemic compounds, 14a (0.48 nM), 14b (4.03 nM), 14c (1.36 nM), 14e (2.51 nM), and 14g (4.05 nM), that have very high binding affinities for $\sigma_1$ receptors. The first four compounds also display high selectivity for $\sigma_1$ vs. $\sigma_2$ receptors and do not bind well to VAChT. They can be useful pharmacological agents targeting $\sigma_1$ receptors. Fluorine-18 or carbon-11 isotopes can be introduced into these compounds and can be used as PET probes PET probes for imaging $\sigma_1$ receptors in human beings and animals. Particularly for 14a and 14c, the $\sigma_1/\sigma_2$ ratios are greater than 3600 and 1600 fold and the $\sigma_1$/VAChT ratios are greater than 2800 fold and 290 fold, respectively. The fluorine-18 or carbon-11 versions of 14a and 14c can be used to quantify the density of $\sigma_1$ receptors in human beings or animals. In addition, the SAR information from the current study provides new insight into $\sigma_1$ receptor ligands.

Abbreviations List:

Anal., Analysis; BOP-Cl, bis(2-oxo-3-oxazolidinyl)phosphonic chloride; Calcd., calculated; CIMS., Chemical ionization mass spectrometry; CNS, central nervous system; SAR, structure-activity relationship; DCC, N,N'-dicyclohexylcarbodiimide; DMF, N,N-dimethylformamide; DMSO, dimethyl sulfoxide; DTG, 1,3-ditolylguanidine; ND, not determined; PET, positron emission tomography; prezamicol: 3-hydroxy-4-(4-phenylpiperidinyl)piperidine; SPECT, single photon emission computed tomography; THF, tetrahydrofuran; TLC, thin layer chromatography; trozamicol, 4-hydroxy-3-(4-phenylpiperidinyl)piperidine; VAChT, vesicular acetylcholine transporter; vesamicol, (−)-trans-2-(4-phenylpiperidino)cyclohexanol.

Experimental Section

General.

All reagents and chemicals were purchased from commercial suppliers and used without further purification unless otherwise stated. All anhydrous reactions were carried out in an oven-dried glassware under nitrogen unless otherwise stated. Flash column chromatography was conducted using silica gel 60A, "40 Micron Flash" [32-63 µm] (Scientific Absorbents, Inc.); the mobile phase used is reported in the experimental procedure for each compound. Melting points were determined using the MEL-TEMP 3.0 apparatus (Laboratory Devices Inc.) and are uncorrected. $^1$H NMR spectra were recorded at 300 MHz on a Mercury-VX spectrometer (Varian, Inc.) with CDCl$_3$ as solvent and tetramethylsilane (TMS) as the internal standard unless otherwise stated. All chemical shift values are reported in parts per million (PPM) ($\delta$). Peak multiplicities are singlet, s; doublet, d; triplet t; multiplet, m; broad, br. Elemental analyses (C, H, N) were determined by Atlantic Microlab, Inc. Elemental analysis was used to determine the purity of the target compounds that were assessed with biological data. All the compounds reported in the manuscript have a purity of ≥95%.

(5,6-Dihydropyridin-1(2H)-yl)(phenyl)methanone (10)

Into a solution of 1,2,3,6-tetrahydropyridine (1.00 g, 12.0 mmol) and triethylamine (3 mL) in CH$_2$Cl$_2$ (30 mL), benzoyl chloride (1.69 g, 12.0 mmol) was added dropwise at 0° C. The reaction mixture was stirred at room temperature for 2 hrs and washed with saturated Na$_2$CO$_3$ (20 mL×3) and brine solution (20 mL), dried over Na2SO$_4$ and concentrated under vacuum to afford crude product. The crude product was purified by silica gel column chromatography using hexane/ethyl acetate (10/3, v/v) to afford target product as a colorless oil (2.27 g, 100%). $^1$H NMR (CDCl$_3$): $\delta$ 2.16-2.25 (m, 2H), 3.46-4.20 (m, 4H), 5.53-5.91 (m, 2H), 7.29-7.53 (m, 5H).

7-Oxa-3-azabicyclo[4.1.0]heptan-3-yl(phenyl)methanone (11)

Into a solution of 10 (2.27 g, 12.1 mmol) in CH$_2$Cl$_2$ (20 mL), a solution of 3-chloroperoxybenzoic acid (5.43 g, 77% pure, 24.3 mmol) in CH$_2$Cl$_2$ (40 mL) was added dropwise at 0° C. The reaction mixture was stirred at room temperature for 5 hrs. After the reaction was complete as determined by TLC (hexane/ethyl acetate, 1/1, v/v), saturated Na$_2$CO$_3$ solution (50 mL) was added into the reaction vial slowly with stirring. The reaction mixture was stirred for 30 min. The organic layer was washed with saturated Na$_2$CO$_3$ solution (50 mL×3), brine solution (50 mL), dried over Na$_2$SO$_4$ and concentrated under reduced pressure. The crude product was purified by silica gel column chromatograph using hexane/ethyl acetate (3/1, v/v) as the mobile phase to afford the product as a sticky oil (1.54 g, 62%). $^1$H NMR (CDCl$_3$): $\delta$ 2.04-2.18 (m, 2H), 3.09-4.40 (m, 6H), 7.28-7.47 (m, 5H).

Procedure A: General Method for Preparing 1'-Substituted Benzoyl-4-acyl-[1,4'-bipiperidin]-3'-yl Acetate (12a and 12c) or 1'-Substituted Benzoyl-4-acyl-[1,3'-bipiperidin]-4'-yl Acetate (12b and 12d)

1'-Benzoyl-4-(4-fluorobenzoyl)-[1,4'-bipiperidin]-3'-yl acetate (12a) and 1'-benzoyl-4-(4-methoxybenzoyl)-1,3'-bipiperidin-4'-yl acetate (12b)

A mixture of 11 (0.50 g, 1.97 mmol), 4-(4-fluorobenzoyl) piperidine hydrochloride (1.20 g, 4.92 mmol), triethylamine (1 mL) and sodium carbonate (2.12 g, 20.0 mmol) in ethanol (50 mL) was heated to 70° C. with stirring for over 24 hrs. The reaction mixture was cooled, filtered and concentrated under reduced pressure. The crude product was dissolved in CH$_2$Cl$_2$ (50 mL) and washed with water (50 mL), saturated Na$_2$CO$_3$ (50 mL) and brine solution. The organic layer was dried over Na$_2$SO$_4$ and concentrated under reduced pressure to afford crude product as an oil. Acetic anhydride (1.11 g, 10.92 mmol) was added into a solution of this crude product in CH$_2$Cl$_2$ (30 mL). The reaction mixture was stirred at room temperature overnight. The mixture was washed with saturated Na$_2$CO$_3$ (30 mL×3) and brine solution. The organic layer was dried over Na$_2$SO$_4$ and concentrated under reduced pressure. The crude product was purified by silica gel column chromatography using ethyl acetate/hexane (2/1, v/v) as the mobile phase to afford 12a (0.41 g, 37%), the first eluted compound as a colorless oil. $^1$H NMR (CDCl$_3$): $\delta$: 1.40-1.74 (m, 3H), 2.04 (s, 3H), 2.30-2.37 (m, 1H), 2.51-2.69 (m, 2H), 2.86-3.21 (m, 6H), 4.30-4.70 (m, 1H), 4.80-5.10 (br s, 1H), 7.10-7.16 (t, J=5.7 Hz, 2H), 7.40-7.41 (m, 5H), 7.93-7.97 (m, 2H), At the same time, 1'-benzoyl-4-(4-fluorobenzoyl)-[1,3'-bipiperidin]-4'-yl acetate (12b) (0.50 g, 45%) was eluted as the second compound and 12b was a colorless oil. $^1$H NMR (CDCl$_3$): $\delta$ 1.50-1.90 (m, 3H), 2.07 (s, 3H), 2.81-3.29 (m, 6H), 2.20-2.80 (m, 4H), 3.50-4.00 (m, 2H), 4.64 (br s, 1H), 5.10-5.18 (m, 1H), 7.12 (t, J=5.7 Hz, 2H), 7.41-7.42 (m, 5H), 7.93 (m, 2H).

1'-Benzoyl-4-(4-methoxybenzoyl)-[1,4'-bipiperidin]-3'-yl acetate (12c) and 1'-benzoyl-4-(4-methoxybenzoyl)-1,3'-bipiperidin-4'-yl acetate (12d)

Procedure A was followed to prepare 12c (0.42 g, 37%) as a colorless oil that was eluted first and 12d (0.34 g, 37%) as a colorless oil that was eluted second. The $^1$H NMR of 12c (CDCl$_3$): δ 1.40-1.90 (m, 8H), 2.04 (s, 3H), 2.22-2.40 (m, 1H), 2.24-2.70 (m, 2), 2.80-3.22 (m, 4H), 3.87 (s, 3H), 4.00-4.60 (m, 1H), 6.94 (d, J=8.7 Hz, 2H), 7.41 (s, 5H), 7.91 (d, J=8.7 Hz, 2H). The $^1$H NMR of 12d (CDCl$_3$): δ 1.45-1.90 (m, 7H), 2.04 (s, 3H), 2.22-2.75 (m, 2H), 2.80-3.30 (m, 5H), 3.64 (br s, 1H), 3.86 (s, 3H), 4.64 (br s, 1H), 5.10-5.20 (m, 1H), 6.92 (d, J=8.1 Hz, 2H), 7.64 (br s, 5H), 7.89 (m, 2H).

Procedure B. General Method for Preparing (3'-Hydroxy-[1,4'-bipiperidin]-4-yl)(4-Substituted-phenyl)Methanone (13a and 13c) and (4'-Hydroxy-[1,3'-bipiperidin]-4-yl)(4-Substituted-phenyl)Methanone (13b and 13d)

(4-Fluorophenyl)(3'-hydroxy-[1,4'-bipiperidin]-4-yl)methanone (13a)

To a solution of 12a (0.27 g, 0.66 mmol) in ethanol (10 mL), 6N HCl (4 mL, 2.40 mmol) was added. The reaction mixture was heated to reflux for 14 hours. The mixture was cooled and concentrated under vacuum. 1N NaOH solution (20 mL) was added to the residue, the aqueous phase was extracted with CH$_2$Cl$_2$ (20 mL×3). The combined organic phases were washed with saturated sodium carbonate (20 mL×3) and brine solution, dried over Na$_2$SO$_4$ and concentrated under vacuum. The crude product was purified by silica gel column chromatography using methanol/ethyl acetate/triethylamine (50/50/2, v/v/v) as the mobile phase to afford 13a as a colorless oil (132 mg, 66%). $^1$H NMR (CDCl$_3$): δ 1.37-1.89 (m, 8H), 2.24-2.77 (m, 6H), 2.98-3.01 (m, 1H), 3.12-3.24 (m, 2H), 3.35-3.51 (m, 2H), 7.11-7.17 (t, J=5.7 Hz, 2H), 7.94-7.99 (m, 2H).

(3'-Hydroxy-[1,4'-bipiperidin]-4-yl)(4-methoxyphenyl)methanone (13b)

Procedure B was used to prepare 13b as a colorless oil (173 mg, 76%). $^1$H NMR (CDCl$_3$+CD$_3$OD): δ 1.56-1.92 (m, 7H), 2.41-3.47 (m, 11H), 3.62-3.70 (m, 1H), 3.87 (s, 3H), 6.99-7.02 (m, 2H), 7.94-7.98 (m, 2H).

(1'-Benzoyl-4'-hydroxy-[1,3'-bipiperidin]-4-yl)(4-fluorophenyl)methanone (13c)

Procedure B was followed to afford 13c as a colorless oil (0.22 g, 67%). NMR (CDCl$_3$+CD$_3$OD): δ 1.43-1.51 (m, 1H), 1.74-1.90 (m, 5H), 2.10-2.12 (m, 1H), 2.29-2.40 (m, 2H), 2.49-2.61 (m, 2H), 2.77-2.88 (m, 2H), 3.03-3.06 (m, 2H), 3.17-3.26 (m, 2H), 3.51-3.59 (m, 1H), 7.14 (t, J=5.4 Hz, 2H), 7.94-7.98 (m, 2H).

(1'-Benzoyl-4'-hydroxy-[1,3'-bipiperidin]-4-yl)(4-methoxyphenyl)methanone (13d)

Procedure B was followed to afford 13d as a colorless oil (0.18 g, 82%). $^1$HNMR (CDCl$_3$+CD$_3$OD): δ 1.56-1.92 (m, 6H), 2.07-2.11 (m, 1H), 2.41-2.80 (m, 5H), 2.80-3.00 (m, 1H), 3.00-3.18 (m, 2H), 3.20-3.40 (m, 2H), 3.62-3.70 (m, 1H), 3.87 (s, 3H), 6.99-7.02 (m, 2H), 7.94-7.98 (m, 2H).

Procedure C. General Method of Preparation of Benzyl Compounds (14a-h)

(1'-(4-Fluorobenzyl)-3'-hydroxy-[1,4'-bipiperidin]-4-yl)(4-fluorophenyl)methanone (14a)

Into a solution of 13a (132 mg, 0.42 mmol) and triethylamine (17.1 mg, 1.69 mmol) in CH$_2$Cl$_2$ (15 mL), a solution of 4-fluorobenzyl bromide (80 mg, 0.42 mmol) in CH$_2$Cl$_2$ (5 mL) was slowly added. The reaction mixture was stirred at room temperature overnight. The reaction mixture was washed with water (20 mL×2) and brine solution (20 mL). The organic layer was dried over Na$_2$SO$_4$ and concentrated under reduced pressure. The crude product was purified by silica gel column chromatograph using triethylamine/ethyl acetate (1/50, v/v) as mobile phase to afford free base 14a as pale yellow oil (78.9 mg, 45%). $^1$H NMR (CDCl$_3$): δ 1.53-2.04 (m, 9H), 2.20-2.32 (m, 2H), 2.71-2.76 (m, 2H), 2.91-3.01 (m, 2H), 3.17-3.22 (m, 2H), 3.51-3.63 (m, 3H), 6.96-7.02 (m, 2H), 7.10-7.17 (m, 2H), 7.23-7.27 (m, 2H), 7.93-7.98 (m, 2H). Free base was converted to the oxalate salt by dissolving it in acetone and mixing with 1 equivalent of oxalic acid in acetone. mp: 234° C. (decomposed). Anal. (C$_{24}$H$_{28}$F$_2$N$_2$O$_2$.H$_2$C$_2$O$_4$.0.25H$_2$O) C, H, N.

(4-Fluorophenyl)(3'-hydroxy-1'-(4-methoxybenzyl)-[1,4'-bipiperidin]-4-yl)methanone (14b)

Procedure C was followed afford 14b (54 mg, 78%). $^1$H NMR (CDCl$_3$): δ 1.55-1.87 (m, 7H), 2.23-2.27 (m, 2H), 2.70-2.75 (m, 2H), 2.92-3.00 (m, 2H), 3.19-3.24 (m, 2H), 3.48-3.60 (m, 4H), 3.80 (s, 3H), 6.83-6.86 (m, 2H), 7.10-7.21 (m, 4H), 7.93-7.98 (m, 2H). Free base was converted to the oxalate salt. mp: 237° C. (decomposed). Anal. (C$_{25}$H$_{31}$FN$_2$O$_3$.H$_2$C$_2$O$_4$.0.5H$_2$O) C, H, N.

(1'-Benzyl-3'-hydroxy-[1,4'-bipiperidin]-4-yl)(4-fluorophenyl)methanone (14c). Procedure C was followed to afford 14c (54 mg, 84%). $^1$H NMR (CDCl$_3$): δ 1.57-2.03 (m, 8H), 2.17-2.28 (m, 2H), 2.71-2.76 (m, 2H), 2.93-3.01 (m, 2H), 3.20-3.25 (m, 2H), 3.50-3.63 (m, 4H), 7.10-7.16 (m, 2H), 7.24-7.31 (m, 5H), 7.93-7.98 (m, 2H). The free base was converted to the oxalate salt. mp: 243° C. (decomposed). Anal. (C$_{24}$H$_{29}$FN$_2$O$_2$.H$_2$C$_2$O$_4$.0.25H$_2$O) C, H, N.

(4-Fluorophenyl)(3'-hydroxy-1'-(pyridin-4-ylmethyl)-[1,4'-bipiperidin]-4-yl)methanone (14d)

Procedure C was followed to yield 14d (19 mg, 50%). The mobile phase used for column chromatographic separation was triethylamine/ethyl acetate/methanol (1/9/1, v/v/v). $^1$H NMR (CDCl$_3$): δ 1.71-2.02 (m, 8H), 2.24-2.28 (m, 2H), 2.74-2.76 (m, 2H), 2.91-3.00 (m, 2H), 3.17-3.21 (m, 2H), 3.50-3.60 (m, 4H), 7.10-7.17 (m, 2H), 7.23-7.27 (m, 1H), 7.62-7.65 (m, 1H), 7.94-7.98 (m, 2H), 8.50-8.52 (m, 2H). The free base was converted to the oxalate salt. mp: 178° C. (decomposed). Anal. (C$_{23}$H$_{28}$FN$_3$O$_2$.1.5H$_2$C$_2$O$_4$.H$_2$O) C, H, N. The structure of 14d has two tertiary amines and a pyridine ring and each of them neutralized with one proton. Each oxalic acid can generate two protons. Totally, each equivalent of base needs one and half oxalic acid.

(1'-(4-Fluorobenzyl)-3'-hydroxy-[1,4'-bipiperidin]-4-yl)(4-methoxyphenyl)methanone (14e)

Procedure C was followed to prepare 14e (24.5 mg, 63%). $^1$H NMR (CDCl$_3$): δ 1.56-2.28 (m, 8H), 2.18-2.30 (m, 2H), 2.70-2.74 (m, 2H), 2.92-2.99 (m, 2H), 3.19-3.23 (m, 2H), 3.48-3.62 (m, 4H), 3.87 (s, 3H), 6.83-6.95 (m, 4H), 7.18-7.21 (m, 2H), 7.90-7.94 (m, 2H). The free base was converted to the oxalate salt. mp: 231° C. (decomposed). Anal. ($C_{25}H_{31}FN_2O_3 \cdot H_2C_2O_4 \cdot 0.5H_2O$) C, H, N.

(3'-Hydroxy-1'-(4-methoxybenzyl)-[1,4'-bipiperidin]-4-yl)(4-methoxyphenyl)methanone (14f)

Procedure C was followed to prepare 14f (30 mg, 73%). $^1$H NMR (CDCl$_3$): δ 1.51-2.00 (m, 8H), 2.20-2.32 (m, 2H), 2.71-2.76 (m, 2H), 2.91-3.01 (m, 2H), 3.17-3.22 (m, 2H), 3.51-3.63 (m, 4H), 3.79 (s, 3H), 3.86 (s, 3H), 6.96-7.02 (m, 2H), 7.10-7.17 (m, 2H), 7.23-7.27 (m, 2H), 7.93-7.98 (m, 2H). The free base was converted to the oxalate salt. mp: 225° C. (decomposed). Anal. ($C_{25}H_{31}FN_2O_3 \cdot H_2C_2O_4 \cdot 0.5H_2O$) C, H, N.

(1'-Benzyl-3'-hydroxy-[1,4'-bipiperidin]-4-yl)(4-methoxyphenyl)methanone (14g)

Procedure C was followed to prepare 14g (32 mg, 34%). $^1$H NMR (CDCl$_3$): δ 1.54-2.04 (m, 8H), 2.22-2.27 (m, 2H), 2.70-2.75 (m, 2H), 2.93-3.00 (m, 2H), 3.20-3.25 (m, 2H), 3.54-3.62 (m, 4H), 3.86 (s, 3H), 6.92-6.95 (d, J=9 Hz, 2H), 7.26-7.31 (m, 5H), 7.91-7.94 (d, J=9 Hz, 2H). The free base was converted to the oxalate salt. mp: 234° C. (decomposed). Anal. ($C_{25}H_{32}N_2O_3 \cdot 2H_2C_2O_4$).

(3'-Hydroxy-1'-(pyridin-4-ylmethyl)-[1,4'-bipiperidin]-4-yl)(4-methoxyphenyl)methanone (14h)

Procedure C was followed to prepare 14h (20 mg, 52%). The mobile phase used for column chromatographic separation was triethylamine/ethyl acetate/methanol (1/9/1, v/v/v). $^1$H NMR (CDCl$_3$): δ 1.72-2.03 (m, 8H), 2.25-2.29 (m, 2H), 2.74-2.76 (m, 2H), 2.91-3.00 (m, 2H), 3.19-3.21 (m, 2H), 3.55-3.61 (m, 4H), 3.87 (s, 3H), 6.93-6.96 (d, J=9 Hz, 2H), 7.23-7.27 (m, 1H), 7.62-7.65 (m, 1H), 7.91-7.94 (d, J=9 Hz, 2H), 8.50-8.52 (m, 2H). The free base was converted to the oxalate salt. mp: 188° C. (decomposed). Anal ($C_{24}H_{31}N_3O_3 \cdot 2H_2C_2O_4 \cdot 0.5H_2O$) C, H, N.

Procedure D. General Method of Preparing Benzoic Compounds (15a-g)

(3'-Hydroxy-[1,4'-bipiperidine]-1',4-diyl)bis(4-fluorophenyl)methanone (15a)

Into a solution of 13a (50 mg, 0.163 mmol), BOP-Cl (100 mg, 0.40 mmol), and triethylamine (1 mL) in methylene chloride (30 mL) was added 4-fluorobenzoic acid (40 mg, 0.285 mmol). The reaction mixture was stirred overnight at room temperature. The reaction mixture was washed with saturated sodium carbonate (20 mL×5) and brine solution (20 mL). The organic layer was dried over Na$_2$SO$_4$ and concentrated under reducedpressure. The crude product was purified by silica gel column chromatography using triethylamine/ethyl acetate (1/50, v/v) as mobile phase to afford target product (62 mg, 89%). $^1$H NMR (CDCl$_3$): δ 1.54-1.93 (m, 7H), 2.27-2.34 (m, 1H), 2.44-2.52 (m, 1H), 2.80-2.98 (m, 5H), 3.23-3.26 (m, 1H), 3.30-3.60 (m, 1H), 4.80 (br s, 1H), 7.07-7.18 (m, 4H), 7.40-7.44 (m, 2H), 7.94-7.99 (m, 2H). The free base was converted to the oxalate salt. mp: 213° C. (decomposed). Anal. ($C_{24}H_{26}F_2N_2O_5 \cdot H_2C_2O_4$) C, H, N.

(4-(4-Fluorobenzoyl)-3'-hydroxy-[1,4'-bipiperidin]-1'-yl)(4-methoxyphenyl)methanone (15b)

Procedure D was followed to prepare 15b (48 mg, 22%). $^1$H NMR (CDCl$_3$): δ 1.54-1.93 (m, 7H), 2.31-2.34 (m, 1H), 2.44-2.51 (m, 1H), 2.79-2.98 (m, 5H), 3.23-3.26 (m, 1H), 3.47 (m, 2H), 3.82 (s, 3H), 6.91 (d, J=9 Hz, 2H), 7.14 (t, J=6 Hz, 2H), 7.38 (d, J=9 Hz, 2H), 7.94-7.99 (m, 2H). The free base was converted to the oxalate salt. mp: 206° C. (decomposed). Anal. ($C_{24}H_{27}FN_2O_3 \cdot H_2C_2O_4 \cdot 0.5H_2O$) C, H, N.

(1'-Benzoyl-3'-hydroxy-[1,4'-bipiperidin]-4-yl)(4-fluorophenyl)methanone (15c)

Procedure D was followed to prepare 15c (0.34 g, 78%). $^1$H NMR (CDCl$_3$): δ 1.75-1.80 (m, 2H), 1.80-1.95 (m, 4H), 2.20-2.40 (m, 1H), 2.40-2.60 (m, 1H), 2.60-3.00 (m, 5H), 3.10-3.30 (m, 1H), 4.10 (s br s, 1H), 4.86 (br s, 1H), 7.12-7.18 (m, 2H), 7.28-7.42 (m, 5H), 7.95-7.99 (m, 2H). The free base was converted to the oxalate salt. mp: 152° C. (decomposed). Anal. ($C_{24}H_{27}FN_2O_3 \cdot H_2C_2O_4 \cdot H_2O$) C, H, N.

(4-(4-Fluorobenzoyl)-3'-hydroxy-[1,4'-bipiperidin]-1'-yl)(pyridin-4-yl)methanone (15d)

Procedure D was followed to prepare 15d (33 mg, 83%). The mobile phase used for column chromatographic separation was triethylamine/ethyl acetate/methanol (1/9/1, v/v/v). $^1$H NMR (CDCl$_3$): δ 1.44-2.11 (m, 6H), 2.20-2.40 (m, 1H), 2.40-2.60 (m, 1H), 2.60-3.10 (m, 5H), 3.10-3.30 (m, 1H), 3.38-3.85 (m, 2H), 3.90-4.30 (m, 1H), 4.80-5.10 (m, 1H), 7.12-7.18 (m, 2H), 7.34-7.38 (m, 1H), 7.73-7.75 (m, 1H), 7.95-7.99 (m, 2H), 8.66-8.68 (m, 2H). The free base was converted to the oxalate salt. mp: 215° C. (decomposed). Anal. ($C_{23}H_{26}FN_3O_3 \cdot H_2C_2O_4 \cdot 0.25H_2O$) C, H, N.

(1'-(4-Fluorobenzoyl)-3'-hydroxy-[1,4'-bipiperidin]-4-yl)(4-methoxyphenyl)methanone (15e)

Procedure D was followed to prepare 15e (84 mg, 67%). $^1$H NMR (CDCl$_3$): 1.30-1.98 (m, 5H), 2.16-2.33 (m, 1H), 2.34-2.41 (m, 1H), 2.45-3.65 (m, 8H), 3.77 (s, 3H), 4.03 (br s, 1H), 4.72 (br s, 1H), 6.83-6.87 (m, 2H), 6.97-7.03 (m, 2H), 7.29-7.35 (m, 2H), 7.81-7.85 (m, 2H).

The free base was converted to the oxalate salt. mp: 216° C. (decomposed). Anal. ($C_{25}H_{29}FN_2O_4 \cdot H_2C_2O_4$) C, H, N.

(1'-Benzoyl-3'-hydroxy-[1,4'-bipiperidin]-4-yl)(4-methoxyphenyl)methanone (15f)

Procedure D was used to prepare 15f (0.14 g, 80%). $^1$H NMR (CDCl$_3$): δ 1.60-1.90 (m, 5H), 2.10-2.50 (m, 2H), 2.60-3.00 (m, 5H), 3.20-3.50 (m, 2H), 3.65 (s, 1H), 3.87 (s, 3H), 4.10 (s br, 1H), 5.30 (br s 1H), 6.94 (d, J=8.7 Hz, 2H), 7.38-7.40 (m, 5H), 7.92 (d, J=9 Hz, 2H). The free base was converted to the oxalate salt. mp: 188° C. (decomposed). Anal. ($C_{25}H_{30}N_2O_8 \cdot H_2C_2O_4 \cdot 1.5H_2O$) C, H, N.

(3'-Hydroxy-1'-isonicotinoyl-[1,4'-bipiperidin]-4-yl)(4-methoxyphenyl)methanone (15g)

Procedure D was followed to prepare 15g (36 mg, 90%). The mobile phase used for column chromatographic separation was triethylamine/ethyl acetate/methanol (1/9/1, v/v/v). $^1$H NMR (CDCl$_3$): δ 1.61-1.96 (m, 6H), 2.04-2.08 (m, 1H), 2.27-2.56 (m, 2H), 2.80-2.09 (m, 4H), 2.09-3.27 (m, 2H), 3.44-3.69 (m, 2H), 3.87 (s, 3H), 4.85-5.15 (m, 1H), 6.93-6.97 (m, 2H), 7.28-7.38 (m, 1H), 7.73-7.80 (m, 1H), 7.85-7.94 (m, 2H), 8.67-8.68 (m, 2H). The free base was converted to the oxalate salt. mp: 220° C. (decomposed). EIMS: Calcd, 429.1843. Found, 429.1843. Anal. ($C_{24}H_{29}N_3O_4 \cdot H_2C_2O_4$) C, H, N.

(1'-(4-Fluorobenzyl)-4'-hydroxy-[1,3'-bipiperidin]-4-yl)(4-fluorophenyl)methanone (16a)

Procedure C was followed to yield 16a as a pale yellow oil (28.7 mg, 43%). $^1$H NMR (CDCl$_3$): δ 1.55-2.05 (m, 9H), 2.24-2.31 (m, 1H), 2.49-2.57 (m, 1H), 2.71-2.83 (m, 3H), 2.94-3.04 (m, 2H), 3.17-3.20 (m, 1H), 3.40-3.49 (m, 3H), 6.98-7.05 (m, 2H), 7.10-7.17 (m, 2H), 7.25-7.30 (m, 2H), 7.92-7.97 (m, 2H). The free base was converted to the oxalate salt. mp: 209° C. (decomposed). Anal. (C$_{24}$H$_{28}$F$_2$N$_2$O$_2$.H$_2$C$_2$O$_4$) C, H, N.

(4-Fluorophenyl)(4'-hydroxy-1'-(4-methoxybenzyl)-[1,3'-bipiperidin]-4-yl)methanone (16b)

Procedure C was followed to prepare 16b (28 mg, 45%). $^1$H NMR (CDCl$_3$): δ 1.56-2.06 (m, 8H), 2.26-2.30 (m, 1H), 2.53-2.56 (m, 1H), 2.72-2.86 (m, 3H), 3.00-3.03 (m, 2H), 3.17-3.20 (m, 1H), 3.40-3.50 (m, 4H), 3.81 (s, 3H), 6.86-6.89 (m, 2H), 7.10-7.27 (m, 4H), 7.92-7.97 (m, 2H). The free base was converted to the oxalate salt. mp: 204° C. (decomposed). Anal. (C$_{25}$H$_{31}$FN$_2$O$_3$.H$_2$C$_2$O$_4$) C, H, N.

(1'-Benzyl-4'-hydroxy-[1,3'-bipiperidin]-4-yl)(4-fluorophenyl)methanone (16c)

Procedure C was followed to prepare 16c (40 mg, 62%). $^1$H NMR (CDCl$_3$): δ 1.56-2.06 (m, 8H), 2.24-2.3 (m, 1H), 2.51-2.59 (m, 1H), 2.72-2.86 (m, 3H), 3.00-3.04 (m, 2H), 3.17-3.20 (m, 1H), 3.40-3.54 (m, 4H), 7.10-7.15 (m, 2H), 7.26-7.33 (m, 5H), 7.92-7.97 (m, 2H). The free base was converted to the oxalate salt. mp: 200° C. (decomposed). Anal. (C$_{24}$H$_{29}$FN$_2$O$_2$.H$_2$C$_2$O$_4$) C, H, N.

(4-Fluorophenyl)(4'-hydroxy-1'-(pyridin-4-ylmethyl)-[1,3'-bipiperidin]-4-yl)methanone (16d)

Procedure C was followed to prepare 16d (22 mg, 56%). $^1$H NMR (CDCl$_3$): δ 1.56-2.08 (m, 8H), 2.24-2.32 (m, 1H), 2.48-2.53 (m, 1H), 2.70-3.04 (m, 5H), 3.19-3.59 (m, 5H), 7.13 (t, J=5.7 Hz, 2H), 7.26-7.31 (m, 1H), 7.66-7.69 (m, 1H), 7.92-7.97 (m, 2H), 8.52-8.54 (m, 2H). The free base was converted to the oxalate salt. mp: 182° C. Anal. (C$_{23}$H$_{28}$FN$_3$O$_2$.H$_2$C$_2$O$_4$.0.5H$_2$O) C, H, N.

(1'-(4-Fluorobenzyl)-4'-hydroxy-[1,3'-bipiperidin]-4-yl)(4-methoxyphenyl)methanone (16e)

Procedure C was followed to prepare 16e (38 mg, 55%). $^1$H NMR (CDCl$_3$): δ 1.55-2.06 (m, 8H), 2.28 (td, J=13.8, 2.1 Hz, 1H), 2.52 (td, J=10.5, 3.3 Hz, 1H), 2.71-2.84 (m, 3H), 2.90-3.10 (m, 2H), 3.04-3.20 (m, 1H), 3.40-3.49 (m, 4H), 3.86 (s, 3H), 6.92-7.04 (m, 4H), 7.25-7.30 (m, 2H), 7.89-7.92 (m, 2H). The free base was converted to the oxalate salt. mp: 221° C. (decomposed). Anal. (C$_{25}$H$_{31}$FN$_2$O$_3$.H$_2$C$_2$O$_4$) C, H, N.

(4'-Hydroxy-1'-(4-methoxybenzyl)-[1,3'-bipiperidin]-4-yl)(4-methoxyphenyl)methanone (16f)

Procedure C was followed to prepare 16f (32 mg, 78%). $^1$H NMR (CDCl$_3$): δ 1.54-2.06 (m, 8H), 2.24-2.28 (m, 1H), 2.50-2.53 (m, 1H), 2.72-2.86 (m, 3H), 2.98-3.02 (m, 2H), 3.17-3.20 (m, 1H), 3.41-3.48 (m, 3H), 3.62 (br s, 1H), 3.81 (s, 3H), 3.86 (s, 3H), 6.85-6.95 (m, 4H), 7.22 (dd, J=2.1, 6.9 Hz, 2H), 7.90 (dd, J=2.1, 6.9 Hz, 2H). The free base was converted to the oxalate salt. mp: 182° C. (decomposed). Anal. (C$_{26}$H$_{34}$N$_2$O$_4$.H$_2$C$_2$O$_4$) C, H, N.

(1'-Benzyl-4'-hydroxy-[1,3'-bipiperidin]-4-yl)(4-methoxyphenyl)methanone (16g)

Procedure C was followed to prepare 16g (90 mg, 71%). $^1$HNMR (CDCl$_3$): δ 1.57-2.04 (m, 8H), 2.25-2.32 (t, J=7 Hz, 1H), 2.51-2.60 (m, 1H), 2.70-2.86 (m, 3H), 3.00-3.04 (m, 2H), 3.17-3.20 (m, 1H), 3.40-3.59 (m, 4H), 3.86 (s, 3H), 6.91-6.94 (d, J=9 Hz, 2H), 7.26-7.33 (m, 5H), 7.89-7.92 (d, J=9 Hz, 2H). The free base was converted to the oxalate salt. mp: 220.3° C. (decomposed). Anal. (C$_{25}$H$_{32}$N$_2$O$_3$.H$_2$C$_2$O$_4$.0.5H$_2$O) C, H, N.

(4'-Hydroxy-1'-(pyridin-4-ylmethyl)-[1,3'-bipiperidin]-4-yl)(4-methoxyphenyl)methanone (16h)

Procedure C was followed to prepare 16h (13 mg, 34%). $^1$H NMR (CDCl$_3$): δ 1.58-2.08 (m, 8H), 2.22.29 (m, 1H), 2.52-2.53 (m, 1H), 2.70-3.04 (m, 5H), 3.18-3.20 (m, 1H), 3.42-3.54 (m, 4H), 3.87 (s, 3H), 6.91-6.96 (m, 2H), 7.26-7.30 (m, 1H), 7.63-7.70 (m, 1H), 7.89-7.94 (m, 2H), 8.52-8.54 (m, 2H). The free base was converted to the oxalate salt. mp: 202° C. Anal. (C$_{24}$H$_{31}$N$_3$O$_3$.H$_2$C$_2$O$_4$) C, H, N.

Procedure E. Method of preparing 1a,2,7,7a-tetrahydronaphtho[2,3-b]oxirene 2

To a solution of 1,4-dihydronaphthalene (8.6 g, 86% purity, 56.8 mmol) in dichloromethane (100 mL) at 0° C., m-chloroperoxybenzoic acid (17.0 g, 77% Purity, 75.8 mmol) in dichloromethane was added. After stirring for 5 h at 0° C., the solution was filtered to separate out the precipitated m-chlorobenzoic acid. The organic layer was washed with saturated Na$_2$CO$_3$, water, and brine (2×50 mL each). The organic layer was dried and concentrated under reduced pressure, the residue was purified by chromatography to give compound 2 (6.1 g, 73%). $^1$H NMR (CDCl$_3$): δ 3.17 (d, J=17.4 Hz, 2H), 3.31 (d, J=16.8 Hz, 2H), 3.46 (s, 2H), 7.02-7.15 (m, 4H).

5,8-Dihydronaphthalen-1-amine hydrochloride 4

A solution of 3 (10 g, 69.8 mmol) in oxylene (100 mL) and ethanol (30 mL) was stirred, and small pieces sodium (7.5 g, 326.0 mmol) was added during 1.5 h. The mixture was heated at 80° C. for 2 h, and poured onto ice. The organic layer was separated, washed with water. Hydrochloric acid (1:3, 50 mL) was added, the solid was collected by filtration, dried to give the crude product (7.0 g, 55%). The crude product was used in next step without further purification. $^1$H NMR (CDCl$_3$—CD$_3$OD): δ 3.45 (m, 7H), 5.90 (br, 2H), 7.12-7.35 (m, 3H).

N-(5,8-dihydronaphthalen-1-yl)-2,2,2-trifluoroacetamide 5

To a solution of 4 (7.0 g, 38.5 mmol) and NEt$_3$ (15 mL) in dichloromethane (120 mL) at 0° C., trifluoroacetic anhydride (13.0 g, 61.9 mmol) was added slowly. The reaction mixture was allowed to warm to room temperature and stirred for 2 h until complete by TLC, and then the mixture was washed by water, aqueous Na$_2$CO$_3$ solution, dried over Na$_2$SO$_4$, and concentrated under reduced pressure. The residue was purified by column chromatography to give 5 (8.0 g, 86%). $^1$H NMR (CDCl$_3$): δ 3.23 (m, 2H), 3.44 (m, 2H), 5.91 (m, 2H), 7.08 (d, J=7.8 Hz, 1H), 7.22 (t, J=8.1 Hz, 1H), 7.59 (d, J=7.8 Hz, 1H), 8.67 (br, 1H).

2,2,2-Trifluoro-N-(1a,2,7,7a-tetrahydronaphtho[2,3-b]oxiren-3-yl)acetamide 6

Compound 6 was prepared from 5 as describe in procedure A. Yield, 53%. $^1$H NMR (CDCl$_3$): δ 2.80-2.97 (m, 2H), 3.21-3.41 (m, 2H), 3.51-3.57 (m, 2H), 7.03-7.23 (m, 3H), 8.25 (br, 1H).

tert-Butyl 4-(methoxy(methyl)carbamoyl)piperidine-1-carboxylate 8

To a solution of 7 (2.5 g, 10.9 mmol) in dichloromethane (30 mL) at room temperature, carbonyldiimidazole (1.77 g, 11.0 mmol) was added. The mixture was stirred at room temperature for 1 h and then N, O-dimethylhydroxyamine hydrochloride (1.3 g, 13.3 mmol) and triethylamine were added. The reaction mixture was stirring overnight and was washed with aqueous Na$_2$CO$_3$, water, acetic acid (5%), dried, and concentrated under reduced pressure. The residue was purified by column chromatography to give 8 (2.70 g, 90%). $^1$H NMR (CDCl$_3$): δ 1.46 (s, 9H), 1.64-1.72 (m, 4H), 2.78 (br, 3H), 3.18 (s, 3H), 3.71 (s, 3H), 4.13 (br, 2H).

Procedure F: General Method of Preparing 9a-g

Method 1. tert-butyl 4-(6-methylnicotinoyl)piperidine-1-carboxylate 9a

To a solution of 5-bromo-2-methylpyridine (1.25 g, 7.2 mmol) in anhydrous THF (15 mL) at −40° C. under an argon atmosphere, lithium dibutyl(isopropyl)magnesate (5.2 mL, 0.7 M, 3.6 mmol) was added. The stirring was continued at the same temperature for 1 h. The resulting mixture was cannulated into a solution of 8 (1.5 g, 5.5 mmol) in THF (20 mL) at −78° C. The solution was maintained at −78° C. for 1 h, and then quenched with sat. aqueous NH$_4$Cl and allowed to warm to room temperature. The organic layer was separated and then the aqueous layer was extracted with ethyl acetate (2×20 mL). The combined organic layer was washed with water, dried over Na$_2$SO$_4$, filtered, and evaporated under reduced pressure to give the crude product. The crude compound was purified by chromatography on silica gel to obtain the desired compound 9a (0.7 g, 42%). $^1$H NMR (CDCl$_3$): δ 1.49 (s, 9H), 1.68-1.87 (m, 4H), 2.63 (s, 3H), 3.35 (m, 1H), 4.18 (br, 2H), 7.28 (d, J=8.4 Hz, 1H), 8.11 (dd, J=8.4, 2.1 Hz, 1H), 9.04 (d, J=2.1 Hz, 1H).

Method 2. tert-butyl 4-(6-methoxynicotinoyl)piperidine-1-carboxylate 9b

To a solution of 5-bromo-2-methyoxypyridine (2.6 g, 13.8 mmol) in anhydrous THF at −78° C., n-butyllithium (1.6M, 10 mL) was added. The solution was stirred for 45 minutes at −78° C. The resulting mixture was cannulated into a solution of 8 (2.5 g, 9.2 mmol) in THF (20 mL) at the same temperature and the reaction mixture was stirred at −78° C. for 4 h, then quenched with sat. aqueous NH$_4$Cl and allowed to warm to room temperature. The mixture was washed with brine and dried over Na$_2$SO$_4$, filtered, and evaporated under reduced pressure to give the crude product. The crude compound was purified by chromatography on silica gel to obtain the desired compound 9b (1.8 g, 61%). $^1$H NMR (CDCl$_3$): δ 1.47 (s, 9H), 1.62-1.86 (m, 5H), 2.88 (m, 2H), 3.31 (m, 1H), 4.01 (s, 3H), 4.19 (br, 2H), 6.81 (d, J=8.7 Hz, 1H), 8.13 (dd, J=8.7, 2.4 Hz, 1H), 8.79 (d, J=2.4 Hz, 1H).

tert-Butyl 4-nicotinoylpiperidine-1-carboxylate 9c

Compound 9c was prepared from 3-bromopyridine as describe in procedure B (Method 1). Yield, 31%. $^1$H NMR (CDCl$_3$): δ 1.47 (s, 9H), 1.63-1.89 (m, 4H), 2.92 (m, 2H), 3.38 (m, 2H), 4.20 (m, 2H), 7.44 (ddd, J=8.1, 5.1, 0.9 Hz, 1H), 8.22 (dt, J=8.1, 2.1 Hz, 1H), 8.79 (dd, J=5.1, 1.8 Hz, 1H), 9.16 (d, J=1.8 Hz,1H).

tert-Butyl 4-(1-methyl-1H-pyrrole-2-carbonyl)piperidine-1-carboxylate 9d

Compound 9d was prepared from 1-methyl-1H-pyrrole as describe in procedure B (Method 2). Yield, 34%. $^1$H NMR (CDCl$_3$): δ 1.47 (s, 9H), 1.66-1.80 (m, 4H), 2.83 (s, 2H), 3.17 (m, 1H), 3.94 (s, 3H), 4.18 (br, 2H), 6.15 (dd, J=4.2, 2.4 Hz, 1H), 6.84 (t, J=1.8 Hz, 1H), 6.99 (dd, J=4.2, 1.5 Hz, 1H).

tert-Butyl 4-(1-methyl-1H-pyrrole-4-carbonyl)piperidine-1-carboxylate 9e

Compound 9e was prepared from 3-bromo-1-methyl-1H-pyrrole as describe in procedure B (Method 2). Yield, 40%. $^1$H NMR (CDCl$_3$): δ 1.47 (s, 9H), 1.66-1.77 (m, 4H), 2.83 (s, 2H), 3.15-3.18 (m, 1H), 3.70 (s, 3H), 4.13 (br, 2H), 6.57-6.61 (m, 2H), 7.26-7.29 (m, 1H).

tert-Butyl 4-(3-methoxypicolinoyl)piperidine-1-carboxylate 9f

Compound 9f was prepared from 2-bromo-3-methoxypyridine as describe in procedure B (Method 2). Yield, 36%. $^1$H NMR (CDCl$_3$): δ 1.47 (s, 9H), 1.66-1.87 (m, 4H), 2.89 (s, 2H), 3.67-3.81 (m, 1H) 3.90 (s, 3H), 4.07 (br, 2H), 7.35-7.45 (m, 2H), 8.23-8.25 (m, 1H).

tert-Butyl 4-(3-fluoronicotinoyl)piperidine-1-carboxylate 9g

Compound 9g was prepared from 3-bromo-5-fluoropyridine as describe in procedure B (Method 2). Yield, 41%. $^1$H NMR (CDCl$_3$): δ 1.44 (s, 9H), 1.56-1.61 (m, 2H), 1.86-1.90 (m, 2H), 2.87 (s, 2H), 3.17-3.24 (m, 1H), 4.06 (br, 2H), 7.54-7.58 (m, H), 8.53-8.60 (m, 2H).

Procedure G: General Method of Preparing 10a-g.

(6-methylpyridin-3-yl)(piperidin-4-yl) methanone 10a

To a solution of 9a (0.7 g, 2.3 mmol) in CH$_2$Cl$_2$ (15 mL), TFA (2 mL) was added. The reaction mixture was stirred at room temperature for 4 h. The solvent was removed under reduced pressure and the residue was neutralized with aqueous NaOH solution and extracted with CH$_2$Cl$_2$ (2×15 mL). The organic layer was washed with brine, dried and concentrated to give the crude product. The crude product was purified with column chromatography to afforded 10a (0.33 g, 70%). $^1$H NMR (CDCl$_3$): δ 1.62-1.87 (m, 6H), 2.63 (s, 3H), 2.77 (m, 2H), 3.16-3.22 (m, 2H), 3.33 (m, 1H), 7.27 (d, J=8.4 Hz, 1H), 8.12 (dd, J=8.1, 2.4 Hz, 1H), 9.04 (d, J=2.4 Hz, 1H).

(6-Methoxypyridin-3-yl)(piperidin-4-yl)methanone 10b

Compound 10b was prepared from compound 9b as describe in procedure C. Yield, 77%. $^1$H NMR (CDCl$_3$): δ 1.65-1.89 (m, 4H), 2.40 (s, 1H), 2.78 (td, J=12.0, 2.7 Hz, 2H), 3.21 (dt, J=9.0, 3.6 Hz, 2H), 3.31 (m, 1H), 4.00 (s, 3H), 6.79 (d, J=8.4 Hz, 1H), 8.13 (dd, J=8.4, 2.4 Hz, 1H), 8.78 (d, J=2.4 Hz, 1H).

Piperidin-4-yl(pyridin-3-yl)methanone 10c

Compound 10c was prepared from compound 9c as describe in procedure C. Yield, 85%. $^1$H NMR (CDCl$_3$): δ 1.62-1.77 (m, 2H), 1.86-1.89 (m, 3H), 2.79 (td, J=12.6, 2.7 Hz, 2H), 3.21 (dt, J=12.9, 3.0 Hz, 2H), 3.37 (tt, J=11.4, 3.9 Hz, 1H), 7.43 (ddd, J=8.1, 4.8, 0.9 Hz, 1H), 8.22 (ddd, J=4.8, 2.1, 1.5 Hz, 1H), 8.78 (dd, J=4.5, 1.5 Hz, 1H), 9.16 (dd, J=2.4, 0.9 Hz, 1H).

(1-Methyl-1H-pyrrol-2-yl)(piperidin-4-yl)methanone 10d

Compound 10d was prepared from compound 9d as describe in procedure C. Yield, 72%. $^1$H NMR (CDCl$_3$): δ 1.76-1.87 (m, 4H), 2.81 (m, 2H), 3.17-3.23 (m, 4H), 3.94 (s, 3H), 6.14 (m, 1H), 6.83 (m, 1H), 6.98 (m, 1H).

(1-Methyl-1H-pyrrol-3-yl)(piperidin-4-yl)methanone 10e

Compound 10e was prepared from compound 9e as describe in procedure C. Yield, 80%. $^1$H NMR (CDCl$_3$): δ 1.76-1.80 (m, 4H), 2.65-2.73 (m, 2H), 3.01-3.17 (m, 4H), 3.68 (s, 3H), 6.57-6.59 (m, 2H), 7.25 (s, 1H).

(3-Methoxypyridin-2-yl)(piperidin-4-yl)methanone 10f

Compound 10f was prepared from compound 9f as describe in procedure C. Yield, 78%. $^1$H NMR (CDCl$_3$): δ 1.51-1.81 (m, 4H), 2.69 (s, 2H), 3.08-3.25 (m, 3H), 3.49-3.58 (m, 1H), 3.83 (s, 3H), 7.27-7.36 (m, 2H), 8.16-8.18 (m, 1H).

(5-Fluoropyridin-3-yl)(piperidin-4-yl)methanone 10g

Compound 10g was prepared from compound 9g as describe in procedure C. Yield, 79%. $^1$H NMR (CDCl$_3$): δ 1.56-1.61 (m, 2H); 1.86-1.90 (m, 2H); 2.87 (m, 2H); 3.17-3.21 (m, 4H); 7.56 (s, 1H); 8.53-8.60 (m, 2H).

Procedure H: General Method of Preparing 11a-b, d-g

(OS-5-40, OS-5-88, OS-5-60, Tz-4-1-114, Tz-4-1-92 and TZ-4-1-96) (1-(3-hydroxy-1,2,3,4-tetrahydronaphthalen-2-yl)piperidin-4-yl)(6-methoxypyridin-3-yl)methanone oxalate 11a OS-5-40

A mixture of 10a (0.32 g, 1.4 mmol), 2 (0.10 g, 0.68 mmol) and EtN$_3$ (0.3 mL) in ethanol (5 mL) was stirred at 50° C. for 36 h. After cooled to room temperature, the mixture was poured into water, extracted with EtOAc (3×15 mL). The organic layer was dried and concentrated under reduced pressure. The residue was purified by column chromatography to give 11a OS-5-40 (0.11 g, 44%). $^1$H NMR (CDCl$_3$, free base): δ 1.80-2.02 (m, 4H), 2.43 (m, 1H), 2.78-3.06 (m, 7H), 3.20-3.38 (m, 2H), 3.89 (m, 1H), 4.04 (s, 3H), 6.83 (d, J=8.7 Hz, 1H), 7.11-7.18 (m, 4H), 8.17 (dd, J=8.7, 2.4 Hz, 1H), 8.82 (d, J=2.4 Hz, 1H). The free base was converted to the oxalate salt. mp: 223-224° C. ° C. Anal. (C$_{22}$H$_{26}$N$_2$O$_3$.H$_2$C$_2$O$_4$) C, H, N.

(1-(3-Hydroxy-1,2,3,4-tetrahydronaphthalen-2-yl)piperidin-4-yl)(6-methylpyridin-3-yl)methanone oxalate 11b OS-5-88

Compound 11b OS-5-88 was prepared from compound 10b as describe in procedure D. Yield, 42%. $^1$H NMR (CDCl$_3$, free base): δ 1.74-1.96 (m, 4H), 2.41 (m, 1H), 2.62 (s, 3H), 2.75-3.01 (m, 7H), 3.26-3.33 (m, 2H), 3.86 (m, 1H), 4.17 (br, 1H), 7.06-7.14 (m, 4H), 7.27 (d, J=8.1 Hz, 1H), 8.11 (dd, J=8.1, 2.1 Hz, 1H), 9.03 (d, J=2.1 Hz, 1H). The free base was converted to the oxalate salt. mp: 240-241° C. Anal. (C$_{22}$H$_{26}$N$_2$O$_2$.2H$_2$C$_2$O$_4$.0.5H$_2$O) C, H, N.

(1-(3-Hydroxy-1,2,3,4-tetrahydronaphthalen-2-yl)piperidin-4-yl)(1-methyl-1H-pyrrol-2-yl) methanone oxalate 11d OS-5-60

Compound 11 d OS-5-60 was prepared from compound 10d as describe in procedure D. Yield, 47%. $^1$H NMR (CDCl$_3$, free base): δ 1.81-2.03 (m, 4H), 2.37 (m, 1H), 2.76-3.13 (m, 8H), 3.30 (m, 1H), 3.88 (m, 1H), 3.95 (s, 3H), 4.45 (br, 1H), 6.14 (m, 1H), 6.83 (m, 1H), 6.98 (m, 1H), 7.09-7.16 (m, 4H). The free base was converted to the oxalate salt. mp: 212-213° C. Anal. (C$_{21}$H$_{26}$N$_2$O$_2$.H$_2$C$_2$O$_4$) C, H, N.

(1-(3-Hydroxy-1,2,3,4-tetrahydronaphthalen-2-yl)piperidin-4-yl)(1-methyl-1H-pyrrol-3-yl)methanone oxalate 11e Tz-4-1-114

Compound 11e Tz-4-1-114 was prepared from compound 10e as describe in procedure D. Yield, 50%. $^1$H NMR (CDCl$_3$, free base): δ 1.83-2.00 (m, 4H), 2.38 (m, 1H), 2.76-3.13 (m, 8H), 3.29-3.35 (m, 1H), 3.71 (s, 3H), 4.32 (br, 1H), 6.61 (m, 2H), 7.12-7.16 (m, 4H), 7.30-7.31 (m, 1H). The free base was converted to the oxalate salt. mp: ° C. Anal. (C$_{21}$H$_{26}$N$_2$O$_2$.H$_2$C$_2$O$_4$) C, H, N.

(1-(3-Hydroxy-1,2,3,4-tetrahydronaphthalen-2-yl)piperidin-4-yl)(3-methoxypyridin-2-yl)methanone oxalate 11f Tz-4-1-92

Compound 11f Tz-4-1-92 was prepared from compound 10f as describe in procedure D. Yield, 36%. $^1$H NMR (CDCl$_3$, free base): δ 1.72-1.96 (m, 4H), 2.33-2.41 (m, 1H), 2.72-2.96 (m, 7H), 3.26-3.33 (m, 1H), 3.55-3.63 (m, 1H), 3.81-3.90 (m, 1H), 4.30 (br, 1H), 7.06-7.14 (m, 4H), 7.26-7.39 (m, 2H), 8.23-8.25 (m, 1H). The free base was converted to the oxalate salt. mp: ° C. Anal. (C$_{22}$H$_{26}$N$_2$O$_3$.H$_2$C$_2$O$_4$) C, H, N.

(5-Fluoropyridin-3-yl)(1-(3-hydroxy-1,2,3,4-tetrahydronaphthalen-2-yl)piperidin-4-yl)methanone oxalate 11g TZ-4-1-96

Compound 11g TZ-4-1-96 was prepared from compound 10g as describe in procedure D. Yield, 44%. $^{11}$H NMR (CDCl$_3$, free base): δ 1.70-2.04 (m, 4H), 2.34-2.43 (m, 1H), 2.75-3.34 (m, 8H), 3.82-3.90 (m, 1H), 4.13 (br, 1H), 7.06-7.11 (m, 4H), 7.57-7.61 (m, 1H), 8.56-8.62 (m, 2H). The free base was converted to the oxalate salt. mp: ° C. Anal. (C$_{21}$H$_{23}$FN$_2$O$_2$.H$_2$C$_2$O$_4$) C, H, N.

Procedure I: General Method of Preparing 12a-d

(1-(8-amino-3-hydroxy-1,2,3,4-tetrahydronaphthalen-2-yl)piperidin-4-yl)(6-methylpyridin-3-yl)methanone oxalate 12a (OS-5-70)

A mixture of 6 (0.20 g, 0.78 mmol), 10a (0.47 g, 2.3 mmol) and EtN$_3$ (0.5 mL) in ethanol (7 mL) was stirred at 60° C. for 2 d. To the mixture aqueous NaOH (1M, 3 mL) was added and the stiffing was continued overnight. The solvent was removed, the residue was extracted with EtOAc (3×10 mL) and organic layer was washed with aqueous Na$_2$CO$_3$ solution, dried and concentrated. The crude product was purified by column chromatography to give 12a (OS-5-70). (0.13 g, 44%). $^1$H NMR (CDCl$_3$, free base): δ 1.79-1.99 (m, 5H), 2.35-2.53 (m, 2H), 2.64 (s, 3H), 2.67-3.28 (m, 8H), 3.62 (br, 2H), 3.87 (m, 1H), 6.57 (m, 2H), 6.99 (m, 1H), 7.29 (d, J=8.1 Hz, 1H), 8.13 (dd, J=8.1, 2.1 Hz, 1H), 9.04 (d, J=2.1 Hz, 1H). The oxalate salt was prepared using oxalic acid in ethyl acetate, mp: 98-103° C. Anal. (C$_{22}$H$_{27}$N$_3$O$_2$.2H$_2$C$_2$O$_4$.H$_2$O) C, H, N.

(1-(8-Amino-3-hydroxy-1,2,3,4-tetrahydronaphthalen-2-yl)piperidin-4-yl)(6-methoxypyridin-3-yl)methanone oxalate 12b (OS-5-82)

Compound 12b (OS-5-82) was prepared from compound 10b as describe in procedure E. Yield, 43%. $^1$H NMR (CDCl$_3$, free base): δ 1.65 (br, 1H), 1.80-2.02 (m, 4H), 2.42-2.53 (m, 2H), 2.67-3.03 (m, 6H), 3.21-3.28 (m, 2H), 3.61 (br s, 2H), 3.86 (m, 1H), 4.02 (s, 3H), 6.57 (m, 2H), 6.82 (d, J=8.7 Hz, 1H), 6.99 (t, J=7.8 Hz, 1H), 8.15 (dd, J=8.7, 2.4 Hz, 1H), 8.80 (d, J=2.4 Hz, 1H). The free base was converted to the oxalate salt. mp: 81.4-83.2° C. Anal. (C$_{22}$H$_{27}$N$_3$O$_3$.2H$_2$C$_2$O$_4$.1.5H$_2$O) C, H, N.

(1-(8-Amino-3-hydroxy-1,2,3,4-tetrahydronaphthalen-2-yl)piperidin-4-yl)(pyridin-3-yl)methanone oxalate 12c (OS-5-110)

Compound 12c (OS-5-110) was prepared from compound 10c as describe in procedure E. Yield, 61%. $^1$H NMR-(CDCl$_3$, free base): δ 1.80-2.05 (m, 4H), 2.36-2.53 (m, 2H), 2.68-2.92 (m, 5H), 3.01-3.35 (m, 4H), 3.61 (br, 2H), 3.87 (m, 1H), 6.54-6.60 (m, 2H), 6.99 (td, J=7.5, 3.3 Hz, 1H), 7.45 (dd, J=8.1, 4.8 Hz, 1H), 8.24 (dt, J=8.1, 1.8 Hz, 1H), 8.80 (dd, J=4.8, 1.8 Hz, 1H), 9.17 (d, J=2.1 Hz, 1H). The free base was converted to the oxalate salt. mp: 109.0-111.2° C. Anal. (C$_{21}$H$_{25}$N$_3$O$_2$.2H$_2$C$_2$O$_4$.0.5H$_2$O) C, H, N.

(1-(8-Amino-3-hydroxy-1,2,3,4-tetrahydronaphthalen-2-yl)piperidin-4-yl)(1-methyl-1H-pyrrol-2-yl)methanone oxalate 12d (OS-5-72-2)

Compound 12d (OS-5-72-2) was prepared from compound 10d as describe in procedure E. Yield, 37%. $^1$H NMR (CDCl$_3$, free base): δ 1.85-1.96 (m, 4H), 2.43-2.53 (m, 2H), 2.67-2.89 (m, 5H), 2.96-3.28 (m, 3H), 3.60 (br, 2H), 3.85 (m, 1H), 3.95 (s,3H), 6.14 (m, 1H), 6.57 (m, 2H), 6.83 (br, 1H), 6.96-7.02 (m, 2H). The free base was converted to the oxalate salt. mp: 131-133° C. Anal. (C$_{21}$H$_{27}$N$_3$O$_2$.2H$_2$C$_2$O$_4$.1.5H$_2$O) C, H, N.

(1-(5-Amino-3-hydroxy-1,2,3,4-tetrahydronaphthalen-2-yl)piperidin-4-yl)(1-methyl-1H-pyrrol-2-yl)methanone 13d (OS-5-2-72-1)

Compound 13d (OS-5-2-72-1) was prepared from compound 10d as describe in procedure E. Yield, 20%. $^1$H NMR (CDCl$_3$, free base): δ 1.85-1.96 (m, 4H), 2.36-2.45 (m, 2H), 2.76-2.89 (m 5H), 2.96-3.16 (m, 3H), 3.62 (br, 2H), 3.92 (m, 1H), 3.96 (s,3H), 6.15 (m, 1H), 6.56 (m, 2H), 6.83 (br, 1H), 6.96-7.02 (m, 2H). The free base was converted to the oxalate salt. mp: 114-115° C. Anal. (C$_{21}$H$_{27}$N$_3$O$_2$.2H$_2$C$_2$O$_4$.2H$_2$O) C, H, N.

Procedure J: General Method for the Synthesis of Compound 17a-b 4-bromo-1-methylpyridin-2(1H)-one (17a)

A solution of 4-bromopyridin-2-amine (600 mg, 3.5 mmol) in a mixture of 2M H$_2$SO$_4$ (20 mL) and 2M Na$_2$NO$_2$ (10 mL) was stirred at 0-5° C. for 2 h. The reaction mixture was extracted with CH$_2$Cl$_2$, and the organic layer was washed with brine, dried over anhydrous Na$_2$SO$_4$ and concentrated. The crude product was used in next step without further purification. The crude product 15a, potassium carbonate (3.6 mmol) and methyl iodide (3.7 mmol) were refluxed in acetone (100 mL) in a sealed tube for 4 h. The reaction mixture was cooled, and potassium carbonate was filtered off. The acetone was evaporated off and a small amount of water was added to the residue. This solution was extracted with CH$_2$Cl$_2$. The organic layer was dried, concentrated and purified with column chromatography to afforded 17a (355 mg, 57%). $^1$H NMR (CDCl$_3$,): δ 3.49 (s, 3H), 6.31 (d, J=6.0 Hz, 1H), 6.82 (s, 1H), 7.14 (d, J=6.0 Hz, 1H).

6-Bromo-1-methylpyridin-2(1H)-one 17b

Compound 17b was prepared from compound 14b as describe in procedure F. Yield, 54%. $^1$H NMR (CDCl$_3$,): δ 3.73 (s, 3H), 6.46-6.52 (m, 2H), 7.10-7.16 (m, 1H).

tert-Butyl 4-(1-methyl-2-oxo-1,2-dihydropyridine-4-carbonyl)piperidine-1-carboxylate 18a Compound 18a was prepared from compound 17a as describe in procedure B (Method 2). Yield, 38%. $^1$H NMR (CDCl$_3$): δ 1.47 (s, 9H), 1.56-1.87 (m, 4H), 2.82 (s, 2H), 3.05-3.07 (m, 1H), 3.50 (s, 3H), 4.17 (br, 2H), 6.49 (d, J=6.0 Hz, 1H), 6.73 (d, J=6.0 Hz, 1H), 7.36 (s, 1H).

tert-Butyl 4-(1-methyl-6-oxo-1,6-dihydropyridine-2-carbonyppiperidine-1-carboxylate 18b Compound 18b was prepared from compound 17b as describe in procedure B (Method 2). Yield, 35%. $^1$H NMR (CDCl$_3$): δ 1.45 (s, 9H), 1.58-1.87 (m, 4H), 2.81 (s, 2H), 3.05-3.07 (m, 1H), 3.47 (s, 3H), 4.14 (br, 2H), 6.44-6.47 (m, 1H), 6.69-6.72 (m, 1H), 7.30-7.36 (m, 1H).

1-Methyl-5-(piperidine-4-carbonyl)pyridin-2(1H)-one (19a)

Compound 19a was prepared from compound 18a as describe in procedure C. Yield, 79%. $^1$H NMR (CDCl$_3$): δ 1.57-1.88 (m, 4H), 2.83 (s, 2H), 3.03-3.09 (m, 4H), 3.50 (s, 3H), 6.50 (d, J=6.0 Hz, 1H), 6.72 (d, J=6.0 Hz, 1H), 7.38 (s, 1H).

1-Methyl-6-(piperidine-4-carbonyl)pyridin-2(1H)-one (19b)

Compound 19b was prepared from compound 18b as describe in procedure C. Yield, 75%. $^1$H NMR (CDCl$_3$): δ 1.58-1.87 (m, 4H), 2.82 (s, 2H), 3.02-3.10 (m, 4H), 3.47 (s, 3H), 6.42-6.48 (m, 1H), 6.67-6.72 (m, 1H), 7.31-7.36 (m, 1H).

4-(1-(3-Hydroxy-1,2,3,4-tetrahydronaphthalen-2-yl)piperidine-4-carbonyl)-1-methylpyridin-2(1H)-one oxalate (20a TZ-4-1-150)

Compound 20a TZ-4-1-150 was prepared from compound 19a as describe in procedure E. Yield, 37%. $^1$H NMR (CDCl$_3$, free base): δ 1.72-1.99 (m, 4H), 2.33-2.39 (m, 1H), 2.75-3.01 (m, 8H), 3.27-3.34 (m, 2H), 3.50 (s, 3H), 3.82-3.91 (m, 1H), 6.45 (d, J=6.0 Hz, 1H), 6.72 (d, J=6.0 Hz, 1H), 7.35 (s, 1H). The free base was converted to the oxalate salt. mp: ° C. Anal. ($C_{22}H_{26}N_2O_3$) C, H, N.

6-(1-(3-Hydroxy-1,2,3,4-tetrahydronaphthalen-2-yl)piperidine-4-carbonyl)-1-methylpyridin-2(1H)-one (20b TZ-4-1-148)

Compound 20b TZ-4-1-148 was prepared from compound 19b as describe in procedure E. Yield, 39%. $^1$H NMR ($CDCl_3$, free base): δ 1.72-2.04 (m, 4H), 2.32-2.39 (m, 1H), 2.81-3.01 (m, 8H), 3.27-3.34 (m, 2H), 3.50 (s, 3H), 3.82-3.89 (m, 1H), 4.08 (br, 1H), 6.43-6.46 (m, 1H), 6.70-6.73 (m, 1H), 7.06-7.14 (m, 4H), 7.31-7.37 (m, 1H). The free base was converted to the oxalate salt. mp: ° C. Anal. ($C_{22}H_{26}N_2O_3$) C, H, N.

1-(3-Hydroxy-1,2,3,4-tetrahydronaphthalen-2-yl)-N-methoxy-N-methylpiperidine-4-carboxamide 22

Compound 21 was prepared from compound 8 as describe in procedure C. The crude product was used in next step without further purification. Compound 22 was prepared from compound 21 as describe in procedure D. Yield, 40%. $^1$H NMR ($CDCl_3$): δ 1.81-1.93 (m, 4H), 2.28-2.31 (m, 1H), 2.75-2.97 (m, 8H), 3.27-3.20 (s, 3H), 3.27-3.34 (m, 1H), 3.72 (s, 3H), 3.85-3.90 (m, 1H), 4.27 (br, 1H), 7.09-7.13 (m, 4H).

1-(3-((tert-Butyldimethylsilyl)oxy)-1,2,3,4-tetrahydronaphthalen-2-yl)-N-methoxy-N-methylpiperidine-4-carboxamide 23

To a solution of 22 (400 mg, 1.25 mmol) and imidazole (400 mg) in $CH_2Cl_2$ (50 mL), TBDMSCl (2.5 mmol) was added. The reaction mixture was stirred overnight at room temperature until TLC indicated that the reaction was complete. The reaction mixture was washed by brine and 1M $NaH_2PO_4$ (30 mL×3). The organic layer was dried and concentrated to a residue. The crude product was purified with column chromatography to afforded 23 (400 mg, 70%). $^1$H NMR ($CDCl_3$,): δ 0.12 (s, 6H), 0.91 (s, 9H), 1.65-1.77 (m, 4H), 2.46-3.05 (m, 9H), 3.17 (s, 3H), 3.69 (s, 3H), 4.13 (br, 2H), 7.04-7.12 (m, 4H).

(1-(3-(tert-Butyldimethylsilyloxy)-1,2,3,4-tetrahydronaphthalen-2-yl)piperidin-4-yl)(6-fluoropyridin-3-yl) methanone 24a Compound 24a was prepared from compound 23 as describe in procedure E. Yield, 36%. $^1$H NMR ($CDCl_3$): δ 0.12 (s, 6H), 0.91 (s, 9H), 1.65-1.77 (m, 4H), 2.46-3.05 (m, 9H), 3.17 (s, 3H), 3.69 (s, 3H), 4.13 (br, 2H), 7.04-7.12 (m, 4H), 8.23-8.37 (m, 2H), 8.78 (s, 1H).

(1-(3-(tert-Butyldimethylsilyloxy)-1,2,3,4-tetrahydronaphthalen-2-yl)piperidin-4-yl)(2-fluoropyridin-3-yl) methanone 24b Compound 24b was prepared from compound 23 as describe in procedure E. Yield, 39%. $^1$H NMR ($CDCl_3$): δ 0.12 (s, 6H), 0.91 (s, 9H), 1.65-1.77 (m, 4H), 2.46-3.05 (m, 9H), 3.17 (s, 3H), 3.69 (s, 3H), 4.13 (br, 2H), 7.04-7.12 (m, 4H), 7.04-7.11 (m, 4H), 7.31-7.397 (m, H), 8.23-8.30 (m, 1H), 8.38-8.40 (m, 1H).

Procedure K: General Method for the Synthesis of Compound 25a-b

(6-fluoropyridin-3-yl)(1-(3-hydroxy-1,2,3,4-tetrahydronaphthalen-2-yl)piperidin-4-yl)methanone oxalate 25a Tz-4-1-154

A mixture of compound 24a and HCl (12N, 5 mL) in THF were stirred for 4 h at room temperature until TLC indicated that the reaction was complete, and then carefully neutralized with NaOH (1N) and extracted with $CH_2Cl_2$. The organic layer was dried and concentrated under reduce pressure. The crude product was purified with column chromatography to afforded 25a (yield, 79%). $^1$H NMR ($CDCl_3$, free base): δ 1.84-2.03 (m, 4H), 2.38-2.46 (m, 1H), 2.75-3.02 (m, 7H), 3.21-3.34 (m, 2H), 3.55-3.63 (m, 1H), 3.82-3.89 (m, 1H), 4.30 (br, 1H), 7.03-7.11 (m, 4H), 8.33-8.39 (m, 2H), 8.79 (s, 1H). The free base was converted to the oxalate salt. mp: ° C. Anal. ($C_{21}H_{23}FN_2O_2.H_2C_2O_4$) C, H, N.

(2-fluoropyridin-3-yl)(1-(3-hydroxy-1,2,3,4-tetrahydronaphthalen-2-yl)piperidin-4-yl)methanone 25b Tz-4-1-122

Compound 25b Tz-4-1-122 was prepared from compound 24b as describe in procedure G. Yield, 75%. $^1$H NMR ($CDCl_3$, free base): δ 1.84-2.03 (m, 4H), 2.38-2.46 (m, 1H), 2.75-2.99 (m, 7H), 3.25-3.33 (m, 2H), 3.80-3.90 (m, 1H), 4.31 (br, 1H), 7.04-7.11 (m, 4H), 7.31-7.397 (m, H), 8.23-8.30 (m, 1H), 8.38-8.40 (m, 1H). The free base was converted to the oxalate salt. mp: ° C. Anal. ($C_{21}H_{23}FN_2O_2.H_2C_2O_4$) C, H, N.

2-bromo-3-(2-fluoroethoxy)pyridine 28

A mixture of 2-bromopyridin-3-ol 27 (0.1 mmol), 1-bromo-2-fluoroethane (0.2 mmol) and $K_2CO_3$ (0.4 mmol) in acetonitrile were stirred at refluxing for one day until TLC indicated that the reaction was complete, and then filter, dried and concentrated under reduce pressure. The crude product was purified with column chromatography to afforded 28 (yield, 68%). $^1$H NMR ($CDCl_3$): δ 4.25-4.34 (m, 2H), 4.73-4.89 (m, 2H), 7.20-7.22 (m, 2H), 8.01 (s, 1H).

tert-butyl 4-(3-(2-fluoroethoxy)picolinoyl)piperidine-1-carboxylate 29

To a solution of 28 (7.3 mmol) in THF was added 1.6 N butyllithium/hexane solution (7 ml) at −78° C. under $N_2$ atmosphere. The solution was stirred at −78° C. for 1 hour and a solution of tert-butyl 4-(methoxy(methyl)carbamoyl)piperidine-1-carboxylate (1 g, 3.6 mmol) in THF was added. The solution was maintained at −78° C. for 4 hour, and then quenched with sat. aqueous $NH_4Cl$ and allowed to warm to rt with stirring. The organic layer was separated and then the aqueous layer was extracted with ethyl acetate. The combine extract was washed with water, dried over $Na_2SO_4$, filtered, concentrated, and the residue chromatographed on silica eluted with an ethyl acetate-hexane (1:4, v/v) and the aimed product was obtained. The yield was 40%. NMR ($CDCl_3$): δ 1.47 (s, 9H), 1.62-1.70 (m, 4H), 2.83 (s, 2H), 3.64-3.73 (m, 1H), 4.17 (br, 2H), 4.25-4.36 (m, 2H), 4.68-4.87 (m, 2H), 7.23-7.26 (m, 1H), 7.38-7.40 (m, 1H), 8.25-8.30 (m, 1H).

(3-(2-fluoroethoxy)pyridin-2-yl)(1-(3-hydroxy-1,2,3,4-tetrahydronaphthalen-2-yl)piperidin-4-yl)methanone oxalate 31 (TZ-4-2-12)

Compound 31 (TZ-4-2-12) was prepared from compound 29 as describe in procedure C and E. The yield was 43%. $^1$H NMR (CDCl$_3$, free base): δ 1.73-1.98 (m, 4H), 2.32-2.40 (m, 1H), 2.71-2.96 (m, 8H), 3.31-3.33 (m, 1H), 3.49-3.56 (m, 1H), 3.80-3.89 (m, 1H), 4.24-4.36 (m, 2H), 4.69-4.87 (m, 2H), 7.09-7.25 (m, 4H), 7.34-7.38 (m, 2H), 8.27-8.29 (m, 1H). The free base was converted to the oxalate salt. mp: ° C. Anal. (C$_{23}$H$_{27}$FN$_2$O$_3$.H$_2$C$_2$O$_4$) C, H, N.

In Vitro Biological Evaluations

Sigma Receptor Binding Assays.

The compounds were dissolved in DMF, DMSO, or ethanol, and then diluted in 50 mM Tris-HCl buffer containing 150 mM NaCl and 100 mM EDTA at pH 7.4, prior to performing the σ$_1$ and σ$_2$ receptor binding assays. The procedures for isolating the membrane homogenates and performing the σ$_1$ and σ$_2$ receptor binding assays have been previously described in detail.[40,51]

Briefly, the σ$_1$ receptor binding assays were conducted in 96-well plates using guinea pig brain membrane homogenates (~300 μg protein) and ~5 nM (+)-[$^3$H]pentazocine (34.9 Ci/mmol, Perkin-Elmer, Boston, Mass.). The total incubation time was 90 min at room temperature. Nonspecific binding was determined from samples that contained 10 μM of cold haloperidol. After 90 min, the reaction was quenched by adding 150 μL of ice-cold wash buffer (10 mM Tris-HCl, 150 mM NaCl, pH 7.4) using a 96 channel transfer pipet (Fisher Scientific, Pittsburgh, Pa.). The samples were harvested and filtered rapidly through a 96-well fiberglass filter plate (Millipore, Billerica, Mass.) that had been presoaked with 100 μL of 50 mM Tris-HCl buffer at pH 8.0 for 1 h. Each filter was washed 3 times with 200 μL of ice-cold wash buffer, and the filter counted in a Wallac 1450 MicroBeta liquid scintillation counter (Perkin-Elmer, Boston, Mass.).

The σ$_2$ receptor binding assays were conducted using rat liver membrane homogenates (~300 μg protein) and ~5 nM [$^3$H]DTG (58.1 Ci/mmol, Perkin-Elmer, Boston, Mass.) in the presence of 1 μM of (+)-pentazocine to block σ$_1$ sites. The incubation time was 2 h at room temperature. Nonspecific binding was determined from samples that contained 10 μM of cold haloperidol. All other procedures were identical to those described for the σ$_1$ receptor binding assay above.

Data from the competitive inhibition experiments were modeled using nonlinear regression analysis to determine the concentration that inhibits 50% of the specific binding of the radioligand (IC$_{50}$ value). Competitive curves were best fit to a one-site fit and gave pseudo-Hill coefficients of 0.6-1.0. K$_i$ values were calculated using the method of Cheng and Prusoff and are presented as the mean (±1 SEM). For these calculations, we used a K$_d$ value of 7.89 nM for (+)-[$^3$H] pentazocine and guinea pig brain and a K$_d$ value of 30.73 nM for [$^3$H]DTG and rat liver.

Vesicular Acetylcholine Transporter Binding Assays

In vitro binding assays of these novel compounds to VAChT were conducted with human vesicular acetylcholine transporter (VAChT) permanently expressed in PC12[4123.7] cells at about 50 pmol/mg of crude extract. The radioligand used was 5 nM (−)-[$^3$H]vesamicol, and the assay was conducted as described at final concentrations of $10^{-11}$ M to $10^{-5}$ M novel compound (53). Unlabeled (−)-vesamicol was used as an external standard, for which K$_i$=15 nM, and the mixture was allowed to equilibrate for 20 hrs. Duplicate data were averaged and fitted by regression with a rectangular hyperbola to estimate the K$_i$ value of the novel compound. All compounds were independently assayed at least two times.

Ligands for σ$_1$ receptors that are potent and selective are disclosed. The structures of prezamcol and trozamicol scaffolds of carbonyl-containing vesicular acetylcholine transporter (VAChT) inhibitors are explored. Of the 23 analogues synthesized and tested, 5 display very high affinity for σ$_1$ (K$_1$=0.48-4.05 nM) and high selectivity for σ$_1$ relative to σ$_2$ receptors (σ$_1$/σ$_2$ selectivity>749-fold). Four of the five compounds (14a, 14b, 14c and 14e) showed very low affinity for VAChT (K$_i$>290 nM) and the fifth compound (14g) show moderate affinity for VAChT (K$_i$=44.2 nM). The compound [1'-(4-fluorobenzyl)-3'-hydroxy[1,4']bipiperidinyl-4-yl]-(4-fluorophenyl)-methanone (14a) displays very high affinity and selectivity for σ$_1$ receptor (K$_i$=0.48 nM, σ$_1$/σ$_2$>3600). All four of these compounds (14a, 14b, 14c and 14e) can be radiosynthesized with fluorine-18 or carbon-11, and can be used as PET probes for imaging σ$_1$ receptor in vivo.

Biological Binding Studies.

The σ$_1$ and σ$_2$ binding affinities (K$_i$, nM) of the new compounds were determined by using the competitive inhibition method with tritiated a ligands according to reported procedures.[6,40,51] The σ$_1$ binding sites were assayed by using guinea pig brain membranes with the selective radioligand (+)-[$^3$H]pentazocine. The σ$_2$ binding sites were assayed in rat liver membranes, a rich source of these sites, with [$^3$H]DTG in the presence of (+)-pentazocine (100 nM) to mask σ$_1$ sites. VAChT binding was assayed using highly expressed human VAChT assayed with homogenized and partially clarified PC12[123.7] cells by displacement of bound 5 nM (−)-[$^3$H] vesamicol. Apparent dissociation constants for binding of the novel compounds in vitro are shown in Table 1.

Binding data identified a number of structure-activity trends. First, these new analogues generally have very low affinity for σ$_2$ receptors (K$_i$>1000 nM). For VAChT, only compounds 14g, 16e, and 16g display moderate affinity of 44.2±3.03, 48.6±8.37, and 35.5±11.1 nM. For the other ligands, the K$_i$ values are greater than 100 nM. On the other hand, compounds 14a, 14b, 14c, 14e and 14g displayed very high affinity for a, receptor (K$_i$<5 nM) and very good selectivity for σ$_1$ versus σ$_2$ receptors (>1000 fold). Among these latter compounds, 14a displayed the highest affinity for σ$_1$ receptors (K$_i$=0.48±0.14 nM), very good selectivity for σ$_1$ versus σ$_2$ receptors (>3000 fold), and good selectivity for σ$_1$ receptors vs. VAChT (2800 fold), indicating that 14a is selective for σ$_1$ receptor.

14a has two fragments that contain a fluorine atom. One is in the para-position of the carbonyl group in 4-fluorobenzoylpiperidine fragment, which is easy to label by displacement of a nitro group with $^{18}$F. The other fluorine atom is in the para-position of the 1-(4-fluorobenzyl)piperidin-3-ol fragment. This other site allows incorporation of fluorine-18 in two steps. The first step is to make 4-[$^{18}$F]fluorobenzyl iodide,[52] and the second step is to make the final labeled radiotracer by N-alkylation of 13a with 4-[$^{18}$F]fluorobenzyl iodide. Labeling 14a with fluorine-18 at different positions also provides a unique way to investigate the metabolic stability of 14a in vivo by determining which site releases $^{18}$F—. In addition, the moderate lipophilicity of 14a (Log P value=2.83) indicates that compound 14a has good ability to enter into the brain and can be a suitable PET imaging probe or therapeutic agent for CNS disorders.

Comparing compounds 14a-h with 15a-g, N-benzyl substituted ligands display significantly higher binding affinities for a receptors, particularly for σ$_1$ receptor sites, whereas, N-benzoyl substituted ligands display low binding affinities for a receptors. For example, when the 4-fluorobenzoyl group in 15a is replaced by the 4-fluorobenzyl group in 14a, the σ$_1$ receptor affinity is increased dramatically, changing the K$_i$ value from 3144 nM for 15a to 0.48 nM for 14a. The same trend was observed in all other corresponding compounds. In general, compounds containing substituted benzyl groups preferred to bind to a, receptor sites; 14a-h, displayed very high σ$_1$ binding affinities in which the K$_i$ values ranged from 0.48 nM for 14a to 59.6 nM for 14h. However, compound 14g showed moderate VAChT binding affinity (44.2±3.03 nM), whereas the other compounds 14a-f and 14h displayed lower VAChT binding affinities. The observation that compounds containing the substituted benzoyl groups 15a-g led to dramatic decrease in $\sigma_1$ receptor binding affinities ($K_i$>1000 nM) is consistent with results reported in the literature.[40] This confirms that a carbonyl group between the substituted aromatic ring and the piperidine moiety plays an important role by affecting $\sigma_1$ receptor binding affinities. Without being limited by theory, the inventors hypothesize that incorporating the carbonyl group leads to more rigidity in the structure and might prevent the interaction of ligands with the $\sigma_1$ receptor binding site.

When the electron-withdrawing group fluoride (14a-d) was replaced with the electron-donating group methoxy (14e-h) at the para-position of the 4-substitued benzoylpiperidine fragment, the $\sigma_1$ binding affinities (nM) were decreased. For compounds 14a-d, a, binding affinities (nM) were 0.48±0.14, 4.03±0.47, 1.36±0.28 and 22.8±2.32 respectively; for compounds 14e-h, the $\sigma_1$ binding affinities (nM) were 2.51±0.34, 25.9±0.96, 4.05±0.88 and 59.64±2.22 respectively. The decrease in affinity ranged from 2.6 fold for 14h vs. 14d to 6.4 fold for 14b vs. 14f.

Comparing the structures of 14a, 14b, and 14c, the only difference among them is the substitution at the para-position of the benzyl moiety on the terminal piperidine ring of (3'-hydroxy-1,4'-bipiperidin-4-yl)(4-fluorophenyl)methanone. The $\sigma_1$ $K_i$-values (nM) are displayed in the order of -F>-H>-OCH$_3$ with the dissociation constant values being 0.48±0.14 for 14a, 1.36±0.28 for 14c and 4.03±0.47 for 14b. Compared with 14b, incorporating an electron-withdrawing fluorine atom at the 4-position of the benzyl group (14a) diminished the basicity of the nitrogen atom in the terminal pipeidine ring and the ligand affinity for $\sigma_1$ receptor was increased by 2.8 fold; on the contrary, incorporating an electron-donating methoxyl group (14b) enhanced the basicity of the nitrogen atom in the terminal pipeidine ring and the ligand affinity for $\sigma_1$ receptor was decreased by approximately 3 fold. A similar trend is observed in 4-methoxybenzoyl containing compounds 14e, 14f and 14g. To further test the effect of the electron density on the benzyl ring, compounds 14d and 14h containing the relatively high electron-density pyridine ring, with the N-atom in the mew-position, were synthesized and screened. However, decrease in $\sigma_1$ binding affinities was observed. For 14d, the $\sigma_1$ binding affinity was decreased more than 17 fold as expressed by $K_i$ value changing from 1.36±0.28 nM for 14c to 22.8±2.32 nM for 14d. For 14h, the $\sigma_1$ binding affinity was decreased 15 fold as expressed by $K_i$ value changing from 4.05±0.88 nM for 14g to 59.64±2.22 nM for 14h.

The presamicol scaffolds (14a-h) display substantially higher affinities for $\sigma_1$ receptors than the trozamicol scaffolds (16a-h) do. The only structural difference between presamicol and trozamicol is the position of the nitrogen atom in the terminal piperidine ring. Some trozamicol scaffold analogues display moderate $\sigma_1$ receptor binding affinities, for example 16a (50.0=7.9 nM) and 16b (91.1±19.9 nM). The difference in binding affinities for presamicol and trozamicol analogues is 11 fold for 14f vs. 16f (25.9±0.96 nM vs. 297±27 nM) and 104 fold for the most potent 14a vs. 16a (0.48±0.14 nM vs. 50.0±7.9 nM).

Overall, (1) N-alkylation with benzyl groups of (3'-hydroxy-1,4'-bipiperidin-4-yl)(4-substituted phenyl)methanone to form tertiary amines generally gives very high $\sigma_1$ receptor binding affinities and high selectivity for $\sigma_1$ receptor vs. $\sigma_2$ receptor and VAChT sites, (2) N-acylation with benzoyl groups of (3'-hydroxy-1,4'-bipiperidin-4-yl)(4-substituted phenyl)methanone to form tertiary amides diminishes the $\sigma_1$ receptor binding affinity, and (3) prezamicol analogues display high $\sigma_1$ receptor binding affinities, whereas, trozamicol analogues display moderate to low $\sigma_1$ receptor binding affinities. Although it is well known that $\sigma_1$ receptor distinguishes between enantiomers,[30,31] only racemic mixtures are used in this study.

Compounds were tested for VAChT binding using highly purified Torpedo synaptic vesicles. The $\sigma$1 and $\sigma$2 binding affinities were tested in rat brain and in guinea pig membranes, respectively. Structures and Equilibrium binding constants (Ki) are reported in Table 5 and Table 6, respectively. As in previous studies, we define ligand selectivity in terms of a selectivity index which is calculated as Ki ($\sigma$1 or $\sigma$2)/Ki (VAChT).

In the previous study, ((±)-trcms-2-Hydroxy-3-(4-(4-[$^{18}$F] fluorobenzoyDpiperidino)tetralin (FBBV) as a potent VAChT tracer is discovery. In the present study, fluorine group (FBBV) was replaced with MeNH and OCH$_2$CH$_2$F. Inspiring, TZ-3-156 (Ki=3.03 nm) displayed comparable affinity with FBBV (Ki=2.70 nm), suggesting that this structure with the amino tetralin structure in the region of ring C would produce a potent yet more hydrophilic drug that will improve the specific to nonspecific ratio for binding.

To extend our structure modification studies, the phenyl ring in fragment C was replaced with the heterocyclic ring and the results of the binding assays for compounds 11a-b, d-g, 12a-d, 13d, 20a-b, 25a-b, 31, TZ-5-3, TZ-3-156 and TZ-3-148 are shown in Table 5. Substituting the 4-postion of pyridine group with methyl group, methoxy group, fluorine group generated 11a-b, f-g, 12a-c, 25a-b, 31 and TZ-5-3 (OS-5-40, OS-5-88, TZ-4-1-92, TZ-4-1-96, OS-5-70, OS-5-82, OS-5-110, TZ-4-1-154, TZ-4-1-122, TZ-4-2-12, TZ-5-3). The affinities for VAChT are 11b (OS-5-88)>11g (TZ-4-1-96)>25b (TZ-4-1-122>25a (TZ-4-1-154)>11a (OS-5-40) >TZ-5-3>12a (OS-5-70)=12b (OS-5-82) >31 tz-4-2-12>12c (OS-5-110)>11f(TZ-4-1-92). In contrast to 4'-benzoylpiperidine (Ki=4.30±1.00 nm),[66] 4-pyridine-carbonylpropionylvesamicol 12c (OS-5-110) (Ki=118±23.6 nm) displayed 27-fold lower affinity for VAChT than 4'-benzoylpiperidine, while methyl group substituting on pyridine ring 11a (OS-5-40) (Ki=27.9±7.99 nm) was 4-fold more potent than the no substituting 12c (OS-5-110). After replaced by methoxy group, compound 11b (OS-5-88) has the highest affinity for the VAChT (Ki=8.36±0.68 nm). Surprisingly, When carbonylpropionylvesamicol group close to nitrogen atoms of the pyridine, methoxy group compound 11f (TZ-4-1-92) (Ki=121±29.2 nm) displayed lower activity than other methoxy group compound 11b (OS-5-88). To pyridine ring including, fluorine group, the introduction of a fluorine atom in a different location on the pyridine ring 11g (TZ-4-1-96), 25b (TZ-4-1-122 and 25a (TZ-4-1-154) (Ki values: 10.1±1.54, 12.7±2.41 nm) displayed higher affinity for VAChT than ethylfluorine compounds TZ-5-3 and 31 tz-4-2-12 (Ki=38±3.84 and 76.4±8.33 nm). To further probe suitable six-membered heterocyclic including nitrogen in fragment C vesamicol analogues, 1-methylpyridin-2(1H)-one derivatives 20a (TZ-4-1-148) and 20b (TZ-4-1-154) were also synthesized. It was observed that two compounds displayed lower affinity, suggesting that substitute group directly coupling nitrogen was unfavorable than no substitute nitrogen at enhancing affinity for VAChT. As observed in the pyridine ring in fragment C, the ortho-carbonylpropionylvesamicol group displayed lower affinity for VAChT than meta- and para-position (TZ-5-3 vs 31 TZ-4-2-12, 11b OS-5-88 vs 11f TZ-4-1-92, 20a TZ-4-1-148 vs 20b TZ-4-1-154). Taken together, we therefore conclude that, with suitable substitution, the pyridine can replace the phenyl group in fragment C.

Replacement of the six-member heterocyclic ring in fragment C with the five-member heterocyclic ring 11e and 11d (TZ-4-1-114 and OS-5-60) displayed high affinity (Ki values: 18.4±2.54 and 26.6±3.83 nm), suggesting that methyl group directly coupling nitrogen in five-member heterocyclic ring is more effective in alerting affinity for VAChT than the six-member heterocyclic ring in fragment C.

The introduction of an amino group into 2 (benzovesamicol) increases affinity for VAChT by an order of magnitude, making 3 (Ki=0.0065±0.0005 nM) the most potent VAChT inhibitor reported to date. We therefore sought to investigate the effect of the 5-amino group on the affinity of 4-benzoylpiperidines. In the previous study, no improvement was observed for the 4-benzoylpiperidines or the 4-(thien-2-yl)carbonylpiperidines. In the present study, 4-benzoyl group was replaced by heteroaromatic ring on fragment-C. It is consistent with previous results that 4-(heteroaromatic)-5-amino-carbonylpiperidines (12b, 12a and 12d OS-5-82, OS-5-70 and OS-5-72-2) still displayed lower affinity for VAChT than no substitute amino compounds 11b, 11a and 11d OS-5-88, OS-5-40 and OS-5-60. There was, nevertheless, a separation in affinity between the regioisomeric pairs (13d OS-5-72-1 vs 12d OS-5-72-2) similar to that observed with 2 and its 8-amino isomer. Thus, it would appear that the structure-activity relationships of the 4-heteroaromaticpiperidines largely reduced, but are not identical to, those of the 4-phenylpiperidines.

The moderate to high affinity of vesamicol and many of its analogues for σ1 and σ2 receptors reduces the selectivity of these compounds for the VAChT and potentially compromises their utility as VAChT ligands. Consequently, we also screened the target compounds for sigma binding to identify selective VAChT ligands from this new structural class of agents. Among the compounds tested, there was wide variability in affinity for $\sigma_1$ or $\sigma_2$ receptors; only one compound (TZ-3-156) displayed high affinity for σ1 receptors (Ki=13.23±0.48 nm), while all other compounds exhibited poor affinity for a receptors. As in previous studies of vesamicol analogues, we have derived estimates of ligand selectivity, expressed as a selectivity index, by comparing Ki values for VAChT obtained from highly purified Torpedo synaptic vesicles, with corresponding values for σ1 and σ2 receptors determined from rat or guinea pig brain preparations. In the present study, among the six-member heterocyclic ring analogues, 3 compounds (31 TZ-4-2-12, 11 f TZ-4-1-92 and 20b TZ-4-1-148) showed poor selectivity while 10 others (11a-b, g, 12a-c, 20a, 25a-b and TZ-5-3) (OS-5-40, OS-5-88, TZ-4-1-96, OS-5-70, OS-5-82, OS-5-110, TZ-4-1-150, TZ-4-1-154, TZ-4-1-122, TZ-5-3)) displayed moderate or high VAChT/σ selectivity (Table 5). Among the five-member heterocyclic ring analogues 11d OS-5-60, 11e TZ-4-1-114, 12d OS-5-72-2 and 13d OS-5-72-1, all compounds except 12d OS-5-72-2 displayed moderate or high VAChT/a selectivity. In contrast, among phenyl analogues TZ-3-156 and TZ-3-148, TZ-3-156 exhibited high selectivity while TZ-3-148 showed poor selectivity for VAChT.\

TABLE 5

Compounds tested for VAChT binding

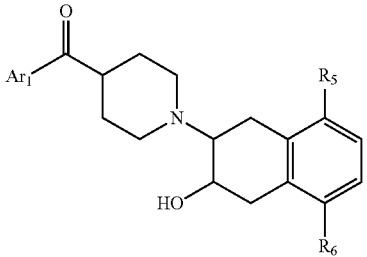

| | | | Ar₁ | R₅ | R₆ |
|---|---|---|---|---|---|
| 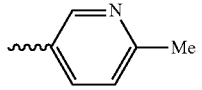 | OS-5-40 | 11a | 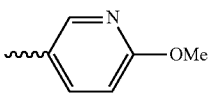 | H | H |
| 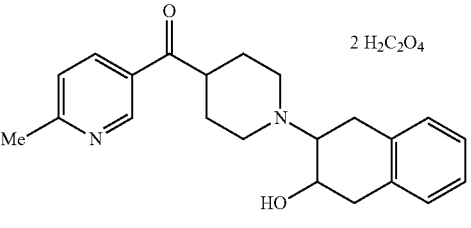 | OS-5-88 | 11b | 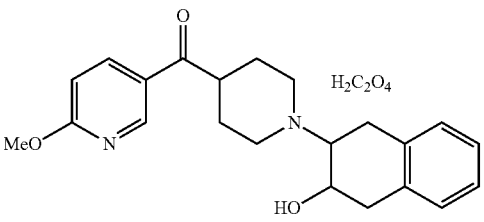 | H | H |

TABLE 5-continued
Compounds tested for VAChT binding
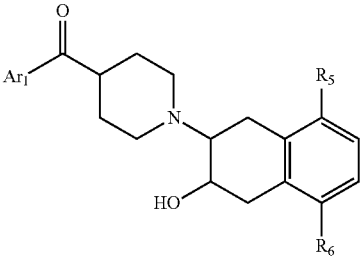
| | | | Ar₁ | R₅ | R₆ |
|---|---|---|---|---|---|
| 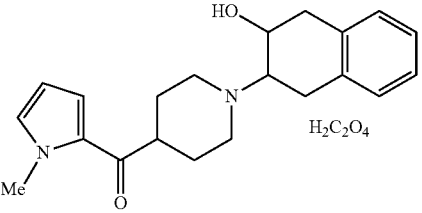 | OS-5-60 | 11d | 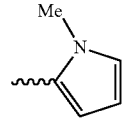 | H | H |
| 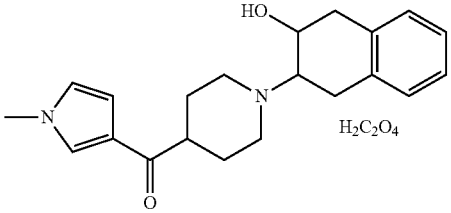 | TZ-4-1-114 | 11e | 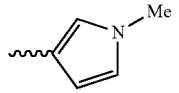 | H | H |
| 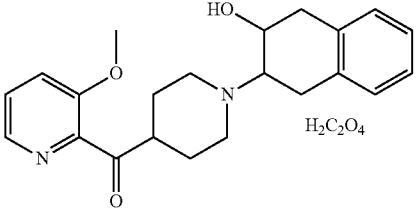 | TZ-4-1-92 | 11f | 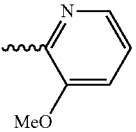 | H | H |
| 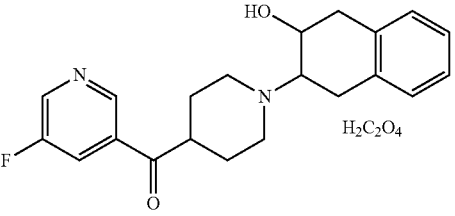 | TZ-4-1-96 | 11g | 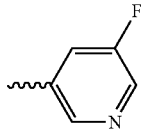 | H | H |
| 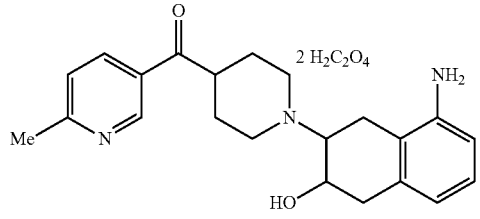 | OS-5-70 | 12a | 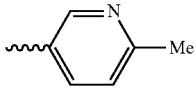 | NH₂ | H |

TABLE 5-continued

Compounds tested for VAChT binding

| | Ar₁ | R₅ | R₆ |
|---|---|---|---|
| OS-5-82  12b | 6-methoxypyridin-3-yl | NH₂ | H |
| OS-5-110  12c | pyridin-3-yl | NH₂ | H |
| OS-5-72-2  12d | 1-methyl-1H-pyrrol-2-yl | NH₂ | H |
| OS-5-2-72-1  13d | 1-methyl-1H-pyrrol-2-yl | H | NH₂ |

OS-5-72-2
C₂₅H₃₁N₃O₁₀
MW: 533.53

TABLE 5-continued

Compounds tested for VAChT binding

| | | Ar₁ | R₅ | R₆ |
|---|---|---|---|---|
| TZ-4-1-150 | 20a | (4-position of 1-methyl-2-pyridinone) | H | H |
| TZ-4-1-148 | 20b | (6-position of 1-methyl-2-pyridinone) | H | H |
| TZ-4-1-154 | 25a | (5-position of 2-fluoropyridine) | H | H |
| TZ-4-1-122 | 25b | (3-position of 2-fluoropyridine) | H | H |
| TZ-4-2-12 | 31 | (2-position of 3-(2-fluoroethoxy)pyridine) | H | H |

TABLE 5-continued

Compounds tested for VAChT binding

| | Ar₁ | R₅ | R₆ |
|---|---|---|---|
| TZ-5-3 | FH₂CH₂CO-pyridyl | H | H |
| TZ-3-156 | 4-(NHCH₃)phenyl | H | H |
| TZ-3-148 | 4-(OCH₂CH₂F)phenyl | H | H |

TABLE 6

Binding constants of structures in Table 5

| Compd. | | LogP | VAChT Ki (nM) ± SEM | σ₁ | σ₂ | σ₁/VAChT | σ₂/VAChT |
|---|---|---|---|---|---|---|---|
| OS-5-40 | 11a | 2.29 | 27.9 ± 7.99 | 2115 ± 289 | 3771 ± 886 | 75.8 | 135.2 |
| OS-5-88 | 11b | 2.64 | 8.36 ± 0.68 | 986 ± 160 | 2572 ± 139 | 117.9 | 307.6 |
| OS-5-60 | 11d | 1.42 | 18.4 ± 2.54 | 1302 ± 93 | 2553 ± 339 | 70.7 | 138.8 |
| TZ-4-1-114 | 11e | 1.84 | 26.6 ± 3.83 | 3040 ± 187 | 7708 ± 1059 | 114.2 | 289.7 |
| TZ-4-1-92 | 11f | 2.96 | 121 ± 29.2 | 20975 ± 3809 | 1564 ± 63 | 173.3 | 12.9 |
| TZ-4-1-96 | 11g | 1.99 | 10.1 ± 1.54 | 709 ± 79 | 1690 ± 56 | 70.2 | 167.3 |
| OS-5-70 | 12a | 1.33 | 48.0 ± 11.4 | 11362 ± 2040 | 27525 ± 6943 | 236.7 | 573.4 |
| OS-5-82 | 12b | 1.66 | 48.0 ± 11.4 | 5682 ± 26 | 10813 ± 1282 | 118.4 | 225.3 |
| OS-5-110 | 12c | 0.87 | 118 ± 23.6 | 20346 ± 8133 | 5078 ± 221 | 172.4 | 43.0 |
| OS-5-72-2 | 12d | 0.53 | 2310 ± 393 | 9237 ± 793 | 11396 ± 2500 | 4.0 | 4.9 |
| OS-5-2-72-1 | 13d | 0.53 | 38.7 ± 6.95 | 7664 ± 233 | 6987 ± 1482 | 198.0 | 180.5 |
| TZ-4-1-150 | 20a | 0.60 | 66.2 ± 10.2 | 3345 ± 46 | 2124 ± 251 | 50.5 | 32.1 |
| TZ-4-1-148 | 20b | 0.64 | 182 ± 64.8 | 2155 ± 182 | 3339 ± 127 | 11.8 | 18.3 |
| TZ-4-1-154 | 25a | 2.02 | 26.1 ± 2.41 | 682 ± 27 | 1750 ± 93 | 26.2 | 67.0 |
| TZ-4-1-122 | 25b | 1.65 | 12.7 ± 1.06 | 1299 ± 49 | 3529 ± 331 | 102.2 | 277.9 |
| TZ-4-2-12 | 31 | 3.18 | 76.4 ± 8.33 | 20016 ± 6798 | 303 ± 130 | 262.0 | 4.0 |
| TZ-5-3 | | 2.87 | 38 ± 3.84 | 2122 ± 49 | 1859 ± 144 | 55.8 | 48.9 |
| TZ-3-156 | | 2.61 | 3.03 ± 0.48 | 304.63 ± 21.94 | 6181.73 ± 537.07 | 100.5 | 2040 |
| TZ-3-148 | | 3.19 | | 13.23 ± 0.20 | 1885.84 ± 239.40 | | |

HPLC Conditions to Confirm the Purity of Final Compounds

The analytical HPLC system consisted of an Alltech Econosil reversed phase C18 column (250×4.6 mm, 10 uA) (Alltech Associates, Deerfield, Ill.). The mobile phase was 35% acetonitrile and 65% 0.1 M ammonium formate buffer (PH=4.5) at 1.0 mL/min flow rate. The UV wavelength is 254 uM. Under these conditions the benzamide analogs was eluted with a retention time varying from 10-50 min. The purity of the final compounds was >95%.

Chemistry

Figure 2:
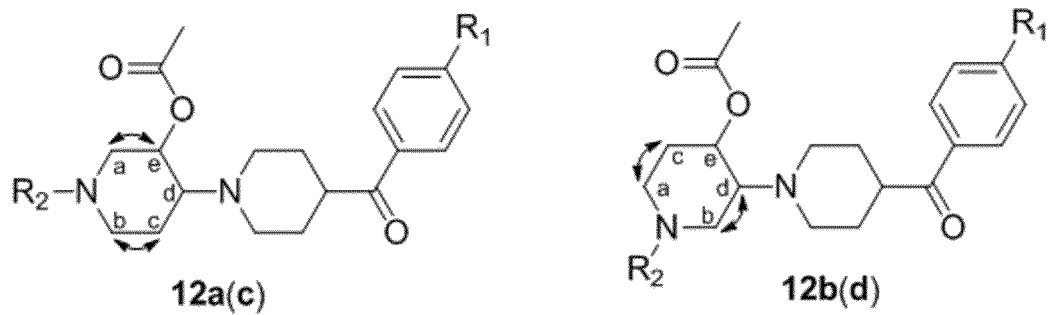
FIG. 2 illustrates assignment of regioisomers of 12a(c) and 12b(d) by $^1$H-$^1$H COSY.

The target compounds were synthesized as depicted in Schemes 1-3. The synthesis started with 1,2,3,6-tetrahydropyridine, in which the secondary amine was first protected by reacting with benzoyl chloride to form benzamide 10. The alkenyl double bond of compound 10 was oxidized by metachloroperoxybenzoic acid (m-CPBA) to form epoxide 11. The epoxide 11 was refluxed with substituted 4-benzoylpiperidine hydrochloride salts, namely (4-(4'-fluorobenzoyl)piperidine hydrochloride or 4-(4'-methoxybenzoyl)piperidine hydrochloride), in ethanol with triethylamine as the base to afford tertiary amino alcohol intermediates. To improve the yield, commercially available 4'-substituted 4-benzoylpiperidine hydrochloride salts were used in excess and the reaction temperature was kept below 75° C. This reaction afforded (3'-hydroxy-1,4'-bipiperidin-4-yl)(4-substituted phenyl)methanone intermediates and their regioisomers, (4'-hydroxy-1,3'-bipiperidin-4-yl)(4-substituted phenyl)methanone intermediates. The separation of these regioisomers by silica gel chromatography was difficult. The mixture of corresponding regioisomers was reacted with acetic anhydride to convert the free hydroxyl group to the corresponding acetates 12a-d. Subsequently, 12a and 12b were separated easily by silica gel chromatography. To confirm the structures of the regioisomers (12a(c) and 12b(d)), in addition to 1D NMR, 2D NMR was performed for regioisomers, 12c and 12d. The $^1$H, $^{13}$C NMR and HMQC spectra showed $\delta_H$=5.31/2.68, 3.79/3.12, 2.06/1.47, 3.70, 2.48 and $\delta_H$=4.89/2.66, 4.09/2.82, 1.95/1.41, 3.43 and 2.41 belong to the CH$_2$-a, CH$_2$-c, CH-d and CH-e (FIG. 2). The exact regioisomer (12a(c) or 12b(d)) were further verified by $^1$H-$^1$H COSY. For regioisomer 12c, the correlations were observed between $\delta_H$=5.31 (CH-a)/$\delta_H$=2.68 (CH-a') and $\delta_H$=2.48 (CH-e); $\delta_H$=3.79 (CH-b)/$\delta_H$=3.12 (CH-b') and $\delta_H$=2.06 (CH-c)/$\delta_H$=1.47 (CH-c'). In contrast, for regioisomer 12d, $\delta_H$=4.89 (CH-a)/$\delta_H$=2.66 (CH-a') has no correlation with $\delta_H$=2.41 (CH-e), and $\delta_H$=4.09 (CH-b)/$\delta_H$=2.82 (CH-b') and has no correlation with $\delta_H$=1.95 (CH-c)/$\delta_H$=1.41 (CH-c'), but it has correlation with $\delta_H$=1.95 (CH-c)/$\delta_H$=1.41 (CH-c') and $\delta_H$=1.41(CH-d).

12a and 12b were hydrolyzed under strongly acidic conditions to remove both the acetyl and benzoyl groups, which afforded key intermediates 13a and 13b. A similar procedure was used to make corresponding regioisomers 13c and 13d. Intermediates 13a and 13c are similar in structure to presamicol, and 13b and 13d are similar in structure to trozamicol (Scheme 1). Starting with key intermediates 13a and 13c, the target compounds 14a-h were obtained via N-alkylation with various substituted benzyl halides in yields ranging from 34% to 84%. All the substituted benzyl halides are commercially available, and they were used in slight excess (Scheme 2). The target compounds 15a-g were obtained by coupling the various substituted benzoic acids with the piperidine intermediates 13a and c using bis(2-oxo-3-oxazolidinyl)phosphonic chloride (BOP-Cl) in yields ranging from 22% to 90%. Compounds 16a-h were synthesized by following similar procedure to synthesize compounds 14a-h, except that the trozamicol analogues 13b and 13d were utilized (Scheme 3). All the products were converted into oxalates for determining the bioactivity affinities.

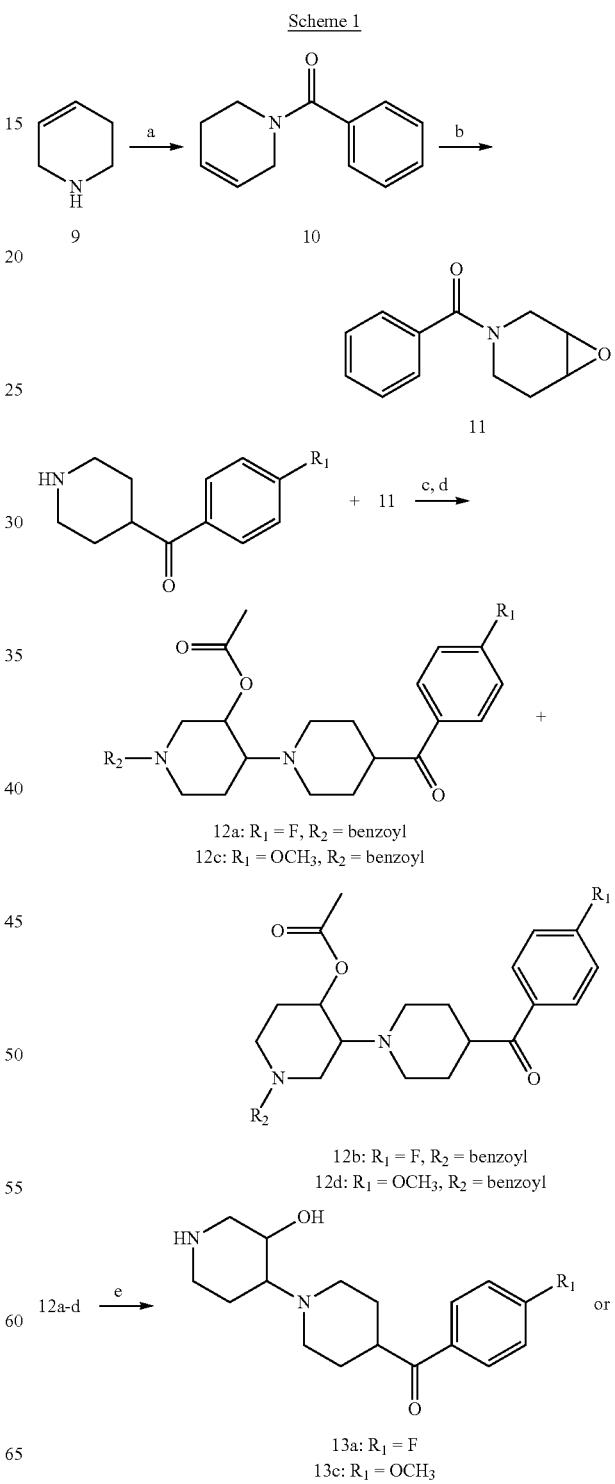

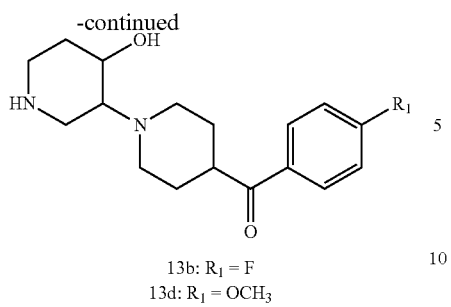
13b: $R_1 = F$
13d: $R_1 = OCH_3$
Reactions and reagents:
(a) benzoyl chloride, $(C_2H_5)_3N$; (b) m-CPBA, $CH_2Cl_2$; (c) 4-substituted benzoyl piperidine hydrochloride, $(C_2H_5)_3N$, ethanol, 0° C.; (d) acetic anhydride, $CH_2Cl_2$; (3) 6N HCl, reflux.
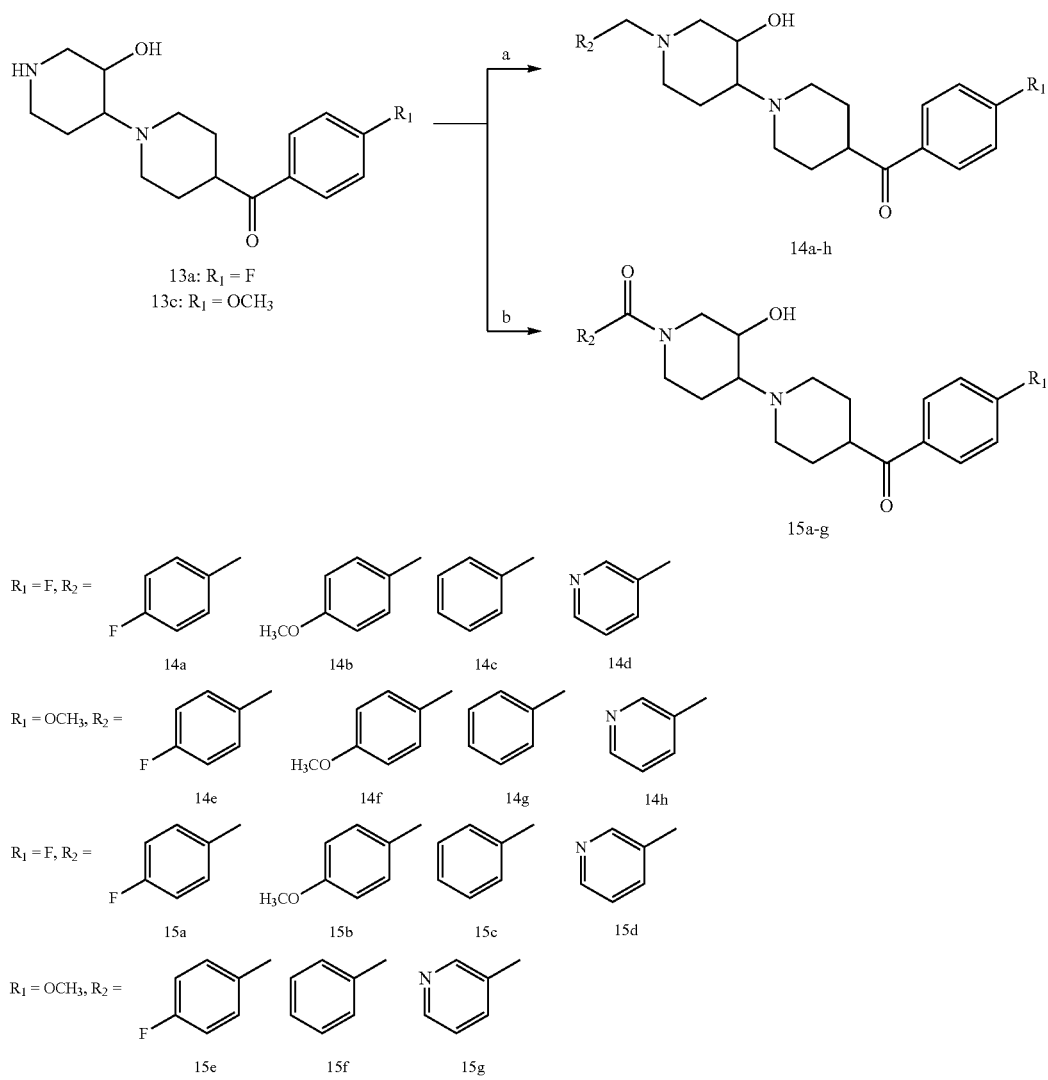
Reactions and reagents:
(a) substituted benzyl halide $(C_2H_5)_3N$, $CH_2Cl_2$;
(b) substituted benzoic acid, BOP-Cl, $(C_2H_5)_3N$, $CH_2Cl_2$

Scheme 3

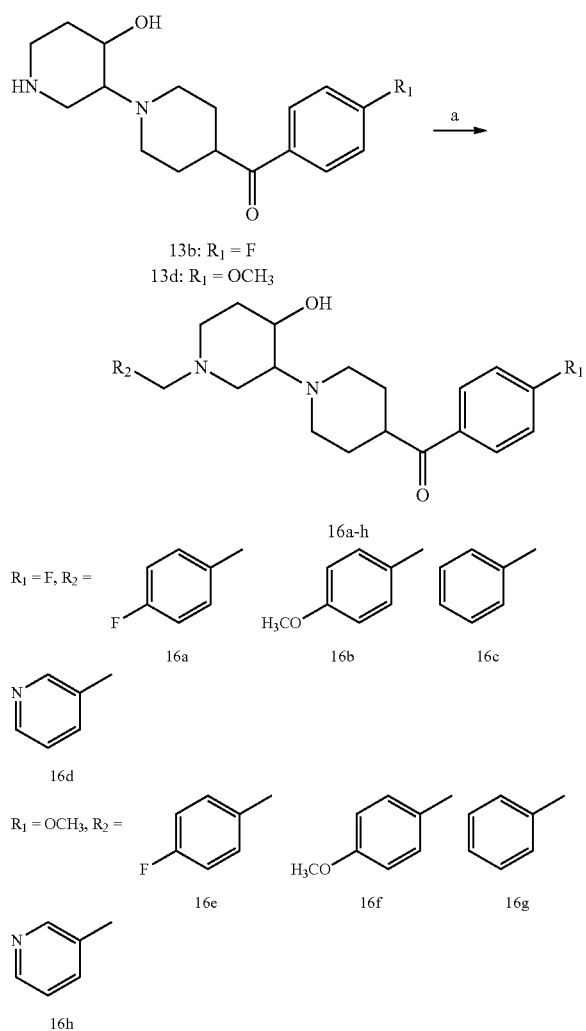

Reactions and reagents:
(a) substituted benzyl halide, ((C$_2$H$_5$)$_3$N, CH$_2$Cl$_2$ The target compounds 11a-b, d-g, 12a-d and 13d (OS-5-40, OS-5-88, OS-5-60, TZ-4-1-114, TZ-4-1-92, TZ-4-1-96, OS-5-70, OS-5-82, OS-5-110, OS-5-72-2, OS-5-2-72-1) were synthesized as depicted in Scheme 4. Piperidine-4-carboxylic acid was protected by a BOC group and then condensed with N,O-dimethylhydroxylamine after activation of the acid by CDI to give 8 that provided a versatile intermediate by halogen-metal exchange with tert-butyllithium except for 9d, to generate 9a-c, 9e-g. To 9d, the first step of the reaction consists on the formation of lithium intermediate by reacting N-methylpyrrole with tert-butyl lithium. Side reactions were avoided by cooling the reaction down to −78° C. during the addition of tert-butyl lithium, and subsequent warming up to room temperature and followed by a nucleophilic addition of the lithiated intermediate to give 9d. These key intermediates 9a-g were deprotected with TFA to give piperidine 10a-b, d-g which were reacted with epoxide 2 under S$_N$2 conditions to give target compounds 11a-b, d-g (OS-5-40, OS-5-88, OS-5-60, TZ-4-1-114, TZ-4-1-92, TZ-4-1-96) in moderate yields. Similarly, secondary amines 10a-d were reacted with 6 and then hydrolyzed by sodium hydroxide aqueous solution to provide the regioisomeric pairs 12a-d and 13d. (OS-5-70, OS-5-82, OS-5-110, OS-5-72-2, OS-5-2-72-1)

Scheme 4

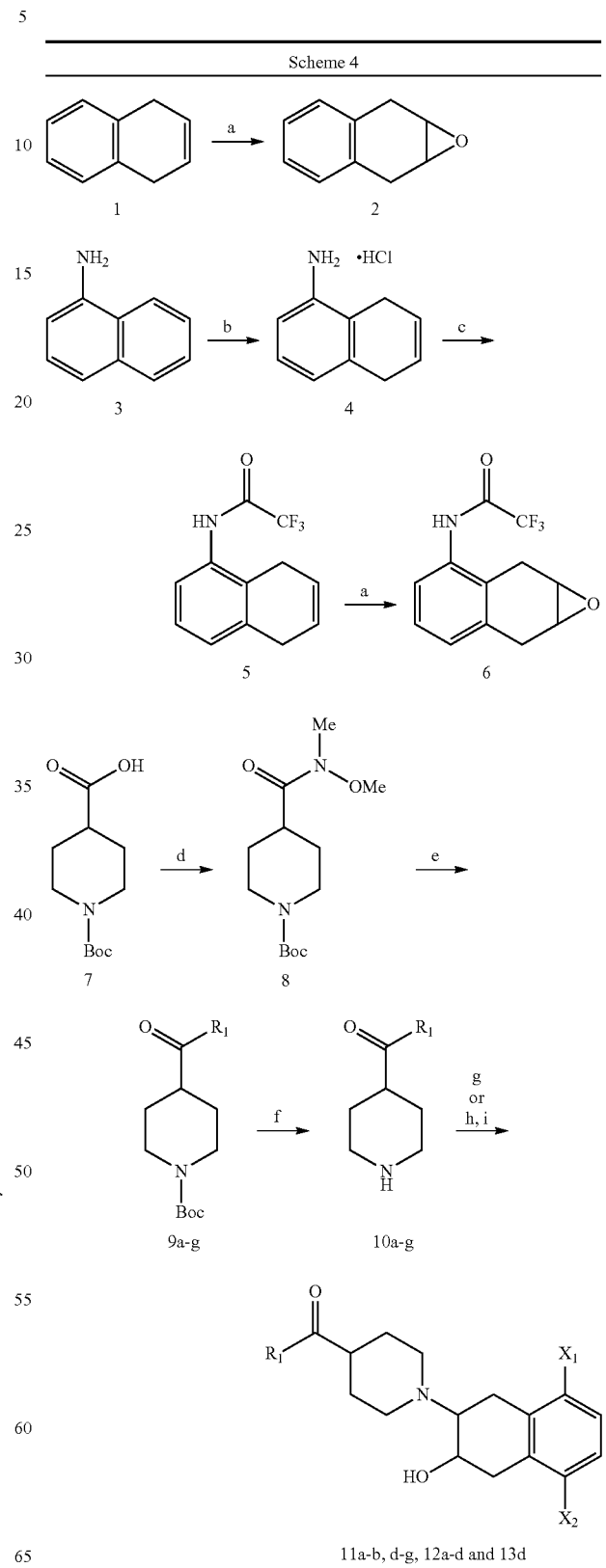

-continued

| Cpd | R₁ | X₁ | X₂ |
|---|---|---|---|
| 11a | 5-(6-methylpyridin-3-yl) | H | H |
| 11b | 5-(6-methoxypyridin-3-yl) | H | H |
| 11d | 1-methyl-1H-pyrrol-2-yl | H | H |
| 11e | 1-methyl-1H-pyrrol-3-yl | H | H |
| 11f | 3-methoxypyridin-2-yl | H | H |
| 11g | 5-fluoropyridin-3-yl | H | H |
| 12a | 5-(6-methylpyridin-3-yl) | NH₂ | H |
| 12b | 5-(6-methoxypyridin-3-yl) | NH₂ | H |
| 12c | pyridin-3-yl | NH₂ | H |
| 12d | 1-methyl-1H-pyrrol-2-yl | NH₂ | H |
| 13d | 1-methyl-1H-pyrrol-2-yl | H | NH₂ |

[a]Reagents and conditions: (a) mCPBA, CH₂Cl₂; (b) Na, EtOH, xylene; (c) (CF₃CO)₂O, NEt₃, CH₂Cl₂; (d) CDI, N,O-Dimethylhydroxylamine hydrochloride, NEt₃, CH₂Cl₂; (e) ArLi, THF; (f) TFA, CH₂Cl₂; (g) 1,4-dihydronaphthalene oxide, NEt₃, EtOH; (h) N-(trifluoroacetyl)-1-amino-5,8-dihydronaphthalene oxide, NEt₃, EtOH; (i) NaOH, H₂O, EtOH Synthesis of 20a-b (TZ-4-1-150 and TZ-4-1-148) began with pyridin-2-amine 14a-b as shown in Scheme 5. Diazotisation of pyridin-2-amine 14a-b in aqueous sulphuric acid gave tautomer 15a-b and 16a-b. According to the literature, the more polar lactam form 15a-b, which is in tautomeric equilibrium with the lactim form 16a-b, is favored in polar solvents. Therefore, N-Arylation of this substrate with iodomethane was found to strongly predominate over O-arylation, in acetone at refluxing and N-arylation producted 17a-b which could be converted into the corresponding ketone 18a-b by halogen-metal exchange in aqueous THF. Boc deprotection of ketone 18a-b with TFA followed by S$_N$2 conditions with epoxide 2 afforded target compounds 20a-b. (T1-4-1-150 and TZ-4-1-148)

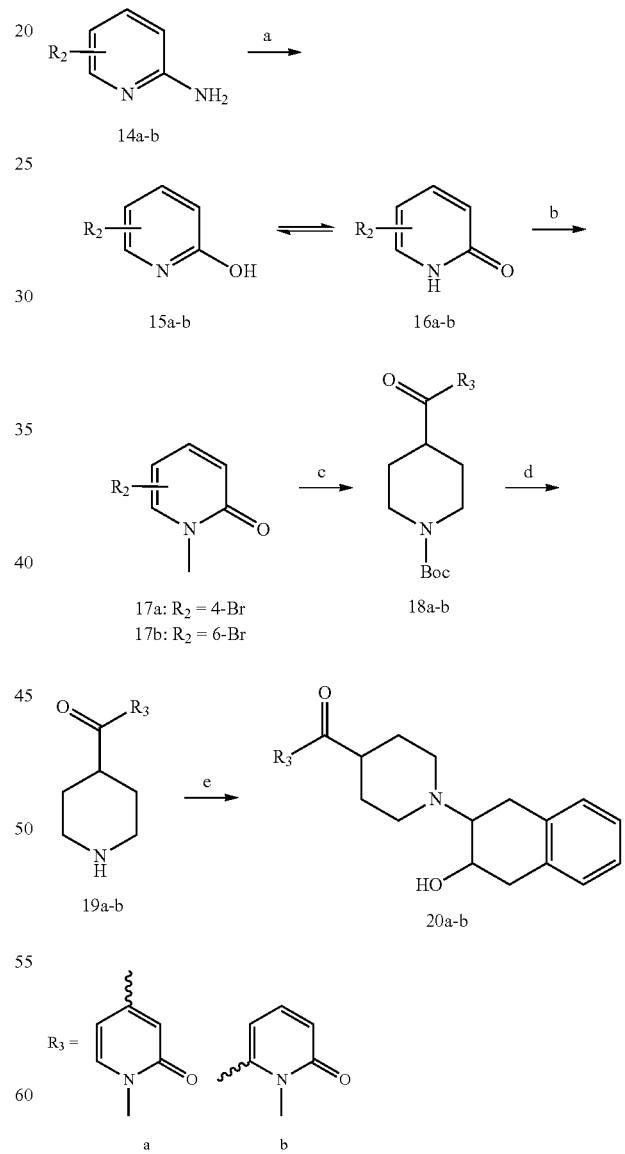

Scheme 5

17a: R₂ = 4-Br
17b: R₂ = 6-Br

[a]Reagents and conditions: (a) H₂SO₄/NaNO₂; (b) CH₃I, K₂CO₃; (c) BuLi, THF; (d) TFA, CH₂Cl₂; (e) 1,4-dihydronaphthalene oxide, NEt₃, EtOH.

Direct condensation of secondary amines and epoxide is a feasible method for obtaining vesamicol analogues. Although the preparation of the vesamicol 25a-b (TZ-4-1-154 and TZ-4-

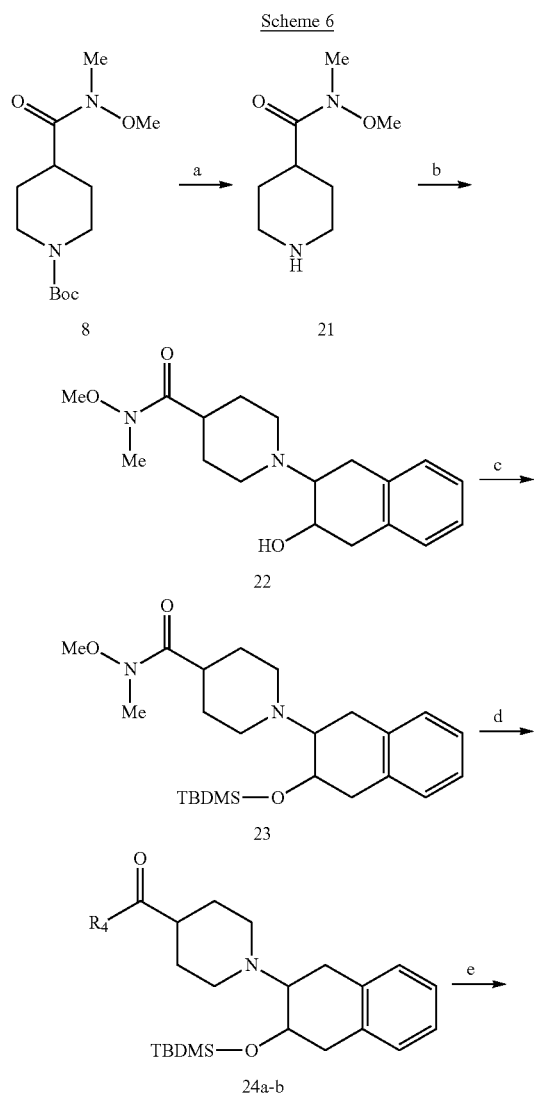

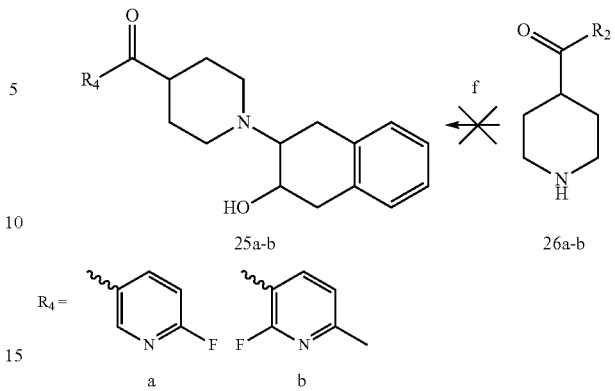

1-122) seemed trivial, it proved more problematic in practice, which probably arose from low solubility of secondary amines 26a-b (methanol, ethanol, dichloromethane, DMF, DMSO), than we had hoped. In an alternative route, the key intermediate 23 was utilized for producting vesamicol 25a-b (TZ-4-1-154 and TZ-4-1-122) which began with Boc deprotection of compound 8 with TFA followed by condensation with epoxide 2 afforded intermediate 22. Hydroxyl group of intermediate 22 was protected by a TBDMS group and then halogen-metal exchange with tert-butyllithium to provide compound 24a-b followed by an acidic workup, to liberate the hydroxy group, furnished the desired fluorine vesamicol 25a-b (TZ-4-1-154 and TZ-4-1-122) in Scheme 6.

Reagents and conditions in Scheme 6: (a) TFA, $CH_2Cl_2$; (b) 1,4-dihydronapthalene oxide, $NEt_3$, EtOH; (c) TBDMSCl, imidazole, $CH_2Cl_2$; (d) n-BuLi, THF; (e) 12N HCl, THF; (f) 1,4-dihydronaphthalene oxide, $NEt_3$, EtOH.

As for the preparation of vesamicol 31 (TZ-4-2-12), although direct nucleophilic fluorination is generally a better method from 111, we found that methyl group deprotection of compound 11f could not be obtained by $BBr_3$, TMSI, etc. We chose another way of synthesis which introduction of the ethyl fluorine moiety was realized starting from commercially available 1-bromo-2-fluoroethane, using $K_2CO_3$, to afford compound 28. Subsequently, ethyl fluorine vesamicol 31 (TZ-4-2-12) was prepared according to similar procedure of making 11a-b, d-g from compound 28 (Scheme 7).

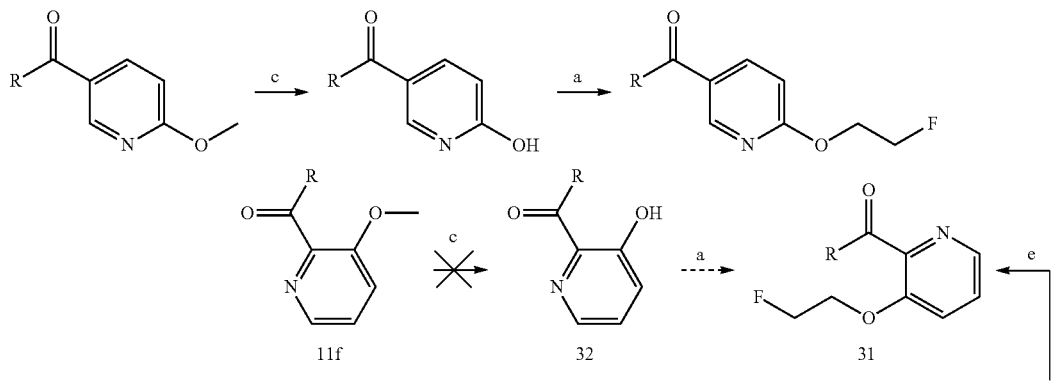

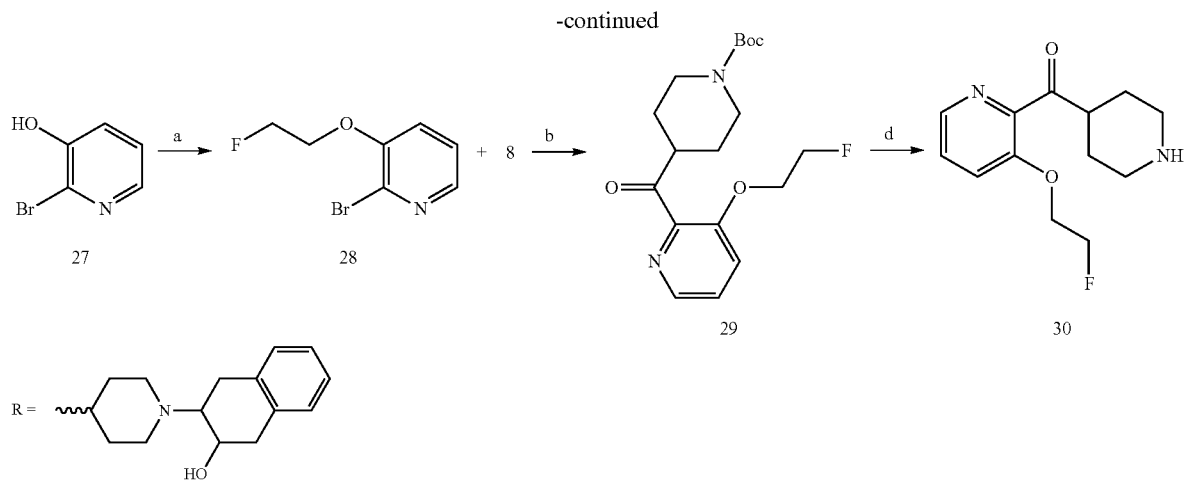

*Reagents and conditions: (a) Br(CH$_2$)$_2$F, K$_2$CO$_3$, rt; (b) BuLi, THF; (c) B$_3$Br or TMSI; (d) TFA, CH$_2$Cl$_2$, rt; (e) 1,4-dihydronaphthalene oxide, NEt$_3$, EtOH.

Example 1

Biodistribution Studies in Rats of [$^{11}$C]11e

Figure 3:
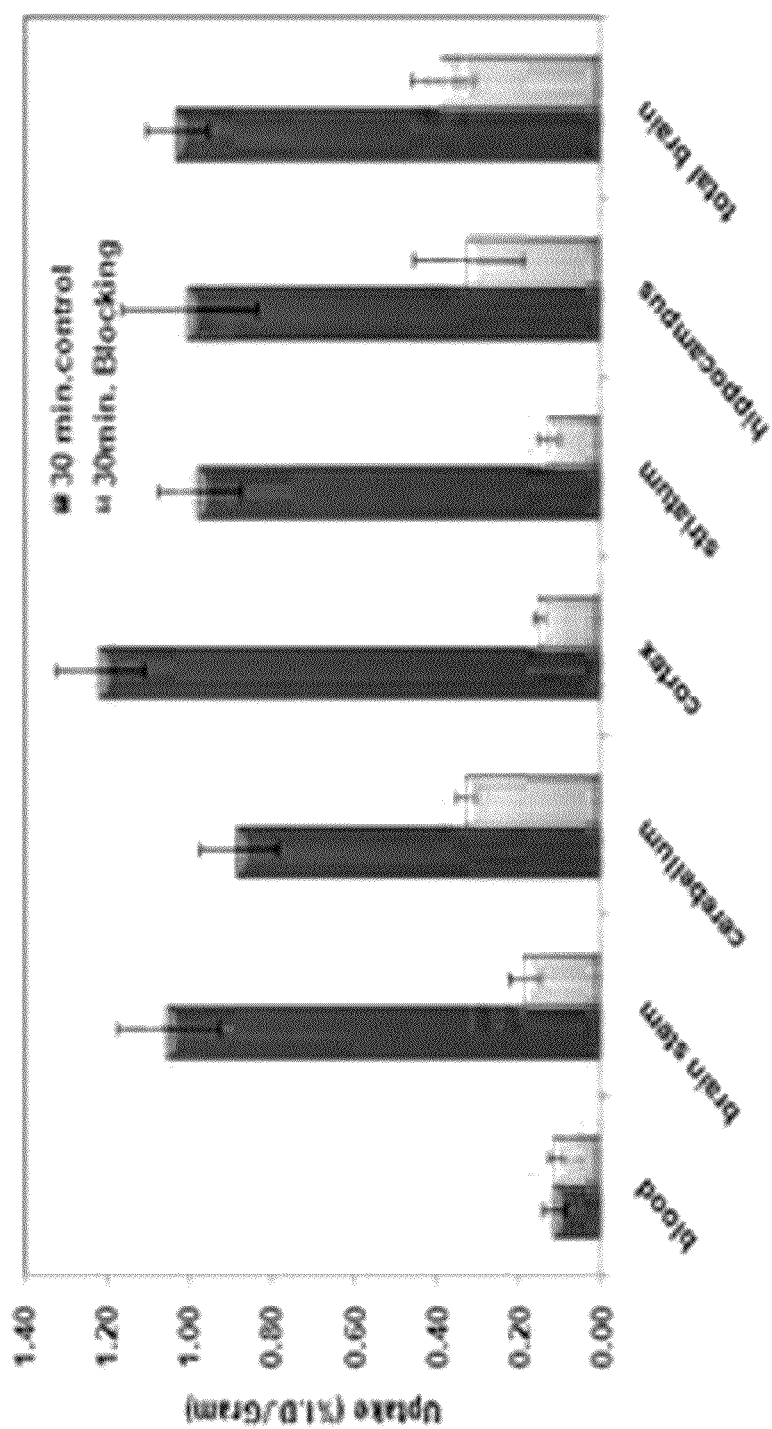
FIG. 3 illustrates the uptake of [$^{11}$C]11e in control rats.

The biodistribution and regional brain uptake of [$^{11}$C]11e was evaluated in 150-200 gram adult male Sprague-Dawley rats. Anesthetized rats were injected with 150-200 μCi of [$^{11}$C]11e and euthanized at 5, 30 and 60 min post-i.v. injection (p.i.). Target and non-target tissues were harvested and weighed; brain regions of interest were identified using gross dissection techniques. Radioactivity was measured in a well counter along with a standard dilution of the injectate. The results (Table 7 and FIG. 3) indicate high initial uptake and good retention of [$^{11}$C]11e in the brain with low radioactivity in the blood. Blocking was evaluated in rats pretreated with 1 mg/kg 11a 5 min prior to injection of [$^{11}$C]11e. The uptake at 30 min was significantly reduced for brain stem, cerebellum, cortex, striatum, hippocampus and total brain; the percentage reduction in uptake (% I.D./gram) was 82, 62, 87, 87, 68 and 63 respectively. By 30 minutes post-i.v., most of the radioactivity (31% of the total injected dose) was in the liver. Due to page limitations, distribution of radioactivity in the peripheral organs is not shown.

TABLE 7

The biodistribution of [$^{11}$C]11e in male S.D. rats.

| organs | 5 min | 30 min | 60 min |
| --- | --- | --- | --- |
| blood | 0.12 ± 0.01 | 0.09 ± 0.01 | 0.13 ± 0.01 |
| brain stem | 2.73 ± 0.27 | 1.47 ± 0.16 | 0.88 ± 0.11 |
| cerebellum | 2.60 ± 0.13 | 1.29 ± 0.10 | 0.75 ± 0.09 |
| cortex | 2.14 ± 0.24 | 1.69 ± 0.15 | 0.86 ± 0.02 |
| striatum | 2.33 ± 0.10 | 1.58 ± 0.31 | 0.77 ± 0.07 |
| hippocampus | 2.36 ± 0.08 | 1.50 ± 0.05 | 0.79 ± 0.07 |
| total brain | 2.37 ± 0.08 | 1.46 ± 0.17 | 0.80 ± 0.07 |

*selected % ID/g values (mean ± SD) with n = 4 rats per group.

Example 2

We report the radiosynthesis and in vivo evaluation of [$^{11}$C]14e as a PET tracer to quantify the σ$_1$ density in human brain. Radiosynthesis of [$^{11}$C] 14e was accomplished by alkylation of the corresponding desmethyl precursor with [$^{11}$C]CH$_3$I. Mice were injected with 80-320 μCi of [$^{11}$C]14e and euthanized at 5, 30 and 60 min. post-injection. Tissue samples were taken and converted to % ID/g for each organ. Ex vivo autoradiography studies were also conducted in mice at 30 min post-injection of the radiotracer. A microPET imaging study was also performed on a male cynomolgus monkey.

Figure 4:
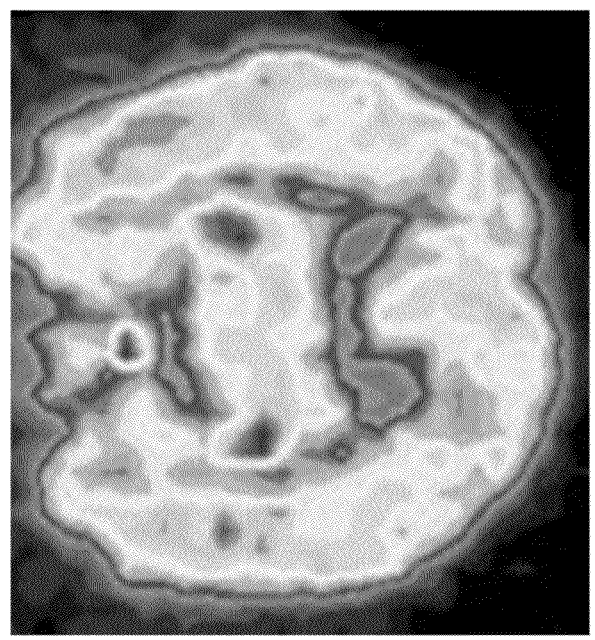
FIG. 4 illustrates transverse image of representative Micro-PET images (summed from 0-120 min) of 2 hr dynamic scans in cynoglomous Monkeys (left); and time tissue-activity curves for cortex, putamen and cerebellum (right).
Figure 4:
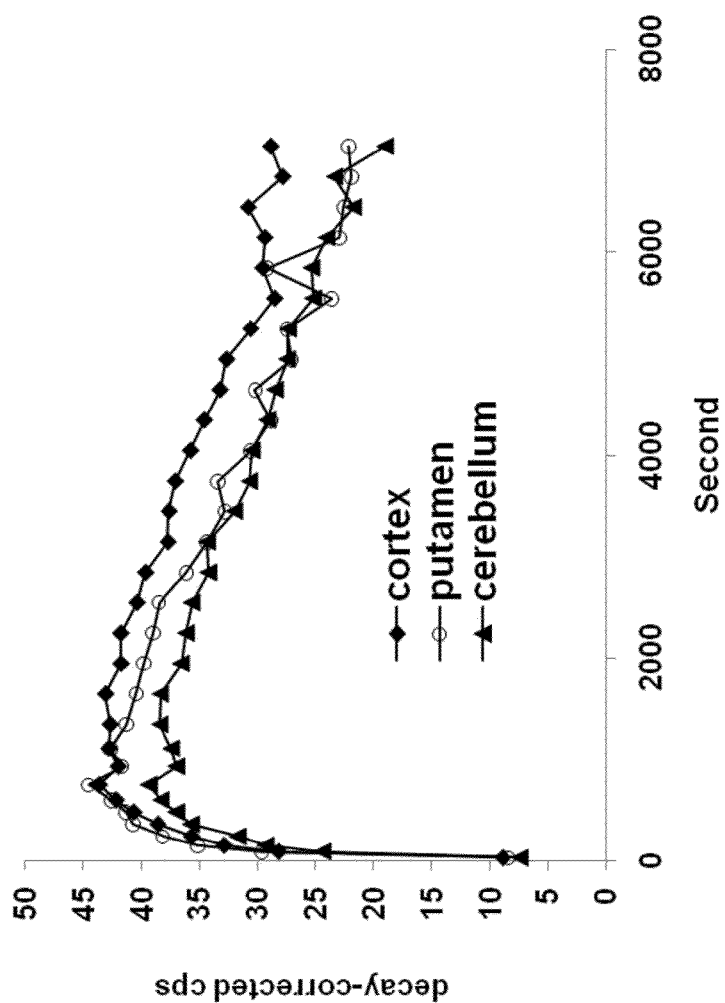

[$^{11}$C]14e was synthesized in high yield (~45%) and high specific activity (>20 Ci/μmol, EOB). High regional brain uptake (% ID/g) was observed in cerebellum, striatum, cortex and hippocampus respectively as 6.34±0.05, 6.63±0.56, 6.69±0.72 and 5.41±0.30 at 5 min; tracer levels remained high between 5 and 30 min and washed out between 30 and 60 min, indicating [$^{11}$C]14e has a suitable clearance from brain. Autoradiography studies revealed the distribution of [$^{11}$C]14e is consistent with the distribution of σ1 receptors in brain. MicroPET studies matched the σ1 distribution in brain; the tissue time-activity curves indicated [$^{11}$C]14e has a suitable clearance rate from monkey brain (FIG. 4).

These results indicate that [$^{11}$C]14e is useful as a brain imaging radiotracer. The results show that [$^{11}$C]14e has high specific binding with al receptor and suitable clearance rates from the brain.

All references cited are incorporated by reference, each in its entirety.

REFERENCES (1) Hindmarch, I.; Hashimoto, K. Cognition and depression: the effects of fluvoxamine, a sigma-1 receptor agonist, reconsidered. *Hum. Psychopharmaco.* 2010, 25, 193-200.
(2) Wollemann, M.; Benyhe, S.; Simon, J. The kappa-opioid receptor: evidence for the different subtypes. *Life Sci.* 1993, 52, 599-611.
(3) Antonini, V.; Prezzavento, O.; Coradazzi, M.; Marrazzo, A.; Ronsisvalle, S.; Arena, E.; Leanza, G. Anti-amnesic properties of (+/−)-PPCC, a novel sigma receptor ligand, on cognitive dysfunction induced by selective cholinergic lesion in rats. *J. Neurochem.* 2009, 109, 744-754.
(4) Ishikawa, M.; Hashimoto, K. The role of sigma-1 receptors in the pathophysiology of neuropsychiatric diseases. *J. Recepi., Ligand Channel Res.* 2010, 3, 25-36.
(5) Aydar, E.; Onganer, P.; Perrett, R.; Djamgoz, M. B.; Palmer, C. P. The expression and functional characterization of sigma (σ) 1 receptors in breast cancer cell lines. *Cancer Lett* 2006, 242, 245-257.
(6) Abate, C.; Mosier, P. D.; Berardi, F.; Glennon, R. A. A structure-affinity and comparative molecular field analysis of sigma-2 (sigma(2)) receptor ligands. *Cent. Nerv. Slysi. Agents Med. Chem.* 2009, 9, 246-257.

(7) Deutsch, S. I.; Weizman, A.; Goldman, M. E.; Morihisa, J. M. The sigma receptor: a novel site implicated in psychosis and antipsychotic drug efficacy. *Clin. Neuropharmacol.* 1988, 11, 105-119.

(8) Aydar, E.; Palmer, C. P.; Djamgoz, M. B. Sigma receptors and cancer: possible involvement of ion channels. *Cancer Res.* 2004, 64, 5029-5035.

(9) Kitaichi, K.; Chabot, J. G.; Moebius, F. F.; Flandorfer, A.; Glossmann, H.; Quirion, R. Expression of the purported sigma$_1$ ($\sigma_1$) receptor in the mammalian brain and its possible relevance in deficits induced by antagonism of the NMDA receptor complex as revealed using an antisense strategy. *J. Chem. Neuroanal.* 2000, 20, 375-387.

(10) Bourrie, B.; Bribes, E.; Derocq, J. M.; Vidal, H.; Casellas, P. Sigma receptor ligands: applications in inflammation and oncology. *Curr. Opin. Investig. Drugs* 2004, 5, 1158-1163.

(11) Bowen, W. D. Sigma receptors: recent advances and new clinical potentials. *Pharm. Acta Helv.* 2000, 74, 211-218.

(12) Ayata, C. Spreading depression: from serendipity to targeted therapy in migraine prophylaxis. *Cephalalgia* 2009, 29, 1097-1114.

(13) Entrena, J. M.; Cobos, E. J.; Nieto, F. R.; Cendan, C. M.; Gris, G.; Del Pozo, E.; Zamanillo, D.; Baeyens, J. M. Sigma-1 receptors are essential for capsaicin-induced mechanical hypersensitivity: Studies with selective sigma-1 ligands and sigma-1 knockout mice. *Pain* 2009, 143, 252-261.

(14) Diaz, J. L.; Zamanillo, D.; Corbera, J.; Baeyens, J. M.; Maldonado, R.; Pericas, M.; Vela, J. M.; Torrens, A. Selective sigma-1 (sigma(1)) receptor antagonists: emerging target for the treatment of neuropathic pain. *Cent. Nerv. Syst. Agents Med. Chem.* 2009, 9, 17-183.

(15) Fishback, J. A.; Robson, M. J.; Xu, Y. T.; Matsumoto, R. R. Sigma receptors: potential targets for a new class of antidepressant drug. *Pharmacoll. Ther.* 2010, 127, 271-282.

(16) Maestrup, E. G.; Wiese, C.; Schepmann, D.; Hiller, A.; Fischer, S.; Scheunemann, M.; Brust, P.; Wunsch, B. Synthesis of spirocyclic $\sigma_1$ receptor ligands as potential PET radiotracers, structure-affinity relationships and in vitro metabolic stability. *Bioorg. Med. Chem.* 2009, 17, 3630-3641.

(17) Blennow, K.; de Leon, M. J.; Zetterberg, H. Alzheimer's disease. *Lancet* 2006, 368, 387-403.

(18) Matsumoto, R. R. Targeting sigma receptors: Novel medication development for drug abuse and addiction. *Expert Rev. Clin. Pharmacol.* 2009, 2, 351-358.

(19) Volz, H. P.; Stoll, K. D. Clinical trials with sigma ligands. *Pharmacopsychicitry* 2004, 37, 5214-5220.

(20) Kunitachi, S.; Fujita, Y.; Ishima, T.; Kohno, M.; Florio, M.; Tanibuchi, Y.; Shirayama, Y.; Iyo, M.; Hashimoto, K. Phencyclidine-induced cognitive deficits in mice are ameliorated by subsequent subchronic administration of donepezil: role of sigma-1 receptors. *Brain Res.* 2009, 1279, 189-196.

(21) Maurice, T.; Su, T.-P. The pharmacology of sigma-1 receptors. *Pharmacol. Ther.* 2009, 124, 195-206.

(22) Ogawa, K.; Shiba, K.; Akhter, N.; Yoshimoto, M.; Washiyama, K.; Kinuya, S.; Kawai, K.; Mori, H. Evaluation of radioiodinated vesamicol analogs for sigma receptor imaging in tumor and radionuclide receptor therapy. *Cancer Sci.* 2009, 100, 2188-2192.

(23) John, C. S.; Bowen, W. D.; Varma, V. M.; McAfee, J. G.; Moody, T. W., Sigma receptors are expressed in human non-small cell lung carcinoma. *Life Sci.* 1995, 56, 2385-2392.

(24) Vilner, B. J.; John, C. S.; Bowen, W. D. Sigma-1 and sigma-2 receptors are expressed in a wide variety of human and rodent tumor cell lines. *Cancer Res.* 1995, 55, 408-413.

(25) John, C. S.; Gulden, M. E.; Li, J.; Bowen, W. D.; McAfee, J. G.; Thakur, M. L. Synthesis, in vitro binding, and tissue distribution of radioiodinated 2-[125I]N—(N-benzylpiperidin-4-yl)-2-iodo benzamide, 2-[125I]BP: a potential a receptor marker for human prostate tumors. *Nucl. Med. Biol.* 1998, 25, 189-194.

(26) Gao, M.; Wang, M.; Hutchins, G. D.; Zheng, Q. H. Synthesis of carbon-11-labeled piperidine ring of N-[omega-(6-methoxynaphthalen-1-yl)alkyl] derivatives as new selective PET sigma1 receptor probes. *Appl. Radial. Isot.* 2010, 68, 459-465.

(27) Brent, P. J.; Pang, G. T. Sigma binding site ligands inhibit cell proliferation in mammary and colon carcinoma cell lines and melanoma cells in culture. *Eur. J. Pharmacol.* 1995, 278, 151-160.

(28) Megalizzi, V.; Mathieu, V.; Mijatovic, T.; Gailly, P.; Debeir, O.; De Neve, N.; Van Damme, M.; Bontempi, G.; Haibe-Kains, B.; Decaestecker, C.; Kondo, Y.; Kiss, R.; Lefranc, F. 4-IBP, a sigma1 receptor agonist, decreases the migration of human cancer cells, including glioblastoma cells, in vitro and sensitizes them in vitro and in vivo to cytotoxic insults of proapoptotic and proautophagic drugs. *Neoplasia* 2007, 9, 358-369.

(29) Spruce, B. A.; Campbell, L. A.; McTavish, N.; Cooper, M. A.; Appleyard, M. V.; O'Neill, M.; Howie, J.; Samson, J.; Watt, S.; Murray, K.; McLean, D.; Leslie, N. R.; Safrany, S. T.; Ferguson, M. J.; Peters, J. A.; Prescott, A. R.; Box, G.; Hayes, A.; Nutley, B.; Raynaud, F.; Dowries, C. P.; Lambert, J. J.; Thompson, A. M.; Eccles, S. Small molecule antagonists of the σ-1 receptor cause selective release of the death program in tumor and self-reliant cells and inhibit tumor growth in vitro and in vivo. *Cancer Res.* 2004, 64, 4875-4886.

(30) Hellewell, S. B.; Bowen, W. D. A sigma-like binding site in rat pheochromocytoma (PC12) cells: decreased affinity for (+)-benzomorphans and lower molecular weight suggest a different sigma receptor form from that of guinea pig brain. *Brain Res.* 1990, 527, 244-253.

(31) Georg, A.; Friedl, A. identification and characterization of two sigma-like binding sites in the mouse neuroblastoma x rat glioma hybrid cell line NG108-15. *Pharmacol. Exp. Ther.* 1991, 259, 479-483.

(32) Hayashi, T.; Su, T. P. An update on the development of drugs for neuropsychiatric disorders: focusing on the sigma 1 receptor ligand. *Expert Opin. Ther Targets* 2008, 12, 45-58.

(33) Megalizzi, V.; Decaestecker, C.; Debeir, O.; Spiegl-Kreinecker, S.; Berger, W.; Lefranc, F.; Kast, R. E.; Kiss, R. Screening of anti-glioma effects induced by sigma-1 receptor ligands: potential new use for old anti-psychiatric medicines. *Eur. J. Cancer* 2009, 45, 2893-2905.

(34) Bhuiyan, M. S.; Tagashira, H.; Shioda, N.; Fukunaga, K. Targeting sigma-1 receptor with fluvoxamine ameliorates pressure-overload-induced hypertrophy and dysfunctions. *Expert Opin. Ther. Targets* 2010, 14, 1009-1022.

(35) Collier, T. L.; Waterhouse, R. N.; Kassiou, M. Imaging sigma receptors: applications in drug development. *Curr. Pharm. Des.* 2007, 13, 51-72.

(36) Waterhouse, R. N.; Chang, R. C.; Zhao, J.; Carambot, P. E. In vivo evaluation in rats of [(18)F]1-(2-fluoroethyl)-4-[(4-cyanophenoxy)methyl]piperidine as a potential radiotracer for PET assessment of CNS sigma-1 receptors. *Nucl. Med. Biol.* 2006, 33, 211-215.

(37) Waterhouse, R. N.; Collier, T. L. In vivo evaluation of [18F]1-(3-fluoropropyl)-4-(4-cyanophenoxymethyl)piperidine: a selective sigma-1 receptor radioligand for PET. *Nucl. Med. Biol.* 1997, 24, 127-134.

(38) Waterhouse, R. N.; Stabin, M. G.; Page, J. G. Preclinical acute toxicity studies and rodent-based dosimetry estimates of the novel sigma-1 receptor radiotracer [(18)F]FPS. *Nucl. Med. Biol.* 2003, 30, 555-563.

(39) Ishikawa, M.; Sakata, M.; Ishii, K.; Kimura, Y.; Oda, K.; Toyohara, J.; Wu, J.; Ishiwata, K.; Iyo, M.; Hashimoto, K. High occupancy of $\sigma_1$ receptors in the human brain after single oral administration of donepezil: A positron emission tomography study using [$^{11}$C]SA4503. *Int. J. Neuropsychopharmacol.* 2009, 12, 1127-1131.

(40) Costantino, L.; Gandolfi, F.; Sorbi, C.; Franchini, S.; Prezzavento, O.; Vittorio, F.; Ronsisvalle, Leonardi, A.; Poggesi, E.; Brasili, L. Synthesis and structure-activity relationships of 1-aralkyl-4-benzylpiperidine and 1-aralkyl-4-benzylpiperazine derivatives as potent a ligands. *J. Med. Chem.* 2005, 48, 266-273.

(41) Enomoto, K.; Cossu, M. F.; Edwards, C.; Oka, T. Induction of distinct types of spontaneous electrical activities in mammary epithelial cells by epidermal growth factor and insulin. *Proc. Nail. Acad. Sci. U.S.A.* 1986, 83, 4754-4758.

(42) Custers, F. G.; Leysen, J. E.; Stoof, J. C.; Herscheid, J. D. Vesamicol and some of its derivatives: questionable ligands for selectively labelling acetylcholine transporters in rat brain. *Eur. J. Pharmacol.* 1997, 338, 177-183.

(43) De Castro, B. M.; Pereira, G. S.; Magalhaes, V.; Rossato, J. I.; De Jaeger, X.; Martins-Silva, C.; Leles, B.; Lima, P.; Gomez, M. V.; Gainetdinov, R. R.; Caron, M. G.; Izquierdo, I.; Cammarota, M.; Prado, V. F.; Prado, M. A. M. Reduced expression of the vesicular acetylcholine transporter causes learning deficits in mice. *Genes Brain Behav.* 2009, 8, 23-35.

(44) Giboureau, N.; Som, I. M.; Boucher-Arnold, A.; Guilloteau, D.; Kassiou, M. PET radioligands for the vesicular acetylcholine transporter (VAChT). *Curr. Top. Med. Chem.* 2010, 10, 1569-1583.

(45) Hashimoto, K.; Ishiwata, K. Sigma receptor ligands: possible application as therapeutic drugs and as radiopharmaceuticals. *Curr. Pharm. Des.* 2006, 12, 3857-3876.

(46) Ishiwata, K.; Kawamura, K.; Yajima, K.; QingGeLeTu; Mori, H.; Shiba, K. Evaluation of (+)-p-[$^{11}$C]methylvesamicol for mapping sigma$_1$ receptors: a comparison with [$^{11}$C]SA4503. *Nucl. Med. Biol.* 2006, 33, 543-548.

(47) Shiba, K.; Ogawa, K.; Mori, H. In vitro characterization of radioiodinated (+)-2-[4-(4-iodophenyl)piperidino]cyclohexanol [(+)-pIV] as a sigma-1 receptor ligand. *Bioorg. Med. Chem.* 2005, 13, 1095-1099.

(48) Bando, K.; Taguchi, K.; Ginoza, Y.; Naganuma, T.; Tanaka, Y.; Koike, K.; Takatoku, K. Synthesis and evaluation of radiolabeled piperazine derivatives of vesamicol as SPECT agents for cholinergic neurons. *Nucl. Med. Biol.* 2001, 28, 251-260.

(49) Colabufo, N. A.; Abate, C.; Contino, M.; Inglese, C.; Niso, M.; Berardi, F.; Perrone, R. PB 183, a sigma receptor ligand, as a potential PET probe for the imaging of prostate adenocarcinoma. *Bioorg. Med. Chem. Lett* 2008, 18, 1990-1993.

(50) Efange, S. M. N.; Khare, A. B.; von Hohenberg, K.; Mach, R. H.; Parsons, S. M.; Tu, Z. Synthesis and in vitro biological evaluation of carbonyl group-containing inhibitors of vesicular acetylcholine transporter. *J. Med. Chem.* 2010, 53, 2825-2835.

(51) Byl, N. N. Learning-based animal models: Task-specific focal hand dystonia. *ILAR J.* 2007, 48, 411-431.

(52) Lara, A.; Damasceno, D. D.; Pires, R.; Gros, R.; Gomes, E. R.; Gavioli, M.; Lima, R. F.; Guimaraes, D.; Lima, P.; Bueno Jr, C. R.; Vasconcelos, A.; Roman-Campos, D.; Menezes, C. A. S.; Sirvente, R. A.; Salemi, V. M.; Mady, C.; Caron, M. G.; Ferreira, A. J.; Brum, P. C.; Resende, R. R.; Cruz, J. S.; Gomez, M. V.; Prado, V. F.; De Almeida, A. P.; Prado, M. A. M.; Guatimosim, S. Dysautonomia due to reduced cholinergic neurotransmission causes cardiac remodeling and heart failure. *Mol. Cell. Biol.* 2010, 30, 1746-1756.

(53) Barker, W. W.; Luis, C. A.; Kashuba, A.; Luis, M.; Harwood, D. G.; Loewenstein, D.; Waters, C.; Jimison, P.; Shepherd, E.; Sevush, S.; Graff-Radford, N.; Newland, D.; Todd, M.; Miller, B.; Gold, M.; Heilman, K.; Doty, L.; Goodman, I.; Robinson, B.; Pearl, G.; Dickson, D.; Duara, R. Relative frequencies of Alzheimer disease, Lewy body, vascular and frontotemporal dementia, and hippocampal sclerosis in the State of Florida Brain Bank. *Alzheimer Dis. Assoc. Disord.* 2002, 16, 203-212.

(54) Parsons, S. M.; Prior, C.; Marshall, I. G. Acetylcholine transport, storage, and release. *Int Rev. Neurobiol.* 1993, 35, 279-390.

(55) Marlatt, M. W.; Webber, K. M.; Moreira, P. I.; Lee, H. G.; Casadesus, G.; Honda, K.; Zhu, X.; Perry, G.; Smith, M. A. Therapeutic opportunities in Alzheimer disease: one for all or all for one? *Curr. Med. Chem.* 2005, 12, 1137-1147.

(56) Martinez, A.; Castro, A. Novel cholinesterase inhibitors as future effective drugs for the treatment of Alzheimer's disease. *Expert Opin Inv Drug* 2006, 15, 1-12.

(57) Racchi, M.; Mazzucchelli, M.; Porrello, E.; Lanni, C.; Govoni, S. Acetylcholinesterase inhibitors: novel activities of old molecules. *Pharmacol. Res.* 2004, 50, 441-451.

(58) Roman, G. C. Rivastigmine for subcortical vascular dementia. *Expert Rev Neurother* 2005, 5, 309-313.

(59) Chez, M. G.; Aimonovitch, M.; Buchanan, T.; Mrazek, S.; Tremb, R. J. Treating autistic spectrum disorders in children: utility of the cholinesterase inhibitor rivastigmine tartrate. *J. Child Neural.* 2004, 19, 165-169.

(60) Efange, S. M. In vivo imaging of the vesicular acetylcholine transporter and the vesicular monoamine transporter. *FASEB J.* 2000, 14, 2401-2413.

(61) Rogers, G. A.; Parsons, S. M.; Anderson, D. C.; Nilsson, L. M.; Bahr, B. A.; Kornreich, W. D.; Kaufman, R.; Jacobs, R. S.; Kirtman, B. Synthesis, in vitro acetylcholine-storage-blocking activities, and biological properties of derivatives and analogues of trans-2-(4-phenylpiperidino) cyclohexanol (vesamicol). *J. Med. Chem.* 1989, 32, 1217-1230.

(62) Efange, S. M. N.; Mach, R. H.; Smith, C. R.; Khare, A. B.; Foulon, C.; Akella, S. K.; Childers, S. R.; Parsons, S. M. Vesamicol Analogs as Sigma-Ligands—Molecular Determinants of Selectivity at the Vesamicol Receptor. *Biochem. Pharmacol.* 1995, 49, 791-797.

(63) Altar, C. A.; Marien, M. R. [3H]vesamicol binding in brain: autoradiographic distribution, pharmacology, and effects of cholinergic lesions. *Synapse* 1988, 2, 486-493.

(64) Bahr, B. A.; Clarkson, E. D.; Rogers, G. A.; Noremberg, K.; Parsons, S. M. A kinetic and allosteric model for the acetylcholine transporter-vesamicol receptor in synaptic vesicles. *Biochemistry (Mosc)*. 1992, 31, 5752-5762.

(65) Zea-Ponce, Y.; Mavel, S.; Assaad, T.; Kruse, S. E.; Parsons, S. M.; Emond, P.; Chalon, S.; Giboureau, N.; Kassiou, M.; Guilloteau, D. Synthesis and in vitro evaluation of new benzovesamicol analogues as potential imaging probes for the vesicular acetylcholine transporter. *Bioorg. Med. Chem.* 2005, 13, 745-753.

(66) Tu, Z.; Efange, S. M.; Xu, J.; Li, S.; Jones, L. A.; Parsons, S. M.; Mach, R. H. Synthesis and in vitro and in vivo evaluation of 18F-labeled positron emission tomography (PET) ligands for imaging the vesicular acetylcholine transporter. *J. Med. Chem.* 2009, 52, 1358-1369.

(67) Efange, S. M.; Khare, A. B.; von Hohenberg, K.; Mach, R. H.; Parsons, S. M.; Tu, Z. Synthesis and in vitro biological evaluation of carbonyl group-containing inhibitors of vesicular acetylcholine transporter. *J. Med. Chem.* 2010, 53, 2825-2835.

(68) Waterhouse, R. N. Determination of lipophilicity and its use as a predictor of blood-brain barrier penetration of molecular imaging agents. *Mol Imaging Biol* 2003, 5, 376-389.

What is claimed is:

1. A compound of structure

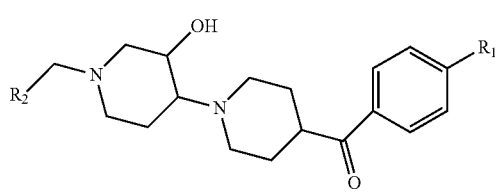

or a salt thereof, wherein $R_1$ is selected from the group consisting of F and $OCH_3$, and $R_2$ is selected from the group consisting of

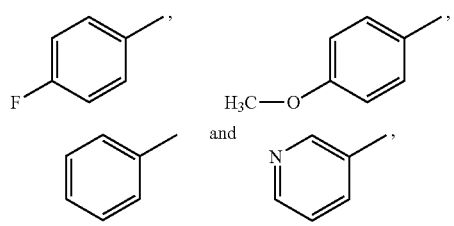

and wherein the compound exhibits selectivity for σ1 in comparison to vesicular acetylcholine transporter (VAChT), and wherein the compound comprises a positron-emitting nuclide.

2. A compound or salt thereof in accordance with claim 1, wherein $R_1$ is F.

3. A compound or salt thereof in accordance with claim 1, wherein the compound is selected from the group consisting of

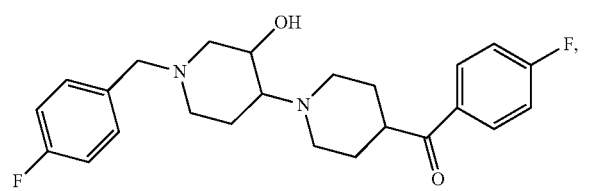 [SMILES: O=C(c1ccc(F)cc1)C1CCN(C2CCN(Cc3ccc(F)cc3)CC2O)CC1]

-continued

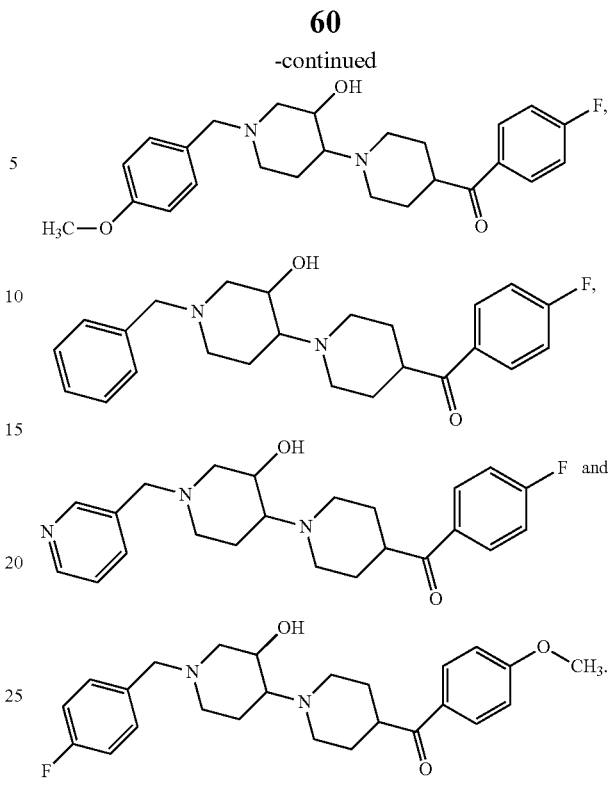

4. A compound or salt thereof in accordance with claim 3, wherein an F an $^{18}$F.

5. A compound or salt thereof in accordance with claim 1, wherein the compound is selected from the group consisting of

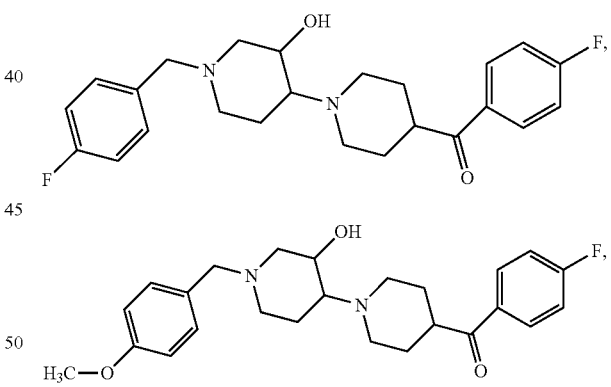

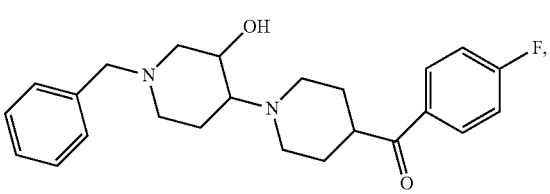

-continued

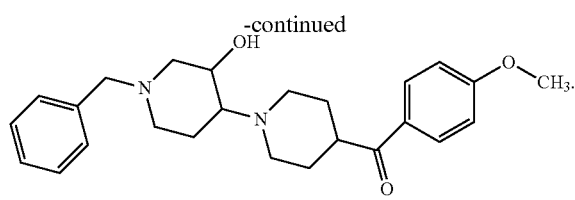

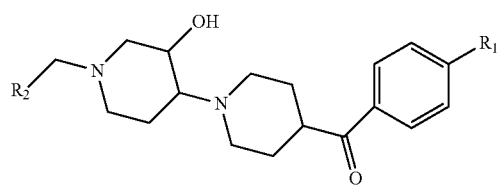

6. A compound or salt thereof in accordance with claim 1, wherein the compound is selected from the group consisting of

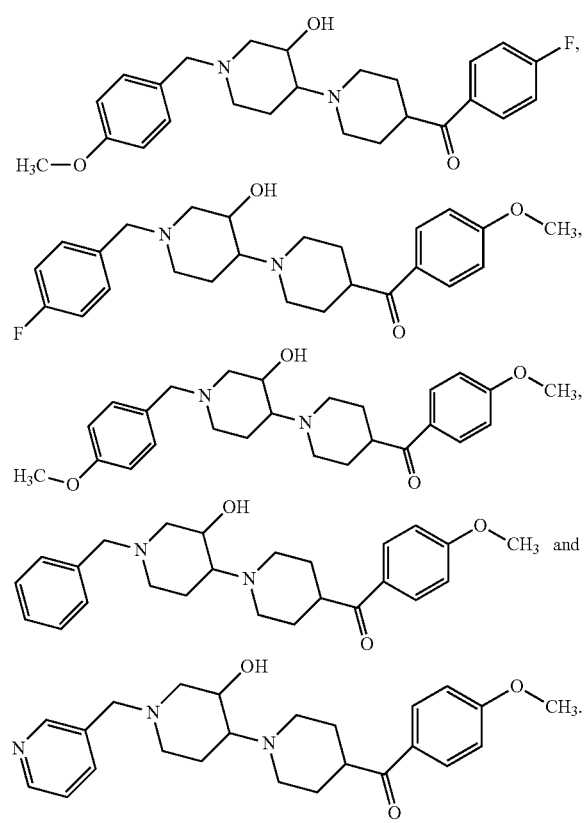

7. A compound or salt thereof in accordance with claim 6, wherein a methoxy is an $^{11}$C methoxy.

8. A compound or salt thereof in accordance with claim 1, wherein the compound is

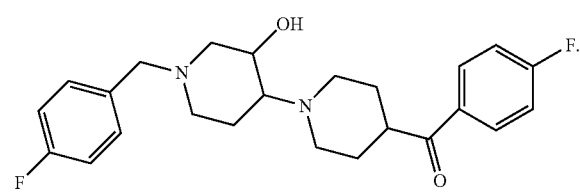 [SMILES: O=C(c1ccc(F)cc1)C1CCN(C2CCN(Cc3ccc(F)cc3)CC2O)CC1]

9. A compound or salt thereof in accordance with claim 1, wherein at least 1 carbon is a $^{11}$C.

10. A method of imaging distribution of sigma-1 receptors in a subject, comprising:
  administering to a subject a radiolabeled compound of structure or a salt thereof, Wherein $R_1$ is selected from the group consisting of F and $OCH_3$, and $R_2$ is selected from the group consisting of

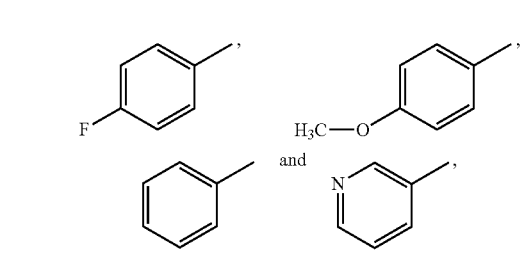

and wherein the compound exhibits selectivity for σ1 in comparison to vesicular acetylcholine transporter (VAChT), and wherein the compound comprises a positron-emitting nuclide; and subjecting the subject to positron emission tomography (PET) scanning.

11. A method in accordance with claim 10, wherein $R_1$ is an $^{18}$F.

12. A method in accordance with claim 10, wherein $R_1$ is an $O^{11}CH_3$.

13. A method in accordance with claim 10, wherein the compound is selected from the group consisting of

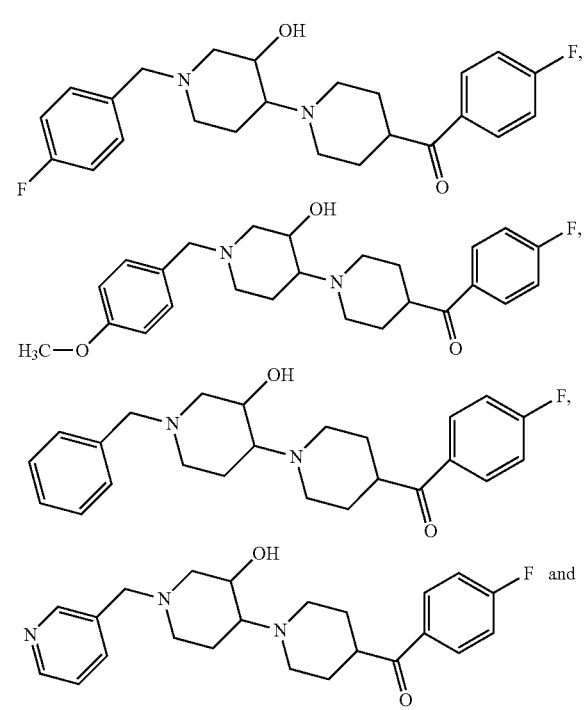

-continued

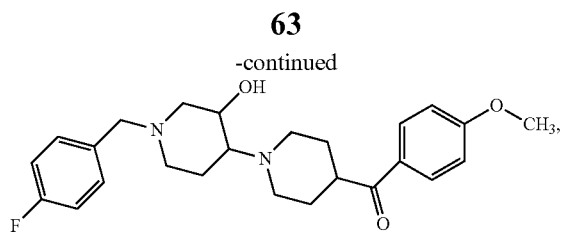

wherein an F is an $^{18}$F.

14. A method in accordance with claim 10, wherein the compound is selected from the group consisting of

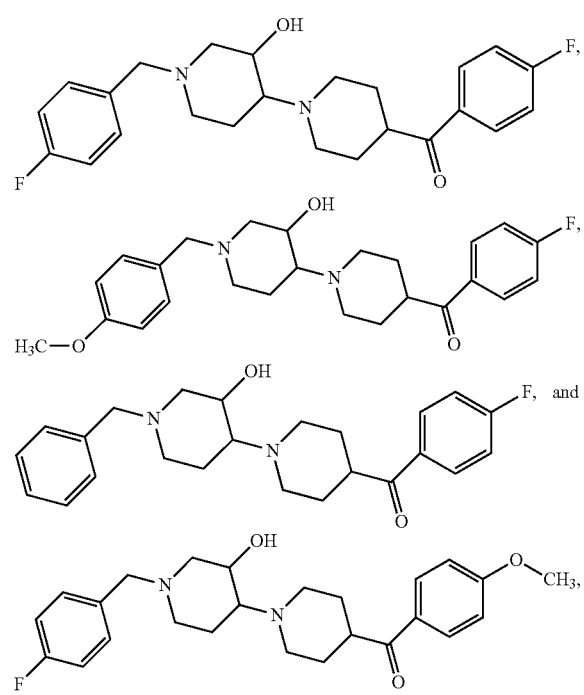

wherein an F is an $^{18}$F.

15. A method in accordance with claim 10, wherein the compound is selected from the group consisting of

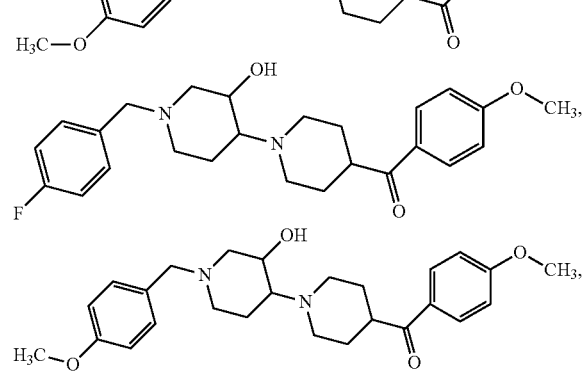

-continued

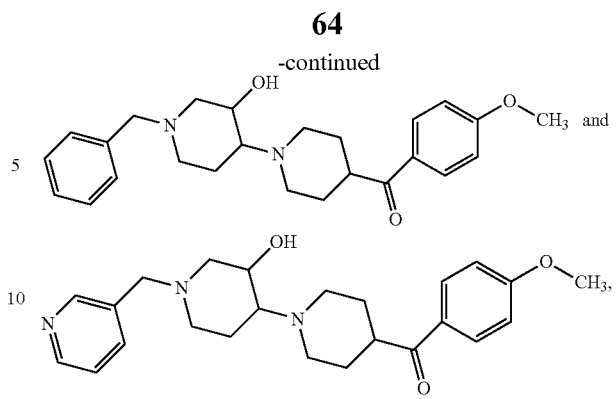

wherein an OCH$_3$ an O$^{11}$CH$_3$.

16. A method in accordance with claim 10, wherein the compound is selected from the group consisting of

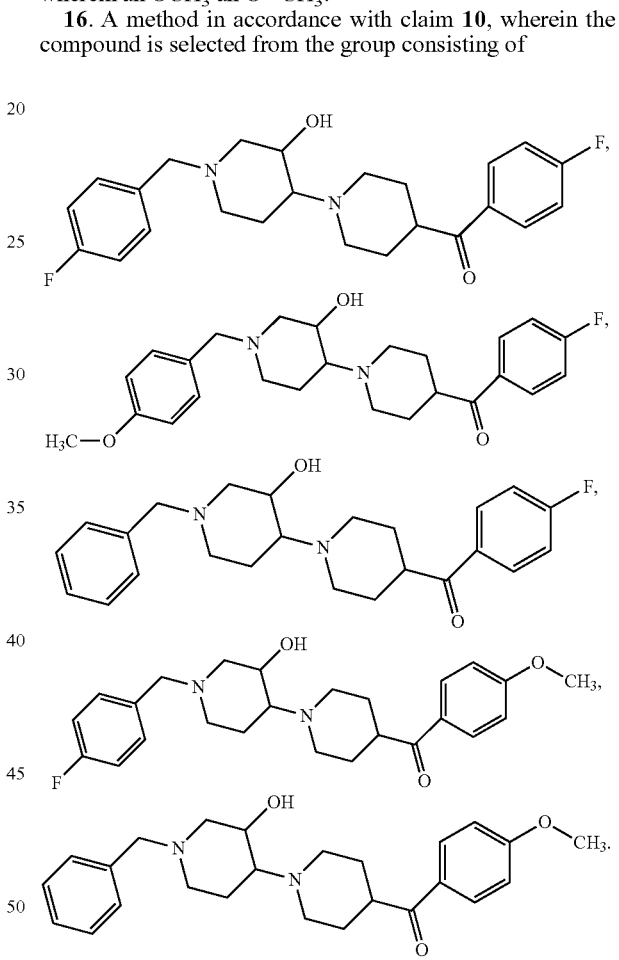

17. A method in accordance with claim 10, wherein the compound is

* * * * *